US008207311B2

(12) United States Patent
Pilkington et al.

(10) Patent No.: US 8,207,311 B2
(45) Date of Patent: Jun. 26, 2012

(54) OVR115 ANTIBODY COMPOSITIONS AND METHODS OF USE

(75) Inventors: Glenn Pilkington, Rye (AU); Gilbert-Andre Keller, Belmont, CA (US); Wenlu Li, South San Francisco, CA (US); Laura Corral, Jamaica Plain, MA (US); Iris Simon, Amsterdam (NL)

(73) Assignee: diaDexus, Inc., South San Francisco, CA (US)

( * ) Notice: Subject to any disclaimer, the term of this patent is extended or adjusted under 35 U.S.C. 154(b) by 1179 days.

(21) Appl. No.: 10/556,478

(22) PCT Filed: May 17, 2004

(86) PCT No.: PCT/US2004/015258
§ 371 (c)(1),
(2), (4) Date: Dec. 7, 2006

(87) PCT Pub. No.: WO2004/104173
PCT Pub. Date: Dec. 2, 2004

(65) Prior Publication Data
US 2007/0104647 A1    May 10, 2007

Related U.S. Application Data

(60) Provisional application No. 60/559,730, filed on Apr. 5, 2004, provisional application No. 60/471,068, filed on May 16, 2003.

(51) Int. Cl.
| | | |
|---|---|---|
| C07K 16/00 | (2006.01) | |
| C07K 17/00 | (2006.01) | |
| C07K 17/14 | (2006.01) | |
| C12P 21/08 | (2006.01) | |
| A61K 39/395 | (2006.01) | |
| A61K 39/00 | (2006.01) | |
| G01N 33/53 | (2006.01) | |
| G01N 33/574 | (2006.01) | |
| C12N 5/07 | (2010.01) | |
| C12N 5/16 | (2006.01) | |

(52) U.S. Cl. ............. 530/388.1; 530/388.8; 530/388.85; 530/391.1; 530/391.3; 530/391.7; 424/130.1; 424/134.1; 424/138.1; 424/141.1; 435/7.1; 435/7.23; 435/326; 435/330

(58) Field of Classification Search .................. None
See application file for complete search history.

(56) References Cited

U.S. PATENT DOCUMENTS 6,455,668 B1    9/2002  Mack et al.
6,682,890 B2 *  1/2004  Mack et al. .................. 435/6

FOREIGN PATENT DOCUMENTS

WO    WO0012758    3/2000
WO    WO0104141    1/2001

OTHER PUBLICATIONS

Bowie et al (Science, 1990, 257: 1306-1310).*
Roger, I et al, 1988, Bioscience Reports, 8(4): 359-368.*
Zips et al, 2005, In vivo, 19: 1-8.*
Lee et al, 1999, J Immunol, 163: 6292-6300.*
Kirkin et al, 1998, APMIS, 106 : 665-679.*
Mellman I, 2006, The Scientist, 20(1): 47-56.*
White et al, 2001 (Ann Rev Med, 52: 125-145).*
Bodey et al, 2000, Anticancer Res, 20: 2665-2676.*
MPSRCH search result, 2008, us-10-556-478.3.rai, result 7, p. 1.*
Bowie (Science, 1990, 257:1306-1310).*
Paul. Fundamental Immunology, 3rd Edition, 1993, pp. 292-295.*
Rudikoff, Giusti, Cook, and Scharff. Single amino acid substitution altering antigen-binding specificity. Proceedings of the National Academy of Sciences, 1982. vol. 79, pp. 1979-1983.*
Colman. Effects of amino acid sequence changes on antibody-antigen interactions. Research in Immunology, 1994. vol. 145, pp. 33-36.*
Mac Callum, Martin, and Thornton. Antibody-antigen interactions: contact analysis and binding site topography. Journal of Molecular Biology, 1996. vol. 262, pp. 732-745.*
Wallrapp et al., "A Novel Transmembrane Serine Protease (TMPRSS3) Overexpressed in Pancreatic Cancer", Cancer Research 2000 60:2602-2606.

* cited by examiner

*Primary Examiner* — Anne M. Gussow
(74) *Attorney, Agent, or Firm* — Licata & Tyrrell P.C.; Keith R. McCollum

(57) ABSTRACT

The invention provides isolated anti-ovarian, pancreatic, lung or breast cancer antigen (Ovr115) antibodies that bind to Ovr115 on a mammalian cell in vivo. The invention also encompasses compositions comprising an anti-Ovr115 antibody and a carrier. These compositions can be provided in an article of manufacture or a kit. Another aspect of the invention is an isolated nucleic acid encoding an anti-Ovr115 antibody, as well as an expression vector comprising the isolated nucleic acid. Also provided are cells that produce the anti-Ovr115 antibodies. The invention encompasses a method of producing the anti-Ovr115 antibodies. Other aspects of the invention are a method of killing an Ovr115-expressing cancer cell, comprising contacting the cancer cell with an anti-Ovr115 antibody and a method of alleviating or treating an Ovr115-expressing cancer in a mammal, comprising administering a therapeutically effective amount of the anti-Ovr115 antibody to the mammal.

46 Claims, 20 Drawing Sheets

Figure 1A: Results of FACS Analysis of Ovr115 Transfected Mouse LMTK Cells
A. Donkey Anti-Mouse Ig-PE
B. MAb Ovr115 D3 & Donkey Anti-Mouse Ig-PE
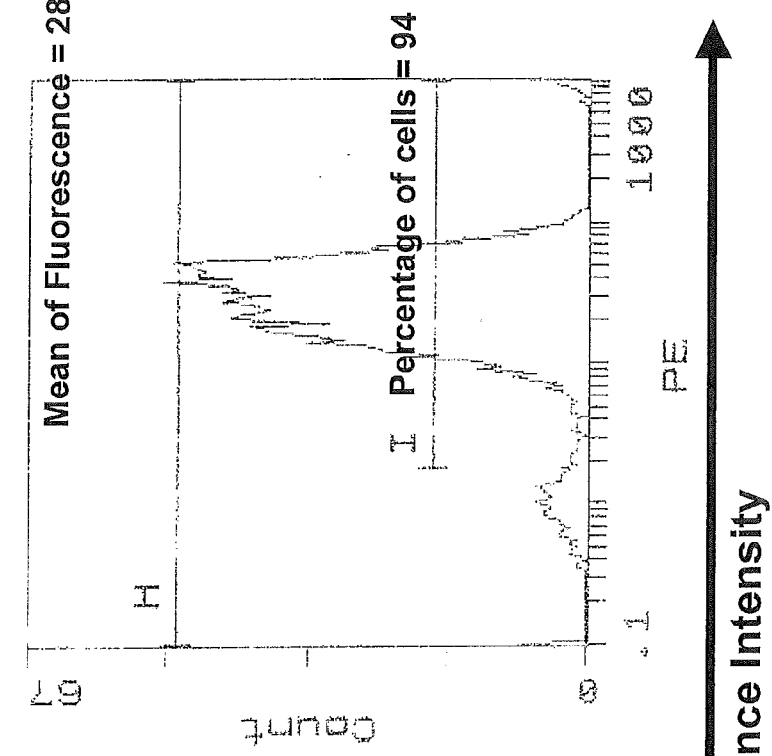
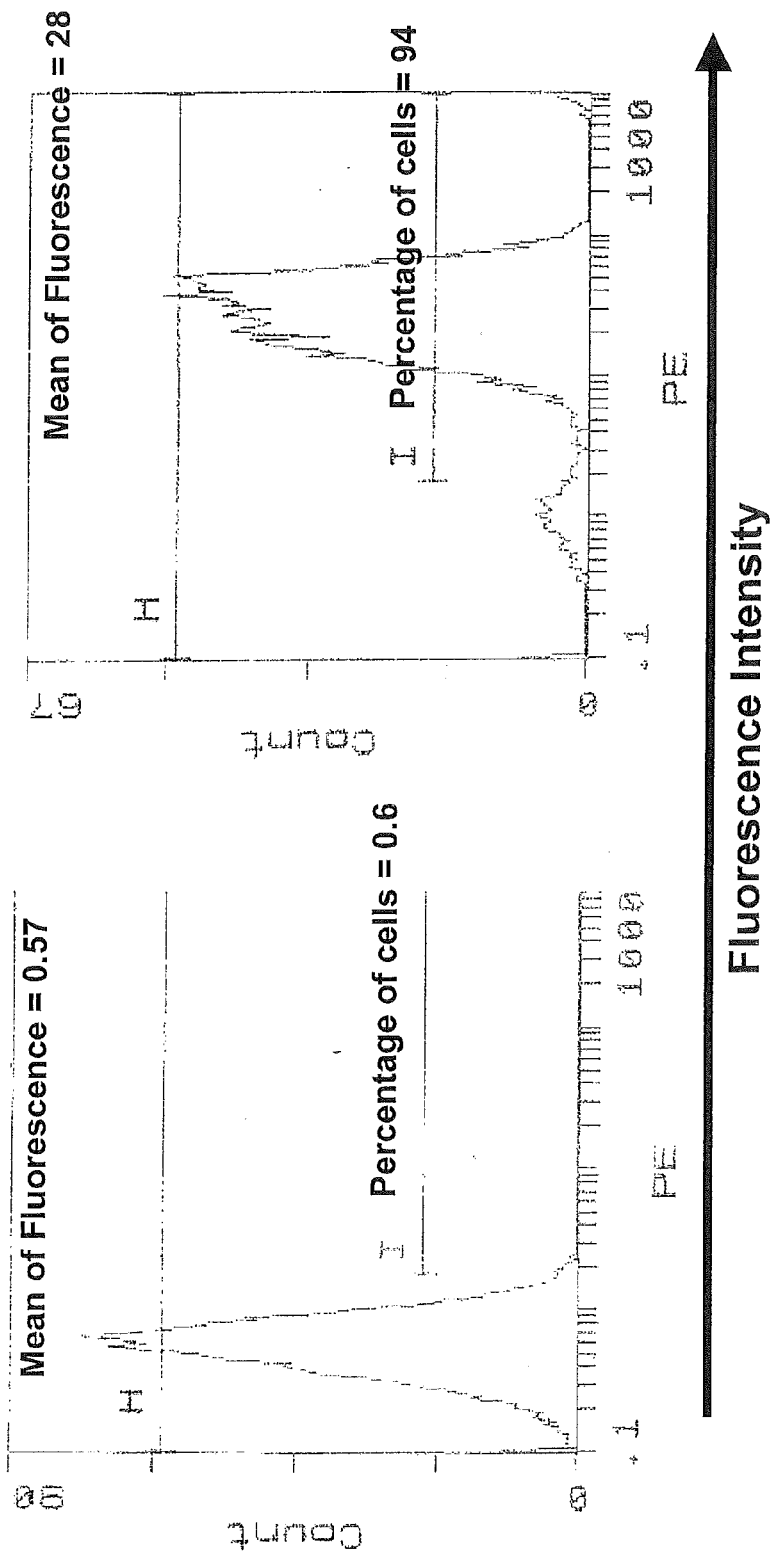

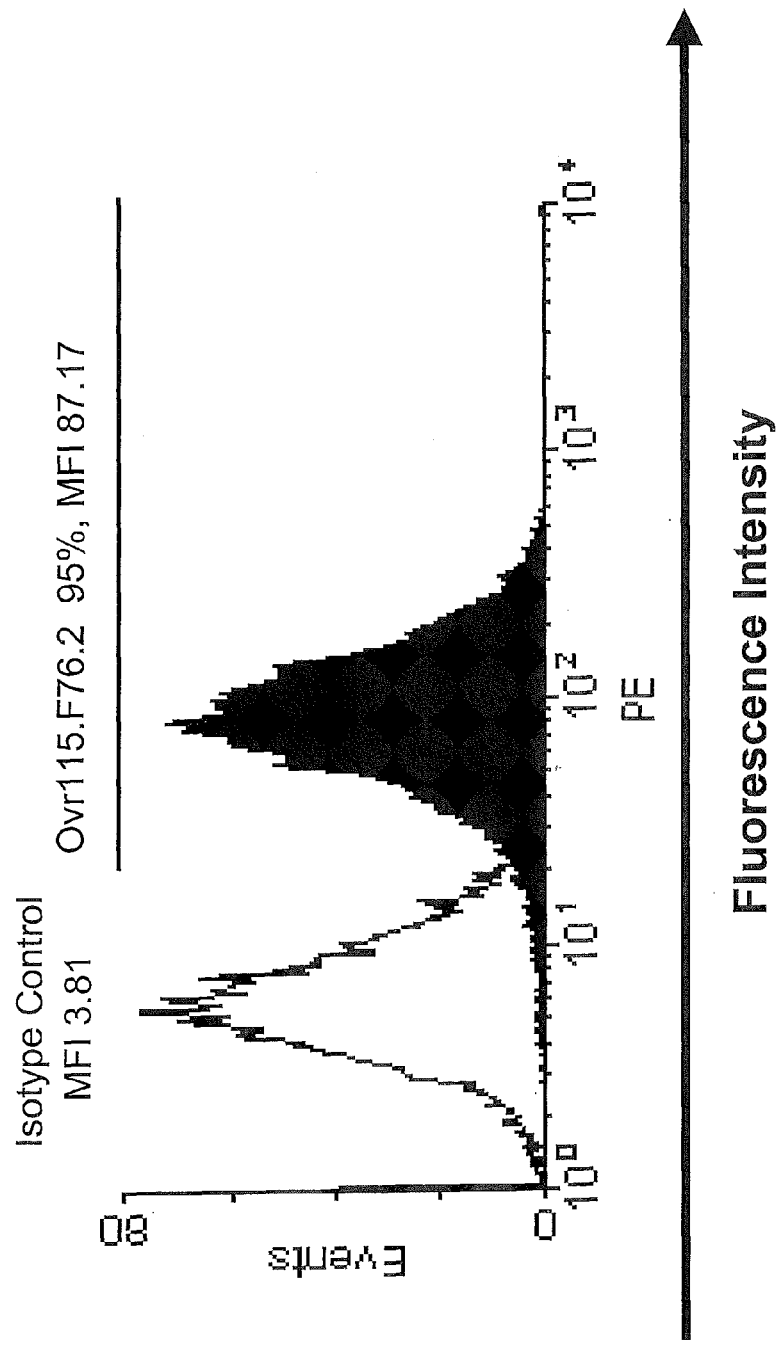
Figure 1B: Ovr115.F76.2 MAb Binds to A431 (QPCR+) Cell Line

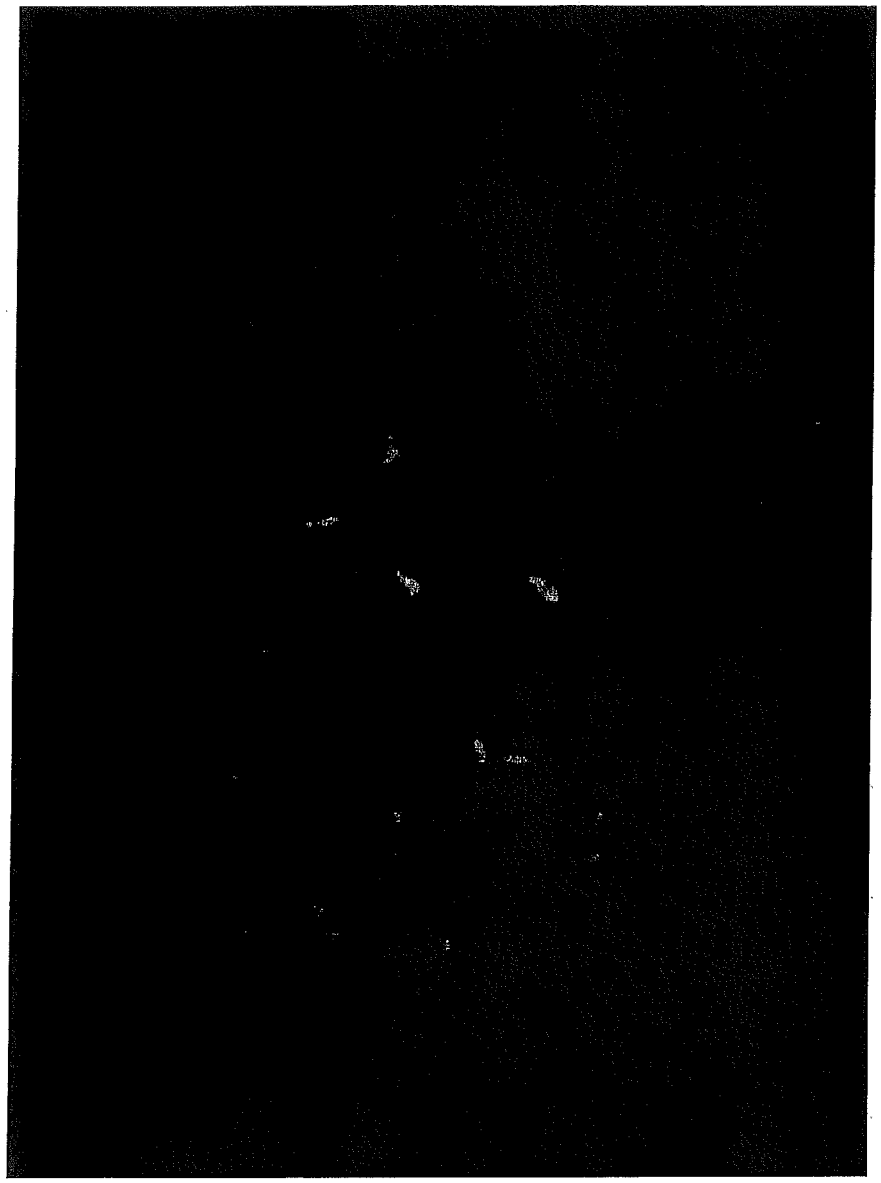
Figure 2: Ovr115.A51.2 binds to the surface of live ovarian CaOV3 cancer cells

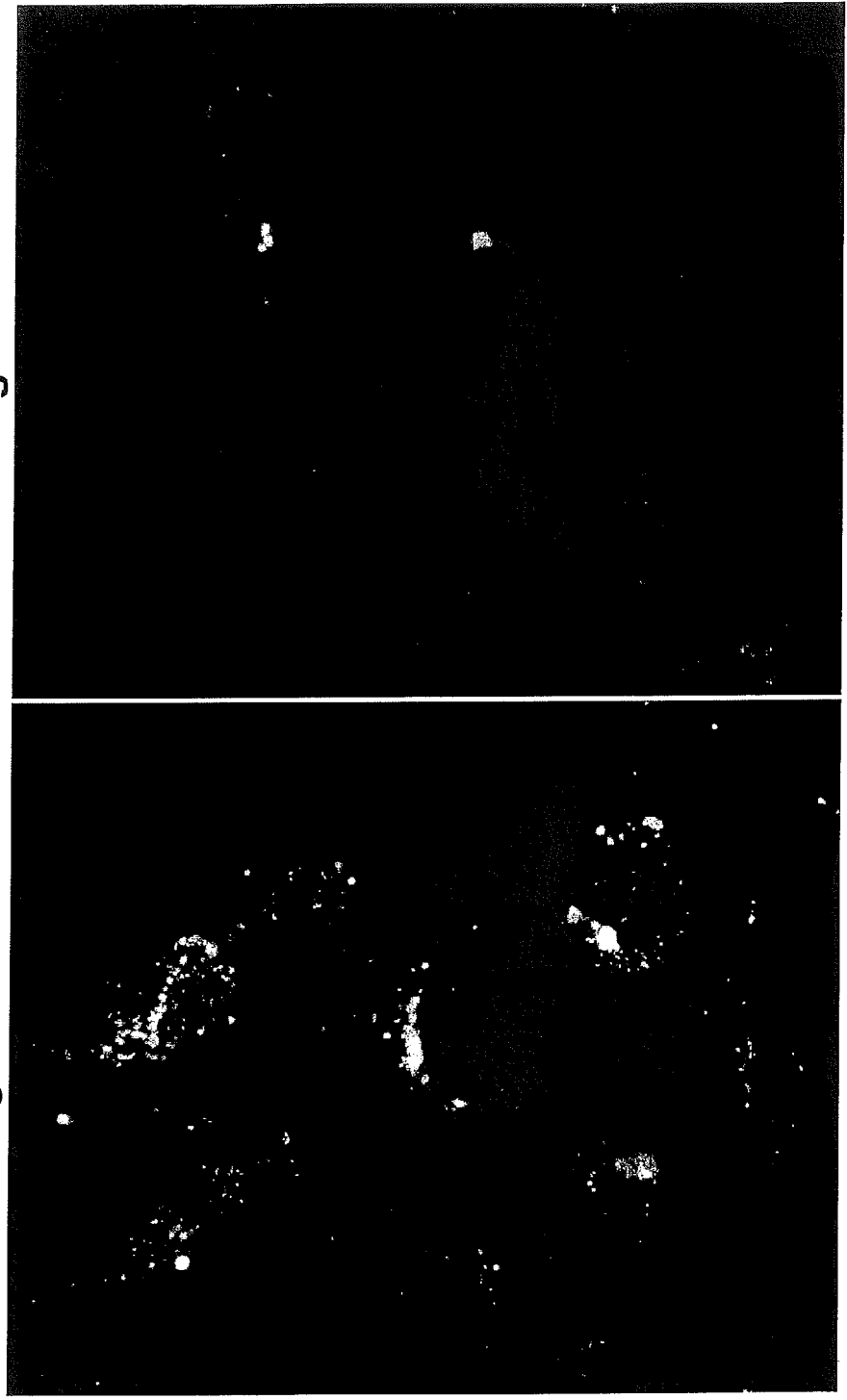
Figure 3: Cy3-A51.2 binds to live ovarian CaOV-3 cancer cells

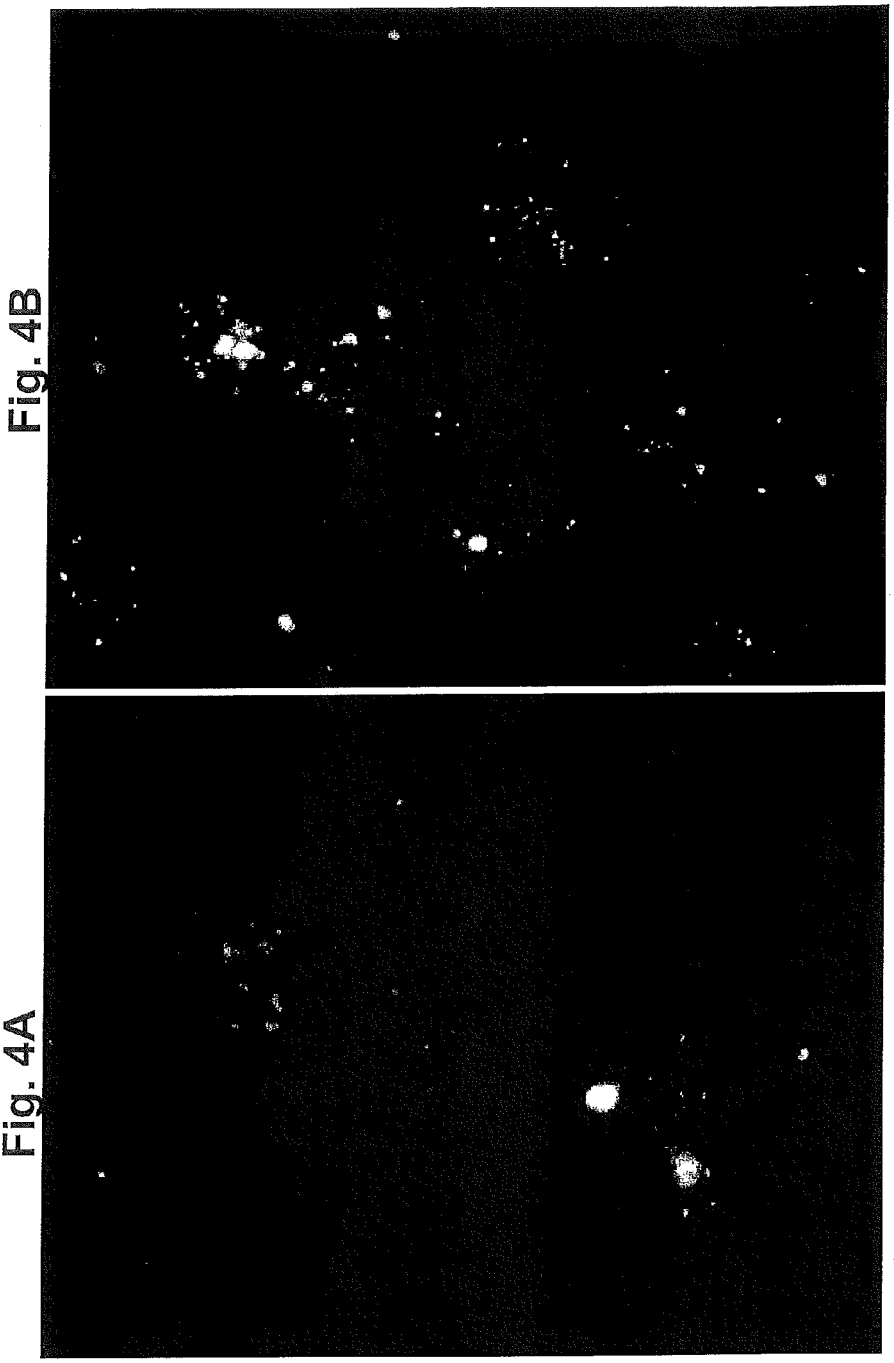

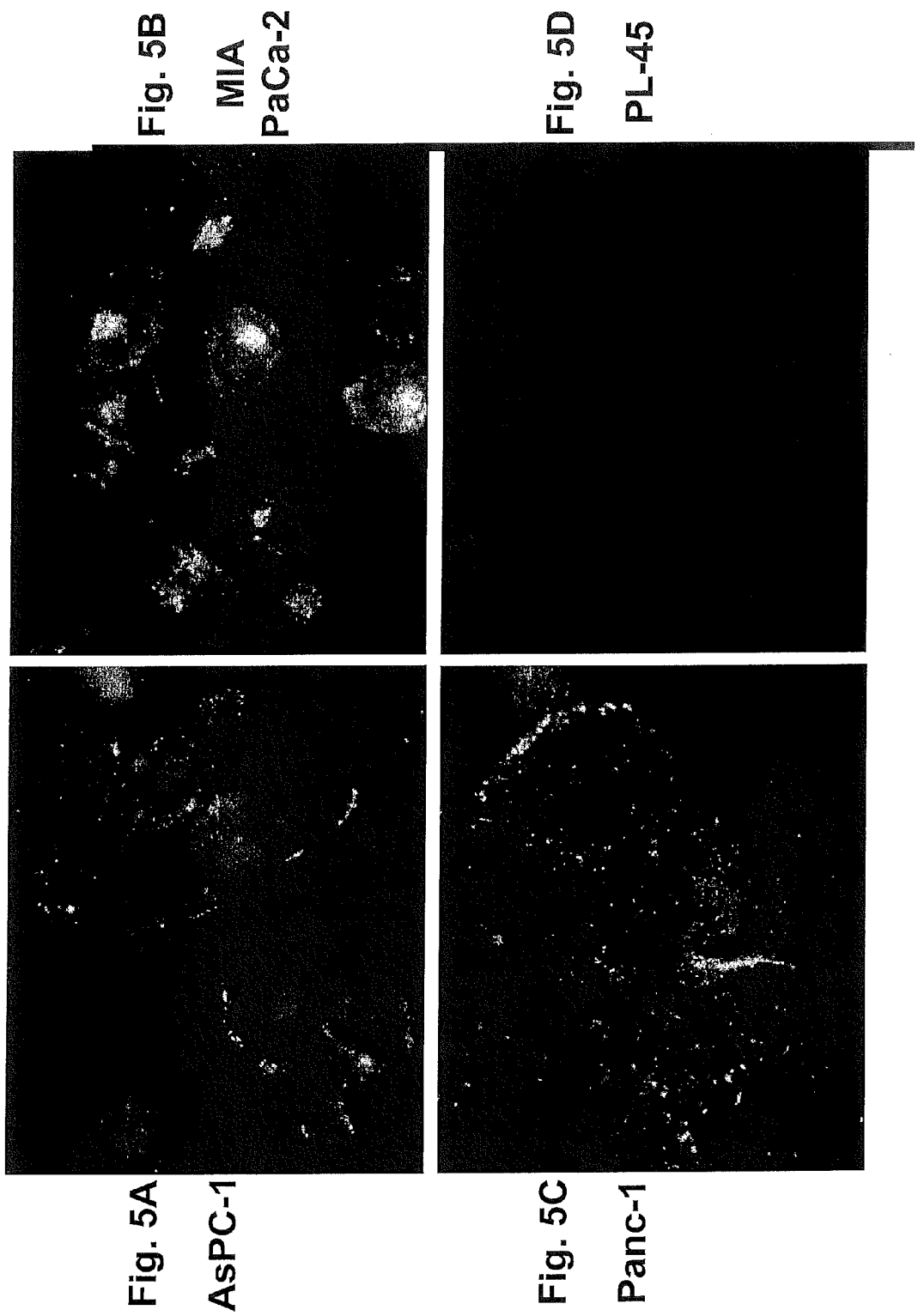

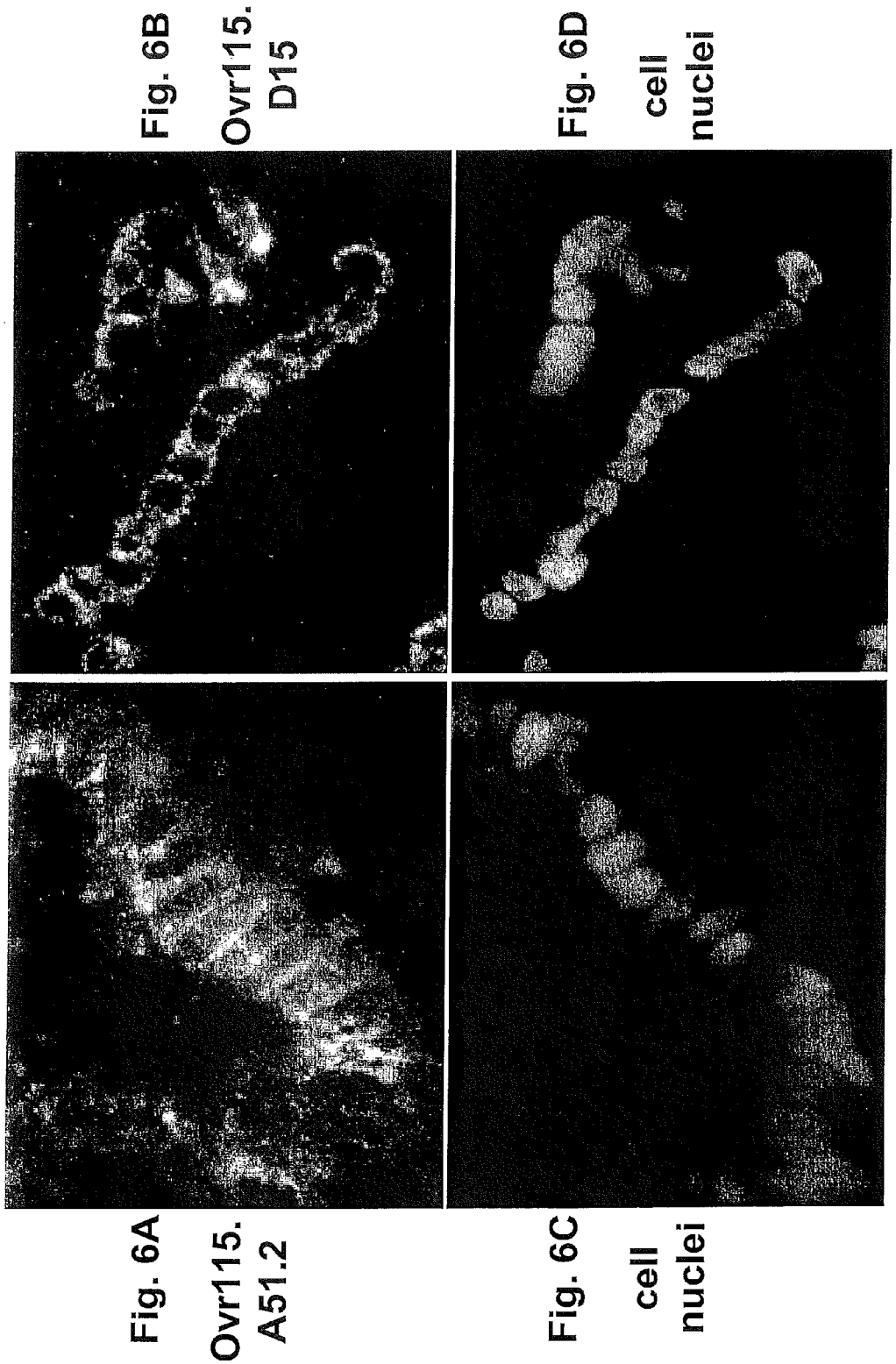
Figure 6: Localization of Ovr115 in ovarian cancer cells

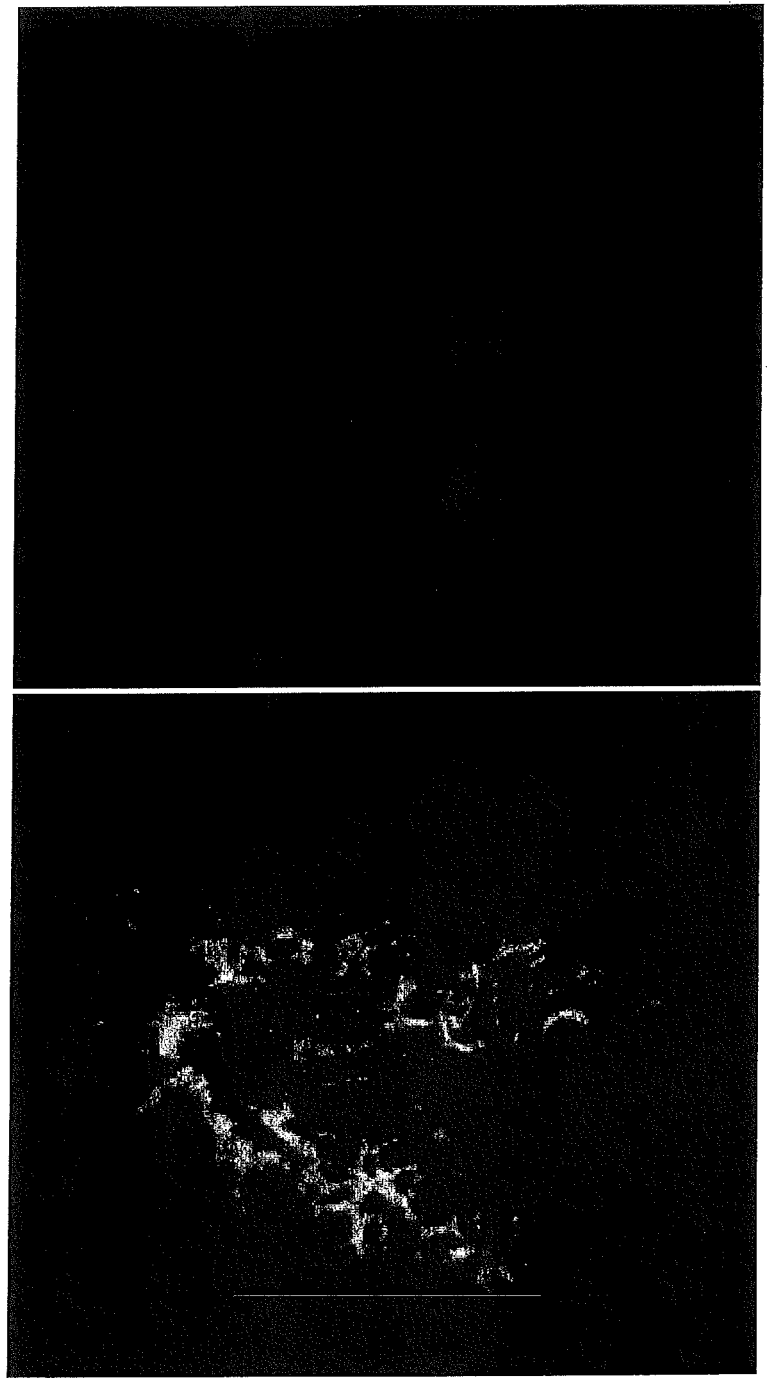
Figure 7: Localization of Ovr115 in ovarian cancer cells

Figure 8: OVR115.D84 labels epithelial cells in ovarian cancer tumors

Control IgG

Ovr115.D84

Figure 9: Ovr115.D84 labels epithelial cells in pancreatic cancer tumors

Control IgG

Ovr115.D84

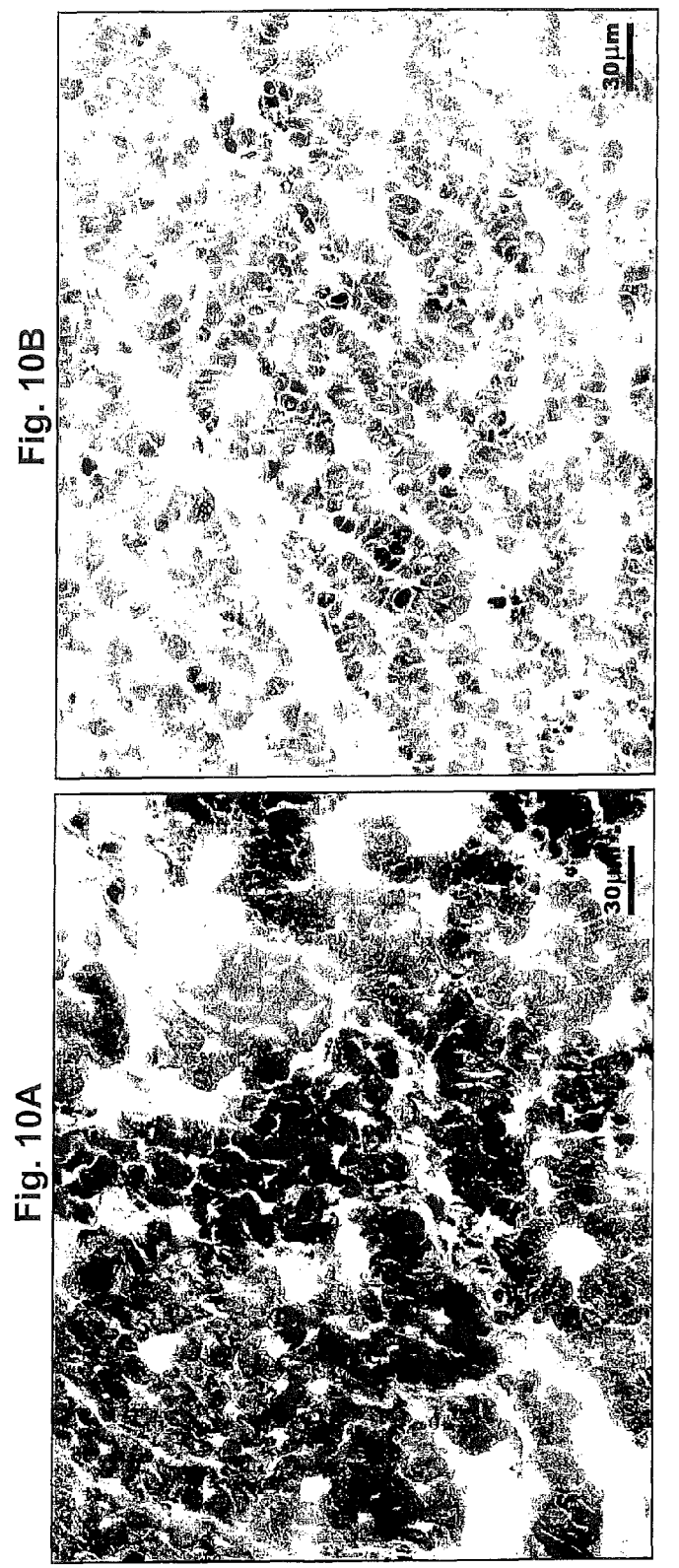
Figure 10: Ovarian Serous Papillary Adenocarcinoma, Unfixed OCT Frozen Sections immunolabeled with Ovr115.D43.1

Figure 11: Ovr115.F64.2 and Ovr115.D43.1 label colon adenocarcinoma cancer cells

Fig. 11A
Ovr115.F64.2 10ug/ml in frozen colon adenocarcinoma
Positive staining specifically in cancer cells

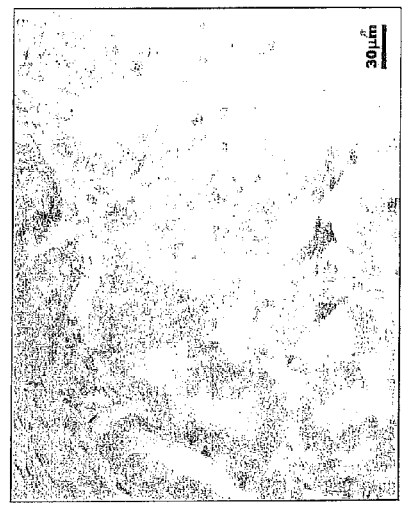

Fig. 11B
Mouse IgG1 10ug/ml in frozen colon adenocarcinoma
No staining in cancer cells

Fig. 11C
Ovr115.D43.1 5ug/ml in FFPE colon adenocarcinoma
Positive staining specifically in cancer cells

Fig. 11D
Mouse IgG1 10ug/ml in FFPE colon adenocarcinoma
No staining in cancer cells

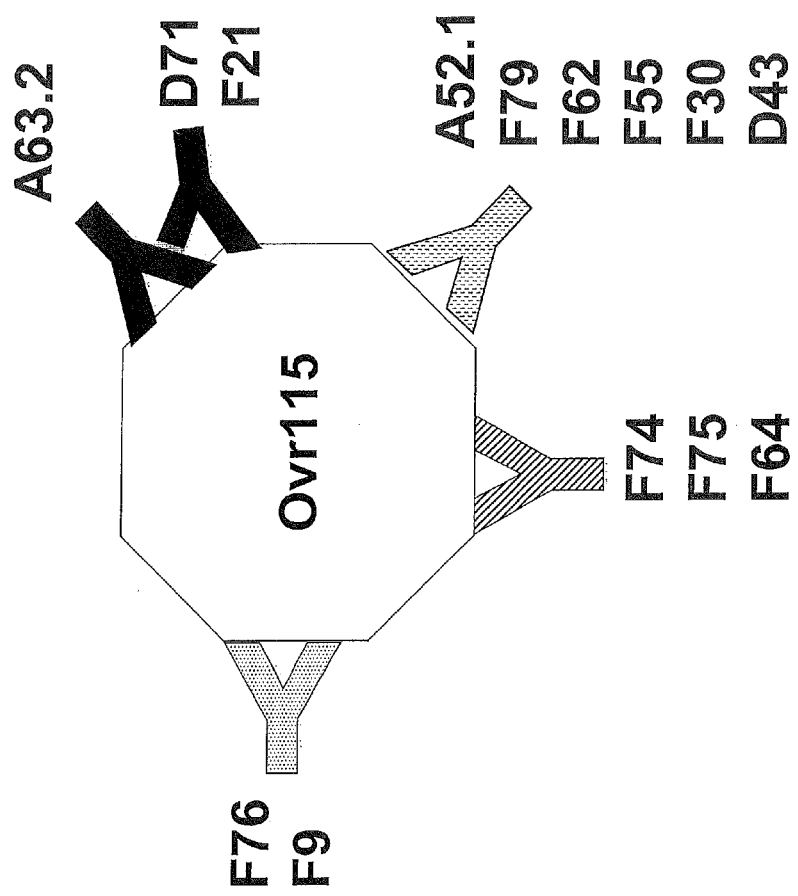
Figure 12: Epitope Map for Ovr115 MAbs

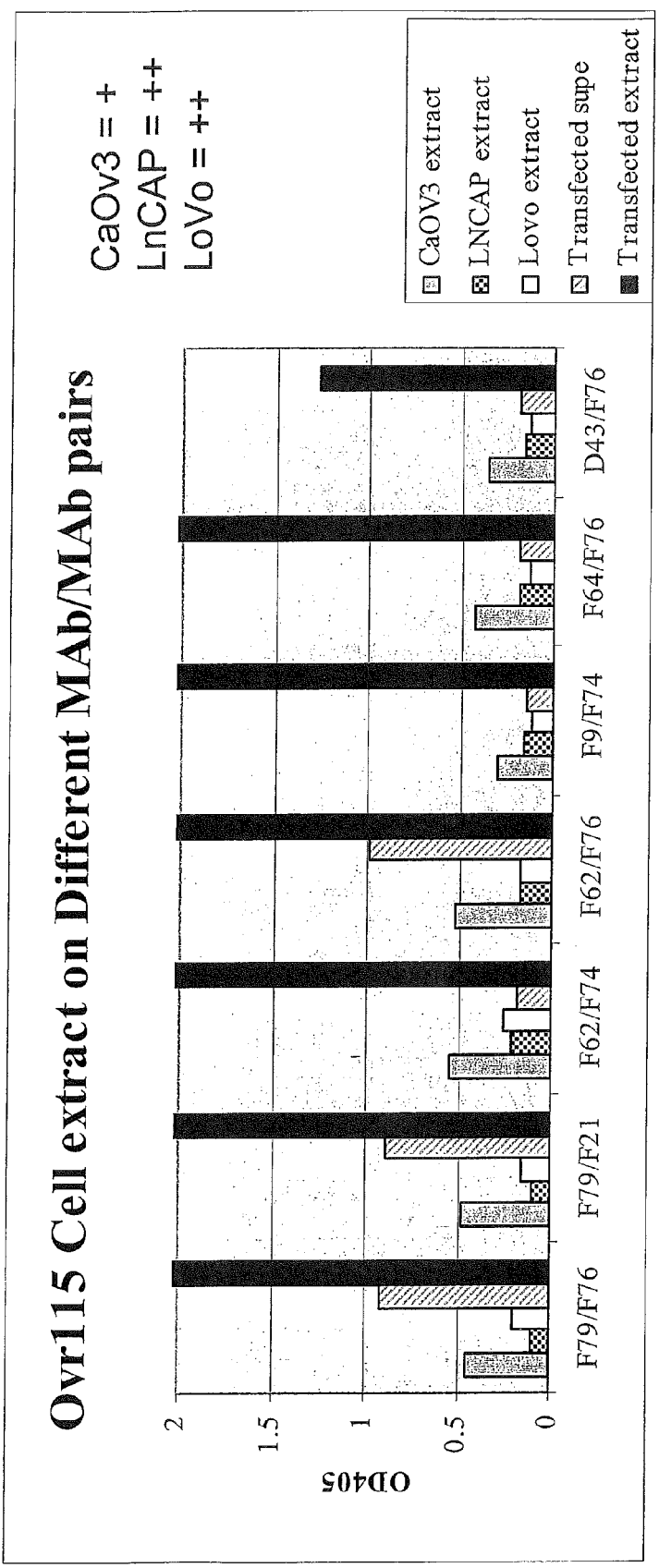
Figure 13: Sandwich ELISA detection of Ovr115 in tumor cell and transfected cell lysates using Ovr115.D43 & F-Series MAbs

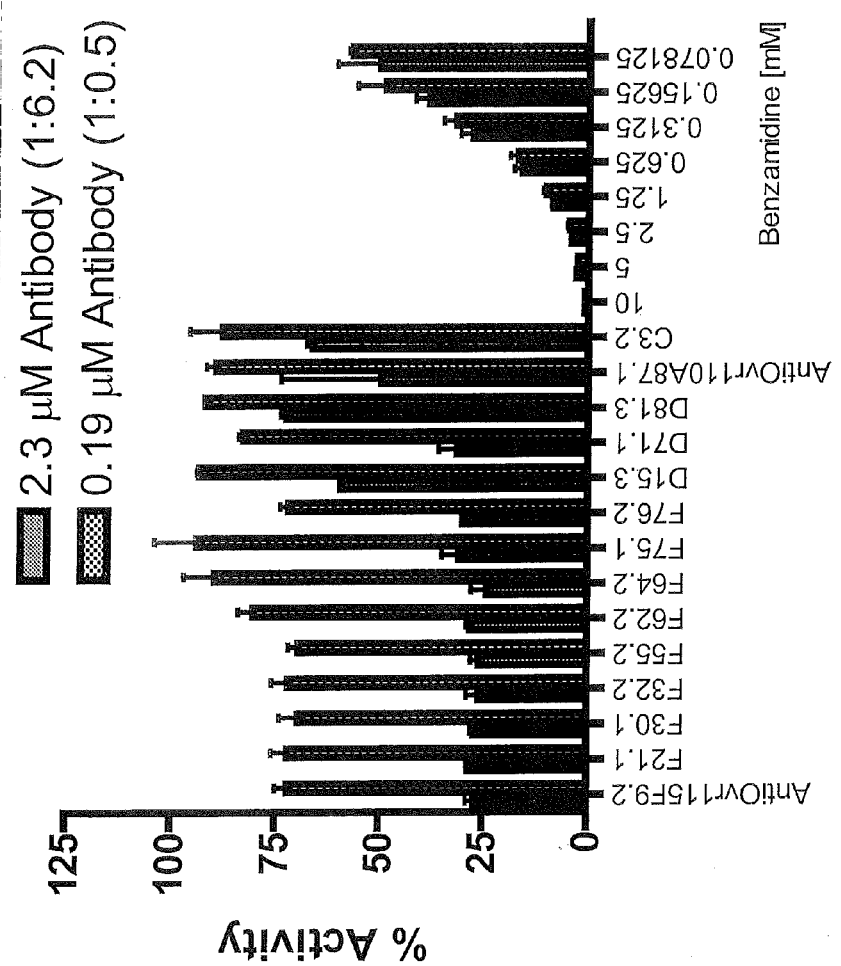
Figure 14: Anti-Ovr115 Activity Screening with Ovr115 MAbs

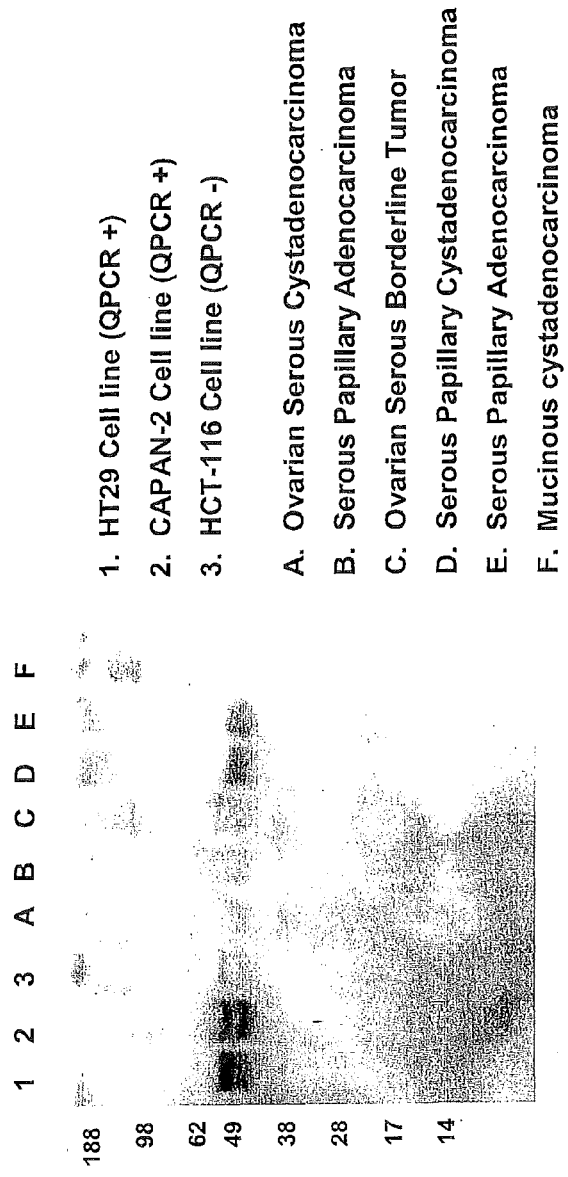
Figure 15. Ovr115 mAbs Recognize Native Ovr115 Protein in Human Cell Lines and Ovarian Tumors by Western Blot (mAb Ovr115.F21.1)

Figure 16. Transformation of Epithelial Cells by Overexpression of Ovr115
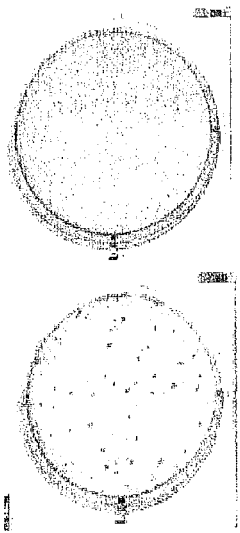
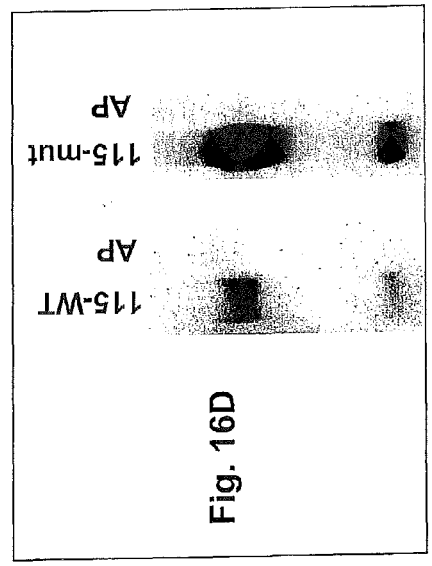
Fig. 16A
Produce AP control and target retrovirus using virus packaging cells → Infect target cells, G418 select → Plate expressing cells in soft agar
Fig. 16B
Ovr115 wild type | AP control | Ovr115 mutant
Fig. 16C
Fig. 16D

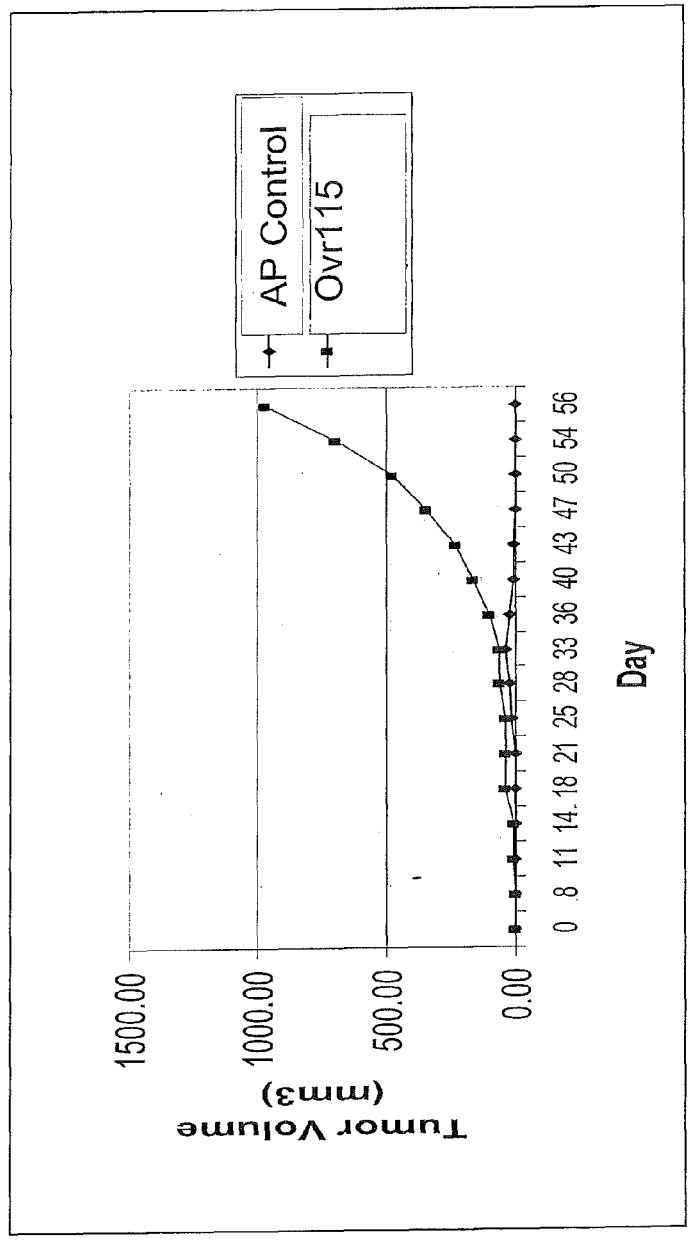
Figure 17. Overexpression of Ovr115 Induces SQ Tumor Growth in SCID Beige Mice
Cells in agar assay expressing Ovr115 or AP (Fig. 16) were used for tumor xenograft

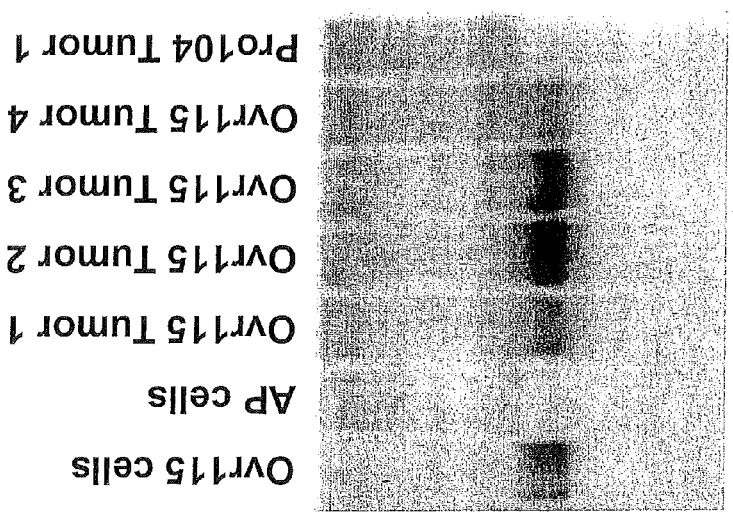
Figure 18. Expression of Ovr115 Protein from Tumor Xenografts

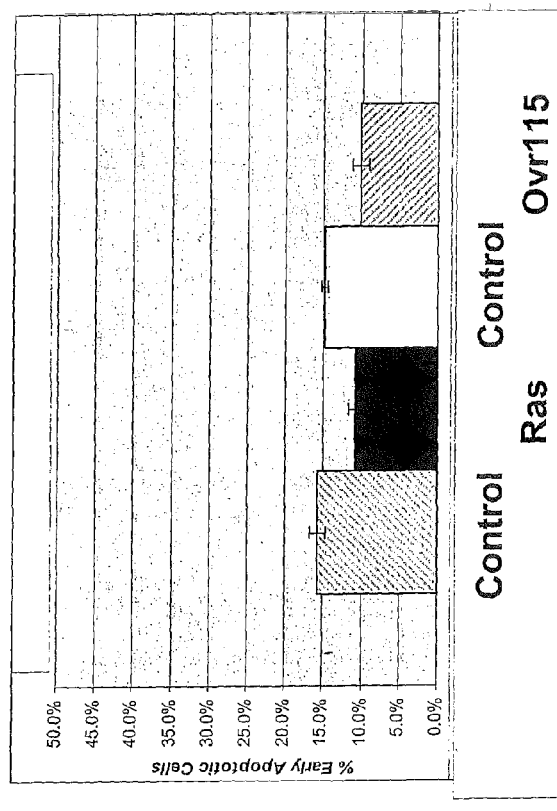
Figure 19. Overexpression of Ovr115 Protects RK3E Cells From Apoptosis This patent application claims priority to U.S. Provisional patent application Ser. No. 60/559,730 filed Apr. 5, 2004 and U.S. Provisional patent application Ser. No. 60/471,068, filed May 16, 2003, each of which is herein incorporated by reference in its entirety.

SEQUENCE LISTING

```
<160> NUMBER OF SEQ ID NOS: 5

<210> SEQ ID NO 1
<211> LENGTH: 486
<212> TYPE: PRT
<213> ORGANISM: Homo Sapien

<400> SEQUENCE: 1

Met Ala Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
        130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Val Pro Arg
        210                 215                 220

His Asn Gln Thr Ser Leu Tyr Lys Lys Ala Gly Phe Glu Asn Leu Tyr
225                 230                 235                 240

Phe Gln Gly Val Val Gly Gly Glu Glu Ala Ser Val Asp Ser Trp Pro
                245                 250                 255

Trp Gln Val Ser Ile Gln Tyr Asp Lys Gln His Val Cys Gly Gly Ser
            260                 265                 270

Ile Leu Asp Pro His Trp Val Leu Thr Ala Ala His Cys Phe Arg Lys
        275                 280                 285

His Thr Asp Val Phe Asn Trp Lys Val Arg Ala Gly Ser Asp Lys Leu
    290                 295                 300

Gly Ser Phe Pro Ser Leu Ala Val Ala Lys Ile Ile Ile Ile Glu Phe
```

```
                305                 310                 315                 320
Asn Pro Met Tyr Pro Lys Asp Asn Asp Ile Ala Leu Met Lys Leu Gln
                    325                 330                 335

Phe Pro Leu Thr Phe Ser Gly Thr Val Arg Pro Ile Cys Leu Pro Phe
                340                 345                 350

Phe Asp Glu Glu Leu Thr Pro Ala Thr Pro Leu Trp Ile Ile Gly Trp
            355                 360                 365

Gly Phe Thr Lys Gln Asn Gly Gly Lys Met Ser Asp Ile Leu Leu Gln
        370                 375                 380

Ala Ser Val Gln Val Ile Asp Ser Thr Arg Cys Asn Ala Asp Asp Ala
385                 390                 395                 400

Tyr Gln Gly Glu Val Thr Glu Lys Met Met Cys Ala Gly Ile Pro Glu
                405                 410                 415

Gly Gly Val Asp Thr Cys Gln Gly Asp Ser Gly Gly Pro Leu Met Tyr
                420                 425                 430

Gln Ser Asp Gln Trp His Val Val Gly Ile Val Ser Trp Gly Tyr Gly
            435                 440                 445

Cys Gly Gly Pro Ser Thr Pro Gly Val Tyr Thr Lys Val Ser Ala Tyr
        450                 455                 460

Leu Asn Trp Ile Tyr Asn Val Trp Lys Ala Glu Leu Ser Asn Trp Ser
465                 470                 475                 480

His Pro Gln Phe Glu Lys
                485

<210> SEQ ID NO 2
<211> LENGTH: 391
<212> TYPE: PRT
<213> ORGANISM: Artificial sequence
<220> FEATURE:
<223> OTHER INFORMATION: Synthetic

<400> SEQUENCE: 2

Met Lys Val Ile Leu Asp Lys Tyr Tyr Phe Leu Cys Gly Gln Pro Leu
1               5                   10                  15

His Phe Ile Pro Arg Lys Gln Leu Cys Asp Gly Glu Leu Asp Cys Pro
                20                  25                  30

Leu Gly Glu Asp Glu His Cys Val Lys Ser Phe Pro Glu Gly Pro
            35                  40                  45

Ala Val Ala Val Arg Leu Ser Lys Asp Arg Ser Thr Leu Gln Val Leu
        50                  55                  60

Asp Ser Ala Thr Gly Asn Trp Phe Ser Ala Cys Phe Asp Asn Phe Thr
65                  70                  75                  80

Glu Ala Leu Ala Glu Thr Ala Cys Arg Gln Met Gly Tyr Ser Ser Lys
                85                  90                  95

Pro Thr Phe Arg Ala Val Glu Ile Gly Pro Asp Gln Asp Leu Asp Val
                100                 105                 110

Val Glu Ile Thr Glu Asn Ser Gln Glu Leu Arg Met Arg Asn Ser Ser
            115                 120                 125

Gly Pro Cys Leu Ser Gly Ser Leu Val Ser Leu His Cys Leu Ala Cys
        130                 135                 140

Gly Lys Ser Leu Lys Thr Pro Arg Val Val Gly Gly Glu Glu Ala Ser
145                 150                 155                 160

Val Asp Ser Trp Pro Trp Gln Val Ser Ile Gln Tyr Asp Lys Gln His
                165                 170                 175

Val Cys Gly Gly Ser Ile Leu Asp Pro His Trp Val Leu Thr Ala Ala
                180                 185                 190
```

```
His Cys Phe Arg Lys His Thr Asp Val Phe Asn Trp Lys Val Arg Ala
            195                 200                 205

Gly Ser Asp Lys Leu Gly Ser Phe Pro Ser Leu Ala Val Ala Lys Ile
        210                 215                 220

Ile Ile Ile Glu Phe Asn Pro Met Tyr Pro Lys Asp Asn Asp Ile Ala
225                 230                 235                 240

Leu Met Lys Leu Gln Phe Pro Leu Thr Phe Ser Gly Thr Val Arg Pro
                245                 250                 255

Ile Cys Leu Pro Phe Phe Asp Glu Glu Leu Thr Pro Ala Thr Pro Leu
                260                 265                 270

Trp Ile Ile Gly Trp Gly Phe Thr Lys Gln Asn Gly Gly Lys Met Ser
            275                 280                 285

Asp Ile Leu Leu Gln Ala Ser Val Gln Val Ile Asp Ser Thr Arg Cys
        290                 295                 300

Asn Ala Asp Asp Ala Tyr Gln Gly Glu Val Thr Glu Lys Met Met Cys
305                 310                 315                 320

Ala Gly Ile Pro Glu Gly Gly Val Asp Thr Cys Gln Gly Asp Ser Gly
                325                 330                 335

Gly Pro Leu Met Tyr Gln Ser Asp Gln Trp His Val Val Gly Ile Val
                340                 345                 350

Ser Trp Gly Tyr Gly Cys Gly Gly Pro Ser Thr Pro Gly Val Tyr Thr
            355                 360                 365

Lys Val Ser Ala Tyr Leu Asn Trp Ile Tyr Asn Val Trp Lys Ala Glu
        370                 375                 380

Leu His His His His His His
385                 390

<210> SEQ ID NO 3
<211> LENGTH: 461
<212> TYPE: PRT
<213> ORGANISM: Artificial sequence
<220> FEATURE:
<223> OTHER INFORMATION: Synthetic

<400> SEQUENCE: 3

Met Asp Pro Asp Ser Asp Gln Pro Leu Asn Ser Leu Asp Val Lys Pro
1               5                   10                  15

Leu Arg Lys Pro Arg Ile Pro Met Glu Thr Phe Arg Lys Val Gly Ile
                20                  25                  30

Pro Ile Ile Ile Ala Leu Leu Ser Leu Ala Ser Ile Ile Val Val Val
            35                  40                  45

Val Leu Ile Lys Val Ile Leu Asp Lys Tyr Tyr Phe Leu Cys Gly Gln
50                  55                  60

Pro Leu His Phe Ile Pro Arg Lys Gln Leu Cys Asp Gly Glu Leu Asp
65                  70                  75                  80

Cys Pro Leu Gly Glu Asp Glu Glu His Cys Val Lys Ser Phe Pro Glu
                85                  90                  95

Gly Pro Ala Val Ala Val Arg Leu Ser Lys Asp Arg Ser Thr Leu Gln
            100                 105                 110

Val Leu Asp Ser Ala Thr Gly Asn Trp Phe Ser Ala Cys Phe Asp Asn
        115                 120                 125

Phe Thr Glu Ala Leu Ala Glu Thr Ala Cys Arg Gln Met Gly Tyr Ser
    130                 135                 140

Ser Lys Pro Thr Phe Arg Ala Val Glu Ile Gly Pro Asp Gln Asp Leu
145                 150                 155                 160
```

```
Asp Val Val Glu Ile Thr Glu Asn Ser Gln Glu Leu Arg Met Arg Asn
                165                 170                 175

Ser Ser Gly Pro Cys Leu Ser Gly Ser Leu Val Ser Leu His Cys Leu
            180                 185                 190

Ala Cys Gly Lys Ser Leu Lys Thr Pro Arg Val Val Gly Gly Glu Glu
        195                 200                 205

Ala Ser Val Asp Ser Trp Pro Trp Gln Val Ser Ile Gln Tyr Asp Lys
    210                 215                 220

Gln His Val Cys Gly Gly Ser Ile Leu Asp Pro His Trp Val Leu Thr
225                 230                 235                 240

Ala Ala His Cys Phe Arg Lys His Thr Asp Val Phe Asn Trp Lys Val
                245                 250                 255

Arg Ala Gly Ser Asp Lys Leu Gly Ser Phe Pro Ser Leu Ala Val Ala
            260                 265                 270

Lys Ile Ile Ile Ile Glu Phe Asn Pro Met Tyr Pro Lys Asp Asn Asp
        275                 280                 285

Ile Ala Leu Met Lys Leu Gln Phe Pro Leu Thr Phe Ser Gly Thr Val
    290                 295                 300

Arg Pro Ile Cys Leu Pro Phe Phe Asp Glu Glu Leu Thr Pro Ala Thr
305                 310                 315                 320

Pro Leu Trp Ile Ile Gly Trp Gly Phe Thr Lys Gln Asn Gly Gly Lys
                325                 330                 335

Met Ser Asp Ile Leu Leu Gln Ala Ser Val Gln Val Ile Asp Ser Thr
            340                 345                 350

Arg Cys Asn Ala Asp Asp Ala Tyr Gln Gly Val Thr Glu Lys Met
        355                 360                 365

Met Cys Ala Gly Ile Pro Glu Gly Gly Val Asp Thr Cys Gln Gly Asp
    370                 375                 380

Ser Gly Gly Pro Leu Met Tyr Gln Ser Asp Gln Trp His Val Val Gly
385                 390                 395                 400

Ile Val Ser Trp Gly Tyr Gly Cys Gly Gly Pro Ser Thr Pro Gly Val
                405                 410                 415

Tyr Thr Lys Val Ser Ala Tyr Leu Asn Trp Ile Tyr Asn Val Trp Lys
            420                 425                 430

Ala Glu Leu Asp Pro Ala Phe Leu Tyr Lys Val Val Arg Ser Arg Met
        435                 440                 445

Ala Ser Tyr Pro Tyr Asp Val Pro Asp Tyr Ala Ser Leu
    450                 455                 460

<210> SEQ ID NO 4
<211> LENGTH: 287
<212> TYPE: PRT
<213> ORGANISM: Artificial sequence
<220> FEATURE:
<223> OTHER INFORMATION: Synthetic

<400> SEQUENCE: 4

Met Lys Phe Leu Val Asn Val Ala Leu Val Phe Met Val Val Tyr Ile
1               5                   10                  15

Ser Tyr Ile Tyr Ala Asp Pro Met Ala Ile Val Gly Gly Glu Asp Ala
            20                  25                  30

Glu Leu Gly Arg Trp Pro Trp Gln Gly Ser Leu Arg Leu Trp Asp Ser
        35                  40                  45

His Val Cys Gly Val Ser Leu Leu Ser His Arg Trp Ala Leu Thr Ala
    50                  55                  60

Ala His Cys Phe Glu Thr Tyr Ser Asp Leu Ser Asp Pro Ser Gly Trp
```

```
                65                  70                  75                  80
Met Val Gln Phe Gly Gln Leu Thr Ser Met Pro Ser Phe Trp Ser Leu
                    85                  90                  95

Gln Ala Tyr Tyr Thr Arg Tyr Phe Val Ser Asn Ile Tyr Leu Ser Pro
                    100                 105                 110

Arg Tyr Leu Gly Asn Ser Pro Tyr Asp Ile Ala Leu Val Lys Leu Ser
                    115                 120                 125

Ala Pro Val Thr Tyr Thr Lys His Ile Gln Pro Ile Cys Leu Gln Ala
                    130                 135                 140

Ser Thr Phe Glu Phe Glu Asn Arg Thr Asp Cys Trp Val Thr Gly Trp
145                 150                 155                 160

Gly Tyr Ile Lys Glu Asp Glu Ala Leu Pro Ser Pro His Thr Leu Gln
                    165                 170                 175

Glu Val Gln Val Ala Ile Ile Asn Asn Ser Met Cys Asn His Leu Phe
                    180                 185                 190

Leu Lys Tyr Ser Phe Arg Lys Asp Ile Phe Gly Asp Met Val Cys Ala
                    195                 200                 205

Gly Asn Ala Gln Gly Gly Lys Asp Ala Cys Phe Gly Asp Ser Gly Gly
                    210                 215                 220

Pro Leu Ala Cys Asn Lys Asn Gly Leu Trp Tyr Gln Ile Gly Val Val
225                 230                 235                 240

Ser Trp Gly Val Gly Cys Gly Arg Pro Asn Arg Pro Gly Val Tyr Thr
                    245                 250                 255

Asn Ile Ser His His Phe Glu Trp Ile Gln Lys Leu Met Ala Gln Ser
                    260                 265                 270

Gly Met Ser Gln Pro Asp Pro Ser Trp His His His His His His
                    275                 280                 285

<210> SEQ ID NO 5
<211> LENGTH: 340
<212> TYPE: PRT
<213> ORGANISM: Artificial sequence
<220> FEATURE:
<223> OTHER INFORMATION: Synthetic

<400> SEQUENCE: 5

Met Gly Ala Arg Gly Ala Leu Leu Leu Ala Leu Leu Leu Ala Arg Ala
1               5                   10                  15

Gly Leu Arg Lys Pro Glu Ser Gln Glu Ala Ala Pro Leu Ser Gly Pro
                    20                  25                  30

Cys Gly Arg Arg Val Ile Thr Ser Arg Ile Val Gly Gly Glu Asp Ala
                    35                  40                  45

Glu Leu Gly Arg Trp Pro Trp Gln Gly Ser Leu Arg Leu Trp Asp Ser
                    50                  55                  60

His Val Cys Gly Val Ser Leu Leu Ser His Arg Trp Ala Leu Thr Ala
65                  70                  75                  80

Ala His Cys Phe Glu Thr Tyr Ser Asp Leu Ser Asp Pro Ser Gly Trp
                    85                  90                  95

Met Val Gln Phe Gly Gln Leu Thr Ser Met Pro Ser Phe Trp Ser Leu
                    100                 105                 110

Gln Ala Tyr Tyr Thr Arg Tyr Phe Val Ser Asn Ile Tyr Leu Ser Pro
                    115                 120                 125

Arg Tyr Leu Gly Asn Ser Pro Tyr Asp Ile Ala Leu Val Lys Leu Ser
                    130                 135                 140

Ala Pro Val Thr Tyr Thr Lys His Ile Gln Pro Ile Cys Leu Gln Ala
145                 150                 155                 160
```

```
Ser Thr Phe Glu Phe Glu Asn Arg Thr Asp Cys Trp Val Thr Gly Trp
            165                 170                 175

Gly Tyr Ile Lys Glu Asp Glu Ala Leu Pro Ser Pro His Thr Leu Gln
            180                 185                 190

Glu Val Gln Val Ala Ile Ile Asn Asn Ser Met Cys Asn His Leu Phe
        195                 200                 205

Leu Lys Tyr Ser Phe Arg Lys Asp Ile Phe Gly Asp Met Val Cys Ala
        210                 215                 220

Gly Asn Ala Gln Gly Gly Lys Asp Ala Cys Phe Gly Asp Ser Gly Gly
225                 230                 235                 240

Pro Leu Ala Cys Asn Lys Asn Gly Leu Trp Tyr Gln Ile Gly Val Val
            245                 250                 255

Ser Trp Gly Val Gly Cys Gly Arg Pro Asn Arg Pro Gly Val Tyr Thr
            260                 265                 270

Asn Ile Ser His His Phe Glu Trp Ile Gln Lys Leu Met Ala Gln Ser
            275                 280                 285

Gly Met Ser Gln Pro Asp Pro Ser Trp Pro Leu Leu Phe Phe Pro Leu
        290                 295                 300

Leu Trp Ala Leu Pro Leu Leu Gly Pro Val Asp Pro Ala Phe Leu Tyr
305                 310                 315                 320

Lys Val Val Arg Ser Arg Met Ala Ser Tyr Pro Tyr Asp Val Pro Asp
            325                 330                 335

Tyr Ala Ser Leu
            340
```

OVR115 ANTIBODY COMPOSITIONS AND METHODS OF USE

FIELD OF THE INVENTION

The present invention relates to anti-Ovr115 antibody compositions and methods of killing Ovr115-expressing ovarian, pancreatic and colon cancers cells.

BACKGROUND OF THE INVENTION

Ovarian Cancer

Cancer of the ovaries is the fourth-most common cause of cancer death in women in the United States, with more than 23,000 new cases and roughly 14,000 deaths predicted for the year 2001. Shridhar, V. et al., *Cancer Res.* 61(15): 5895-904 (2001); Memarzadeh, S. & Berek, J. S., *J. Reprod. Med.* 46(7): 621-29 (2001). The American Cancer Society estimates that there will be about 25,580 new cases of ovarian cancer in 2004 in the United States alone. Ovarian cancer will cause about 16,090 deaths in the United States in the same year. ACS Website: cancer with the extention .org of the world wide web. The incidence of ovarian cancer is of serious concern worldwide, with an estimated 191,000 new cases predicted annually. Runnebaum, I. B. & Stickeler, E., *J. Cancer Res. Clin. Oncol.* 127(2): 73-79 (2001). Unfortunately, women with ovarian cancer are typically asymptomatic until the disease has metastasized. Because effective screening for ovarian cancer is not available, roughly 70% of women diagnosed have an advanced stage of the cancer with a five-year survival rate of ~25-30%. Memarzadeh, S. & Berek, J. S., supra; Nunns, D. et al., *Obstet. Gynecol. Surv.* 55(12): 746-51. Conversely, women diagnosed with early stage ovarian cancer enjoy considerably higher survival rates. Werness, B. A. & Eltabbakh, G. H., *Int'l. J. Gynecol. Pathol.* 20(1): 48-63 (2001). Although our understanding of the etiology of ovarian cancer is incomplete, the results of extensive research in this area point to a combination of age, genetics, reproductive, and dietary/environmental factors. Age is a key risk factor in the development of ovarian cancer: while the risk for developing ovarian cancer before the age of 30 is slim, the incidence of ovarian cancer rises linearly between ages 30 to 50, increasing at a slower rate thereafter, with the highest incidence being among septagenarian women. Jeanne M. Schilder et al., *Hereditary Ovarian Cancer: Clinical Syndromes and Management*, in *Ovarian Cancer* 182 (Stephen C. Rubin & Gregory P. Sutton eds., 2d ed. 2001).

With respect to genetic factors, a family history of ovarian cancer is the most significant risk factor in the development of the disease, with that risk depending on the number of affected family members, the degree of their relationship to the woman, and which particular first degree relatives are affected by the disease. Id. Mutations in several genes have been associated with ovarian cancer, including BRCA1 and BRCA2, both of which play a key role in the development of breast cancer, as well as hMSH2 and hMLH1, both of which are associated with hereditary non-polyposis colon cancer. Katherine Y. Look, *Epidemiology, Etiology, and Screening of Ovarian Cancer*, in *Ovarian Cancer* 169, 171-73 (Stephen C. Rubin & Gregory P. Sutton eds., 2d ed. 2001). BRCA1, located on chromosome 17, and BRCA2, located on chromosome 13, are tumor suppressor genes implicated in DNA repair; mutations in these genes are linked to roughly 10% of ovarian cancers. Id. at 171-72; Schilder et al., supra at 185-86. hMSH2 and hMLH1 are associated with DNA mismatch repair, and are located on chromosomes 2 and 3, respectively; it has been reported that roughly 3% of hereditary ovarian carcinomas are due to mutations in these genes. Look, supra at 173; Schilder et al., supra at 184, 188-89.

Reproductive factors have also been associated with an increased or reduced risk of ovarian cancer. Late menopause, nulliparity, and early age at menarche have all been linked with an elevated risk of ovarian cancer. Schilder et al., supra at 182. One theory hypothesizes that these factors increase the number of ovulatory cycles over the course of a woman's life, leading to "incessant ovulation," which is thought to be the primary cause of mutations to the ovarian epithelium. Id.; Laura J. Havrilesky & Andrew Berchuck, *Molecular Alterations in Sporadic Ovarian Cancer*, in *Ovarian Cancer* 25 (Stephen C. Rubin & Gregory P. Sutton eds., 2d ed. 2001). The mutations may be explained by the fact that ovulation results in the destruction and repair of that epithelium, necessitating increased cell division, thereby increasing the possibility that an undetected mutation will occur. Id. Support for this theory may be found in the fact pregnancy, lactation, and the use of oral contraceptives, all of which suppress ovulation, confer a protective effect with respect to developing ovarian cancer. Id.

Among dietary/environmental factors, there would appear to be an association between high intake of animal fat or red meat and ovarian cancer, while the antioxidant Vitamin A, which prevents free radical formation and also assists in maintaining normal cellular differentiation, may offer a protective effect. Look, supra at 169. Reports have also associated asbestos and hydrous magnesium trisilicate (talc), the latter of which may be present in diaphragms and sanitary napkins. Id. at 169-70.

Current screening procedures for ovarian cancer, while of some utility, are quite limited in their diagnostic ability, a problem that is particularly acute at early stages of cancer progression when the disease is typically asymptomatic yet is most readily treated. Walter J. Burdette, *Cancer: Etiology, Diagnosis, and Treatment* 166 (1998); Memarzadeh & Berek, supra; Runnebaum & Stickeler, supra; Werness & Eltabbakh, supra. Commonly used screening tests include biannual rectovaginal pelvic examination, radioimmunoassay to detect the CA-125 serum tumor marker, and transvaginal ultrasonography. Burdette, supra at 166.

Pelvic examination has failed to yield adequate numbers of early diagnoses, and the other methods are not sufficiently accurate. Id. One study reported that only 15% of patients who suffered from ovarian cancer were diagnosed with the disease at the time of their pelvic examination. Look, supra at 174. Moreover, the CA-125 test is prone to giving false positives in pre-menopausal women and has been reported to be of low predictive value in post-menopausal women. Id. at 174-75. Although transvaginal ultrasonography is now the preferred procedure for screening for ovarian cancer, it is unable to distinguish reliably between benign and malignant tumors, and also cannot locate primary peritoneal malignancies or ovarian cancer if the ovary size is normal. Schilder et al., supra at 194-95. While genetic testing for mutations of the BRCA1, BRCA2, hMSH2, and hMLH1 genes is now available, these tests may be too costly for some patients and may also yield false negative or indeterminate results. Schilder et al., supra at 191-94.

Other markers of interest are HE4 and mesothelin, see Urban et al. Ovarian cancer screening Hematol Oncol Clin North Am. 2003 August; 17(4):989-1005; Hellstrom et al. *The HE4 (WFDC2) protein is a biomarker for ovarian carcinoma*, Cancer Res. 2003 Jul. 1; 63(13):3695-700; Ordonez, *Application of mesothelin immunostaining in tumor diagnosis*, Am J Surg Pathol. 2003 November; 27(11):1418-28.

The staging of ovarian cancer, which is accomplished through surgical exploration, is crucial in determining the course of treatment and management of the disease. *AJCC Cancer Staging Handbook* 187 (Irvin D. Fleming et al. eds., 5th ed. 1998); Burdette, supra at 170; Memarzadeh & Berek, supra; Shridhar et al., supra. Staging is performed by reference to the classification system developed by the International Federation of Gynecology and Obstetrics. David H. Moore, *Primary Surgical Management of Early Epithelial Ovarian Carcinoma*, in *Ovarian Cancer* 203 (Stephen C. Rubin & Gregory P. Sutton eds., 2d ed. 2001); Fleming et al. eds., supra at 188. Stage I ovarian cancer is characterized by tumor growth that is limited to the ovaries and is comprised of three substages. Id. In substage IA, tumor growth is limited to one ovary, there is no tumor on the external surface of the ovary, the ovarian capsule is intact, and no malignant cells are present in ascites or peritoneal washings. Id. Substage IB is identical to A1, except that tumor growth is limited to both ovaries. Id. Substage IC refers to the presence of tumor growth limited to one or both ovaries, and also includes one or more of the following characteristics: capsule rupture, tumor growth on the surface of one or both ovaries, and malignant cells present in ascites or peritoneal washings. Id.

Stage II ovarian cancer refers to tumor growth involving one or both ovaries, along with pelvic extension. Id. Substage IIA involves extension and/or implants on the uterus and/or fallopian tubes, with no malignant cells in the ascites or peritoneal washings, while substage IIB involves extension into other pelvic organs and tissues, again with no malignant cells in the ascites or peritoneal washings. Id. Substage IIC involves pelvic extension as in IIA or IIB, but with malignant cells in the ascites or peritoneal washings. Id.

Stage III ovarian cancer involves tumor growth in one or both ovaries, with peritoneal metastasis beyond the pelvis confirmed by microscope and/or metastasis in the regional lymph nodes. Id. Substage IIIA is characterized by microscopic peritoneal metastasis outside the pelvis, with substage IIIB involving macroscopic peritoneal metastasis outside the pelvis 2 cm or less in greatest dimension. Id. Substage IIIC is identical to IIIB, except that the metastasis is greater than 2 cm in greatest dimension and may include regional lymph node metastasis. Id. Lastly, Stage IV refers to the presence distant metastasis, excluding peritoneal metastasis. Id.

While surgical staging is currently the benchmark for assessing the management and treatment of ovarian cancer, it suffers from considerable drawbacks, including the invasiveness of the procedure, the potential for complications, as well as the potential for inaccuracy. Moore, supra at 206-208, 213. In view of these limitations, attention has turned to developing alternative staging methodologies through understanding differential gene expression in various stages of ovarian cancer and by obtaining various biomarkers to help better assess the progression of the disease. Vartiainen, J. et al., *Int'l J. Cancer*, 95(5): 313-16 (2001); Shridhar et al. supra; Baekelandt, M. et al., *J. Clin. Oncol.* 18(22): 3775-81.

The treatment of ovarian cancer typically involves a multiprong attack, with surgical intervention serving as the foundation of treatment. Dennis S. Chi & William J. Hoskins, *Primary Surgical Management of Advanced Epithelial Ovarian Cancer*, in *Ovarian Cancer* 241 (Stephen C. Rubin & Gregory P. Sutton eds., 2d ed. 2001). For example, in the case of epithelial ovarian cancer, which accounts for ~90% of cases of ovarian cancer, treatment typically consists of: (1) cytoreductive surgery, including total abdominal hysterectomy, bilateral salpingo-oophorectomy, omentectomy, and lymphadenectomy, followed by (2) adjuvant chemotherapy with paclitaxel and either cisplatin or carboplatin. Eltabbakh, G. H. & Awtrey, C. S., *Expert Op. Pharmacother.* 2(10): 109-24. Despite a clinical response rate of 80% to the adjuvant therapy, most patients experience tumor recurrence within three years of treatment. Id. Certain patients may undergo a second cytoreductive surgery and/or second-line chemotherapy. Memarzadeh & Berek, supra.

From the foregoing, it is clear that procedures used for detecting, diagnosing, monitoring, staging, prognosticating, and preventing the recurrence of ovarian cancer are of critical importance to the outcome of the patient. Moreover, current procedures, while helpful in each of these analyses, are limited by their specificity, sensitivity, invasiveness, and/or their cost. As such, highly specific and sensitive procedures that would operate by way of detecting novel markers in cells, tissues, or bodily fluids, with minimal invasiveness and at a reasonable cost, would be highly desirable.

Accordingly, there is a great need for more sensitive and accurate methods for predicting whether a person is likely to develop ovarian cancer, for diagnosing ovarian cancer, for monitoring the progression of the disease, for staging the ovarian cancer, for determining whether the ovarian cancer has metastasized, for imaging the ovarian cancer and for better treatment of ovarian cancer.

Pancreatic Cancer

Pancreatic cancer is the thirteenth-most common cancer and eighth-most cause of cancer death worldwide. Donghui Li, *Molecular Epidemiology*, in *Pancreatic Cancer* 3 (Douglas B. Evans et al. eds., 2002). In the United States, cancer of the pancreas is the fourth-most common cancer in both males and females, accounting for five percent of cancer deaths and nearly 30,000 deaths overall. Id. The rates of pancreatic cancer are higher in men than women and higher in African-Americans as opposed to Caucasians. Id. at 9. The most significant predictor of pancreatic cancer is patient age; among Caucasians, the age-related incidence of pancreatic cancer increases continuously, even through the 85 and older category. Id. at 3. Approximately 80% of cases occur in the age range of 60 to 80, with those in their 80s experiencing a risk of acquiring the disease 40 times that of those in their 40s. Id. Furthermore, the American Cancer Society estimates that there will be about 31,800 new cases of pancreatic cancer in 2004 in the United States alone. Pancreatic cancer will cause about 31,200 deaths in the United States in the same year. ACS Website: cancer with the extension .org of the world wide web. Despite the efforts of researchers and physicians in devising treatments for pancreatic cancer, it remains almost universally fatal. James R. Howe, *Molecular Markers as a Tool for the Early Diagnosis of pancreatic Cancer*, in *Pancreatic Cancer* 29 (Douglas B. Evans et al. eds., 2002).

Aside from age, a number of risk factors for pancreatic cancer have been identified, including smoking, diet, occupation, certain medical conditions, heredity, and molecular biologic. Smoking is the most important risk factor for acquiring the disease, with the link between smoking and pancreatic cancer being established in numerous studies. Li, supra at 3. The relative risk amounts to at least 1.5, increasing with the level of smoking to an outer risk ratio of 10-fold. Id. The next most important factor would appear to be diet, with increased risk associated with animal protein and fat intake, and decreased risk associated with intake of fruits and vegetables. Id. at 3-4. As for particular occupations, excessive rates of pancreatic cancer have been associated with workers in chemistry, coal and gas exploration, the metal industry, leather tanning, textiles, aluminum milling, and transportation. Id. at 4. A number of medical conditions have also been associated with an increased incidence of pancreatic cancer, including diabetes, chronic pancreatitis, gastrectomy, and cholecystectomy, although the cause and effect relationship between these conditions and pancreatic cancer has not been established. Id.

Hereditary genetic factors comprise less than 10% of the pancreatic cancer burden, with associations documented with hereditary pancreatitis, as well as germline mutations in familial cancer syndrome genes such as hMSH2 and hMLH1 (hereditary nonpolyposis colon cancer), p16 (familial atypical multiple mole-melanoma) and BRCA1/BRCA2 (breast and ovarian cancer). Id. at 3. While no other organ has a higher inherited basis for cancer than the pancreas, researchers have been unable to pinpoint the particular genetic defect(s) that contribute to one's susceptibility to pancreatic cancer. David H. Berger & William E. Fisher, *Inherited Pancreatic Cancer Syndromes*, in *Pancreatic Cancer* 73 (Douglas B. Evans et al. eds., 2002).

From the standpoint of molecular biology, research has revealed an association between pancreatic cancer and a number of genetic mutations, including the activation of the proto-oncogene K-ras and the inactivation of the tumor suppressor genes p53, p16, and DPC4. Marina E. Jean et al., *The Molecular Biology of Pancreatic Cancer*, in *Pancreatic Cancer* 15 (Douglas B. Evans et al. eds., 2002).

In one study of pancreatic adenocarcinomas, 83% possessed K-ras activation along with inactivation of p16 and p53. Id. K-ras mutations are found in 80 to 95% of pancreatic adenocarcinomas, with p53, p16, and DPC4 genes being the must frequently deleted tumor suppressor genes in cancer of the pancreas. Howe, supra at 29. Homozygous deletions, hypermethylation, and mutations of the p16 gene have been discovered in 85 to 98% of adenocarcinomas of the pancreas. Id. As might be expected by the role of alterations in the K-ras, p53, p16, and DPC4 genes, loss of regulation of the cell cycle would appear to be key to tumorigenesis in the pancreas, and may explain why this cancer is so aggressive. Jean, supra at 15. Research has also revealed a link between this cancer and abnormal regulation of certain growth factors and growth factor receptors, as well as an upregulation of matrix metalloproteinases and tumor angiogenesis regulators. Id. Epidermal growth factor, fibroblast growth factor, transforming growth factor-$\beta$, insulin-like growth factor, hepatocyte growth factor, and vascular endothelial growth factor may play various roles in pancreatic cancer, although such roles have not be elucidated. Id. at 18-22.

The development of screening techniques to detect the presence of pancreatic cancer is particularly essential for this deadly cancer, as most patients fail to present until their pancreatic tumors obstruct the bile duct or induce pain, at which point the tumors have invaded the capillary and lymphatic vessels that surround the pancreas, Howe, supra at 29; unfortunately, patients with the metastatic form of the disease typically survive less than one year after diagnosis, Jean et al., supra at 15. While computed tomography (CT) and endoscopic retrograde cholangiopancreatography (ERCP) may assist in the diagnosis of symptomatic patients, there is presently no tool for screening for pancreatic tumors that would permit their early discovery, at which point they might be curable. Howe, supra at 29. Markers such as carcinoembryonic antigen, and antibodies generated against cell lines of human colonic cancer (CA 19-9 and CA 195), human ovarian cancer (CA 125), and human pancreatic cancer (SPAN-1 and DUPAN-2) may be elevated in the serum of patients with pancreatic cancer, but these markers are not sufficiently reliable to serve as screening tools due to their lack of specificity and appearance late in the disease. Walter J. Burdette, *Cancer: Etiology, Diagnosis, and Treatment* 99 (1998); Hasholzner, U. et al., *Anticancer Res.* 19(4A): 2477-80 (1999).

Due to the present lack of adequate screening methods, physicians are increasingly turning to techniques that employ methods of molecular biology as the most promising means for early diagnosis of the disease. Howe, supra at 30. At present, there is no high sensitivity, high specificity marker that enables the detection of pancreatic cancer in asymptomatic individuals, but several biological markers are under investigation. Id. Considerable efforts are currently focusing on K-ras, with researchers devising techniques to screen samples of pancreatic juice, bile, duodenal juice, or ERCP brushings to detect K-ras mutations. Id. Because the collection of these samples is invasive and not particularly helpful in screening those who are asymptomatic, researchers have also turned to serum and stool analysis for K-ras mutations, with the former being the most promising, as the latter is hindered by the complexity of the source material. Id. at 35-38, 42. Moreover, because serum levels of the transcription factor protein p53 may parallel cancer progression, p53 is likewise being studied as possible tumor marker. Id. at 37; Jean et al., supra at 17.

Once pancreatic cancer has been diagnosed, treatment decisions are made in reference to the stage of cancer progression. A number of imaging techniques are employed to stage pancreatic cancer, with computed tomography (CT) being the present method of choice, Harmeet Kaur et al., *Pancreatic Cancer: Radiologic Staging*, in *Pancreatic Cancer* 86 (Douglas B. Evans et al. eds., 2002); Ishiguchi, T. et al., *Hepatogastroenterology* 48(40): 923-27 (2001), despite the fact that it frequently underestimates the extent of the cancer, as small-volume metastases are often beyond the resolution of CT, H. J. Kim & K. C. Conlon, *Laparascopic Staging*, in *Pancreatic Cancer* 15 (Douglas B. Evans et al. eds., 2002). MRI may at some point supplant CT in view of, inter alia, its ability to (1) contrast among various tissue, (2) modify pulse sequences to improve visualization of lesions and minimize artifacts, (3) perform imaging while limiting a patient's exposure to ionizing radiation, and (4) visualize vessels without using IV iodinated contrast reagents. Kaur et al., supra at 87. At present, however, MRI has not demonstrated a clear advantage over CT. Kim & Conlon, supra at 116.

A variety of ultrasonic techniques are also currently employed in staging, including transabdominal ultrasound (TUS), endoscopic ultrasound (EUS), and intraoperative ultrasound (IUS), with EUS being one of the most promising. Kaur et al., supra at 86; Richard A. Erickson, *Endoscopic Diagnosis and Staging: Endoscopic Ultrasound, Endoscopic Retrograde Cholangiopancreatography*, in *Pancreatic Cancer* 97-106 (Douglas B. Evans et al. eds., 2002). These techniques, however, are each limited by a variety of factors: TUS is hindered by gas in the gastrointestinal tract and fat in the peritoneum, EUS requires considerable experience in ultrasonography and endoscopy and may not be widely available, and IUS can only be used intraoperatively. Kaur et al., supra at 86.

Although in its nascent stages, the search for markers that will assist in staging pancreatic cancer has found some possible leads. For example, research has revealed that two metastasis-suppressing genes, nm23-H1 and KAI1, are differentially expressed depending on the stage of pancreatic cancer, with their expression being upregulated at early stages and down regulated at later stages of the disease. Friess, H. et al., *J. Clin. Oncol.* 19(9): 2422-32 (2001). Researchers have also focused on genetic lymph node staging, particularly searching for mutations in the K-ras proto-oncogene. Yamada, T. et al., *Int'l J. Oncol.* 16(6): 1165-71 (2000). Likewise, research has identified that the presence of mutated K-ras sequences in plasma/serum is associated with late stage pancreatic cancer, although the presence of early stage pancreatic cancer can be detected this way as well. Sorenson, G. D., *Clin. Cancer Res.* 6(6): 2129-37 (2000). A promising staging technique using a multimarker reverse transcriptase-polymerase chain reaction assay has successfully distinguished pancreatic cancer stages by assaying blood and tissue samples for mRNA expression of the following tumor markers: the β-human chorionic gonadotropin gene, the hepatocyte growth factor receptor gene c-met, and the β-1,4-N-acetyl-galactosaminyl-transferase gene. Bilchik, A. et al., *Cancer* 88(5): 1037-44 (2000).

One classification system commonly used to stage pancreatic cancer is the TNM system devised by the Union Internationale Contre le Cancer. *AJCC Cancer Staging Handbook* 3 (Irvin D. Fleming et al. eds., 5$^{th}$ ed. 1998). This system is divided into several stages, each of which evaluates the extent of cancer growth with respect to primary tumor (T), regional lymph nodes (N), and distant metastasis (M). Id.

Stage 0 is characterized by carcinoma in situ (Tis), with no regional lymph node metastasis (N0) and no distant metastasis (M0). Id. at 113. Stages I and II differ from stage 0 only in terms of tumor category: stage I involves a tumor limited only to the pancreas that is either (1) 2 cm or less in greatest dimension (T1) or (2) more than 2 cm in greatest dimension (T2), while stage II involves a tumor that extends directly into the duodenum, bile duct, or peripancreatic tissues (T3). Id. Stage III involves tumor category T1, T2, or T3; regional lymph node metastasis (N1), which involves either a single lymph node (pN1a) or multiple lymph nodes (pN1b); and no distant metastasis (M0). Stage IVA is characterized by tumor extension directly into the stomach, spleen, colon, or adjacent large vessels (T4); any N category; and no distant metastasis (M0). Lastly, stage IVB is characterized by any T category, any N category, and distant metastasis (M1). Id.

Once the cancer has been staged, the only consistently effective treatment for the disease is surgery, and with only ten to fifteen percent of patients being able to undergo potentially curative resection. Jean et al., supra at 15; Fleming et al. eds., supra at 111; William F. Regine, *Postoperative Adjuvant Therapy: Past, Present, and Future Trial Development*, in *Pancreatic Cancer* 235 (Douglas B. Evans et al. eds., 2002). Moreover, the five-year survival of those patients undergoing resection is below twenty percent. Regine, supra at 235. While chemotherapeutic agents such as gemcitabine and 5-fluorouracil have shown some effectiveness against pancreatic carcinomas, the reality is that chemotherapy has shown little impact on survival from pancreatic cancer. Burdette, supra at 101. Radiation therapy has provided conflicting results with respect to its efficacy, id., although radiation in combination with 5-fluorouracil has shown some promise, Regine, supra at 235.

In view of the failure of conventional techniques at treating pancreatic cancer, a number of novel approaches employing the techniques of molecular biology have been investigated. Considerable research has been performed in the area of gene therapy, including antisense technology, gene-directed pro-drug activation strategies, promoter gene strategies, and oncolytic viral therapies. Eugene A. Choi & Francis R. Spitz, *Strategies for Gene Therapy*, in *Pancreatic Cancer* 331 (Douglas B. Evans et al. eds., 2002); Kasuya, H. et al., *Hepatogastroenterology* 48(40): 957-61 (2001). Other recent approaches have focused on the inhibition of matrix metalloproteinases, enzymes that facilitate the metastasis and invasion of tumor cells through their degradation of basement membranes, and their role in peritumoral stromal degradation and angiogenesis. Alexander S. Rosemurgy, II & Mahmudul Haq, *Role of Matrix Metalloproteinase Inhibition in the Treatment of pancreatic Cancer*, in *Pancreatic Cancer* 369 (Douglas B. Evans et al. eds., 2002).

From the foregoing, it is clear that procedures used for detecting, diagnosing, monitoring, staging, prognosticating, and preventing the recurrence of pancreatic cancer are of critical importance to the outcome of the patient. Moreover, current procedures, while helpful in each of these analyses, are limited by their specificity, sensitivity, invasiveness, and/or their cost. As such, highly specific and sensitive procedures that would operate by way of detecting novel markers in cells, tissues, or bodily fluids, with minimal invasiveness and at a reasonable cost, would be highly desirable.

Accordingly, there is a great need for more sensitive and accurate methods for predicting whether a person is likely to develop pancreatic cancer, for diagnosing pancreatic cancer, for monitoring the progression of the disease, for staging pancreatic cancer, for determining whether pancreatic cancer has metastasized, for imaging pancreatic cancer and for better treatment of pancreatic cancer.

Colorectal Cancer

Colorectal cancer is the second most common cause of cancer death in the United States and the third most prevalent cancer in both men and women. M. L. Davila & A. D. Davila, *Screening for Colon and Rectal Cancer*, in *Colon and Rectal Cancer* 47 (Peter S. Edelstein ed., 2000). The American Cancer Society estimates that there will be about 106,370 new cases of colon cancer and 40,570 new cases of rectal cancer in the 2004 in the United States alone. Colon cancer and rectal cancer will cause about 56,730 deaths combined in the United States. ACS Website: cancer with the extension org of the world wide web. Nearly all cases of colorectal cancer arise from adenomatous polyps, some of which mature into large polyps, undergo abnormal growth and development, and ultimately progress into cancer. Davila at 55-56. This progression would appear to take at least 10 years in most patients, rendering it a readily treatable form of cancer if diagnosed early, when the cancer is localized. Davila at 56; Walter J. Burdette, *Cancer: Etiology, Diagnosis, and Treatment* 125 (1998).

Although our understanding of the etiology of colon cancer is undergoing continual refinement, extensive research in this area points to a combination of factors, including age, hereditary and nonhereditary conditions, and environmental/dietary factors. Age is a key risk factor in the development of colorectal cancer, Davila at 48, with men and women over 40 years of age become increasingly susceptible to that cancer, Burdette at 126. Incidence rates increase considerably in each subsequent decade of life. Davila at 48. A number of hereditary and nonhereditary conditions have also been linked to a heightened risk of developing colorectal cancer, including familial adenomatous polyposis (FAP), hereditary nonpolyposis colorectal cancer (Lynch syndrome or HNPCC), a personal and/or family history of colorectal cancer or adenomatous polyps, inflammatory bowel disease, diabetes mellitus, and obesity. Id. at 47; Henry T. Lynch & Jane F. Lynch, *Hereditary Nonpolyposis Colorectal Cancer (Lynch Syndromes)*, in *Colon and Rectal Cancer* 67-68 (Peter S. Edelstein ed., 2000).

Environmental/dietary factors associated with an increased risk of colorectal cancer include a high fat diet, intake of high dietary red meat, and sedentary lifestyle. Davila at 47; Reddy, B. S., *Prev. Med.* 16(4): 460-7 (1987).

Conversely, environmental/dietary factors associated with a reduced risk of colorectal cancer include a diet high in fiber, folic acid, calcium, and hormone-replacement therapy in post-menopausal women. Davila at 50-55. The effect of antioxidants in reducing the risk of colon cancer is unclear. Davila at 53.

Because colon cancer is highly treatable when detected at an early, localized stage, screening should be a part of routine care for all adults starting at age 50, especially those with first-degree relatives with colorectal cancer. One major advantage of colorectal cancer screening over its counterparts in other types of cancer is its ability to not only detect pre-cancerous lesions, but to remove them as well. Davila at 56. The key colorectal cancer screening tests in use today are fecal occult blood test, sigmoidoscopy, colonoscopy, double-contrast barium enema, and the carcinoembryonic antigen (CEA) test. Burdette at 125; Davila at 56.

The fecal occult blood test (FOBT) screens for colorectal cancer by detecting the amount of blood in the stool, the premise being that neoplastic tissue, particularly malignant tissue, bleeds more than typical mucosa, with the amount of bleeding increasing with polyp size and cancer stage. Davila at 56-57. While effective at detecting early stage tumors, FOBT is unable to detect adenomatous polyps (premalignant lesions), and, depending on the contents of the fecal sample, is subject to rendering false positives. Davila at 56-59. Sigmoidoscopy and colonoscopy, by contrast, allow direct visualization of the bowel, and enable one to detect, biopsy, and remove adenomatous polyps. Davila at 59-60, 61. Despite the advantages of these procedures, there are accompanying downsides: sigmoidoscopy, by definition, is limited to the sigmoid colon and below, colonoscopy is a relatively expensive procedure, and both share the risk of possible bowel perforation and hemorrhaging. Davila at 59-60. Double-contrast barium enema (DCBE) enables detection of lesions better than FOBT, and almost as well a colonoscopy, but it may be limited in evaluating the winding rectosigmoid region. Davila at 60. The CEA blood test, which involves screening the blood for carcinoembryonic antigen, shares the downside of FOBT, in that it is of limited utility in detecting colorectal cancer at an early stage. Burdette at 125.

Once colon cancer has been diagnosed, treatment decisions are typically made in reference to the stage of cancer progression. A number of techniques are employed to stage the cancer (some of which are also used to screen for colon cancer), including pathologic examination of resected colon, sigmoidoscopy, colonoscopy, and various imaging techniques. *AJCC Cancer Staging Handbook* 84 (Irvin D. Fleming et al. eds., 5$^{th}$ ed. 1998); Montgomery, R. C. and Ridge, J. A., *Semin. Surg. Oncol.* 15(3): 143-150 (1998). Moreover, chest films, liver functionality tests, and liver scans are employed to determine the extent of metastasis. Fleming at 84. While computerized tomography and magnetic resonance imaging are useful in staging colorectal cancer in its later stages, both have unacceptably low staging accuracy for identifying early stages of the disease, due to the difficulty that both methods have in (1) revealing the depth of bowel wall tumor infiltration and (2) diagnosing malignant adenopathy. Thoeni, R. F., *Radiol. Clin. N. Am.* 35(2): 457-85 (1997). Rather, techniques such as transrectal ultrasound (TRUS) are preferred in this context, although this technique is inaccurate with respect to detecting small lymph nodes that may contain metastases. David Blumberg & Frank G. Opelka, *Neoadjuvant and Adjuvant Therapy for Adenocarcinoma of the Rectum*, in *Colon and Rectal Cancer* 316 (Peter S. Edelstein ed., 2000).

Several classification systems have been devised to stage the extent of colorectal cancer, including the Dukes' system and the more detailed International Union against Cancer-American Joint Committee on Cancer TNM staging system, which is considered by many in the field to be a more useful staging system. Burdette at 126-27. The TNM system, which is used for either clinical or pathological staging, is divided into four stages, each of which evaluates the extent of cancer growth with respect to primary tumor (T), regional lymph nodes (N), and distant metastasis (M). Fleming at 84-85. The system focuses on the extent of tumor invasion into the intestinal wall, invasion of adjacent structures, the number of regional lymph nodes that have been affected, and whether distant metastasis has occurred. Fleming at 81.

Stage 0 is characterized by in situ carcinoma (Tis), in which the cancer cells are located inside the glandular basement membrane (intraepithelial) or lamina propria (intramucosal). In this stage, the cancer has not spread to the regional lymph nodes (N0), and there is no distant metastasis (M0). In stage I, there is still no spread of the cancer to the regional lymph nodes and no distant metastasis, but the tumor has invaded the submucosa (T1) or has progressed further to invade the muscularis propria (T2). Stage II also involves no spread of the cancer to the regional lymph nodes and no distant metastasis, but the tumor has invaded the subserosa, or the nonperitonealized pericolic or perirectal tissues (T3), or has progressed to invade other organs or structures, and/or has perforated the visceral peritoneum (T4). Stage III is characterized by any of the T substages, no distant metastasis, and either metastasis in 1 to 3 regional lymph nodes (N1) or metastasis in four or more regional lymph nodes (N2). Lastly, stage IV involves any of the T or N substages, as well as distant metastasis. Fleming at 84-85; Burdette at 127.

Currently, pathological staging of colon cancer is preferable over clinical staging as pathological staging provides a more accurate prognosis. Pathological staging typically involves examination of the resected colon section, along with surgical examination of the abdominal cavity. Fleming at 84. Clinical staging would be a preferred method of staging were it at least as accurate as pathological staging, as it does not depend on the invasive procedures of its counterpart.

Turning to the treatment of colorectal cancer, surgical resection results in a cure for roughly 50% of patients. Irradiation is used both preoperatively and postoperatively in treating colorectal cancer. Chemotherapeutic agents, particularly 5-fluorouracil, are also powerful weapons in treating colorectal cancer. Other agents include irinotecan and floxuridine, cisplatin, levamisole, methotrexate, interferon-$\alpha$, and leucovorin. Burdette at 125, 132-33. Nonetheless, thirty to forty percent of patients will develop a recurrence of colon cancer following surgical resection, which in many patients is the ultimate cause of death. Wayne De Vos, *Follow-up After Treatment of Colon Cancer, Colon and Rectal Cancer* 225 (Peter S. Edelstein ed., 2000). Accordingly, colon cancer patients must be closely monitored to determine response to therapy and to detect persistent or recurrent disease and metastasis.

The next few paragraphs describe the some of molecular bases of colon cancer. In the case of FAP, the tumor suppressor gene APC (adenomatous polyposis coli), chromosomally located at 5q21, has been either inactivated or deleted by mutation. Alberts et al., *Molecular Biology of the Cell* 1288 (3d ed. 1994). The APC protein plays a role in a number of functions, including cell adhesion, apoptosis, and repression of the c-myc oncogene. N. R. Hall & R. D. Madoff, *Genetics and the Polyp-Cancer Sequence, Colon and Rectal Cancer* 8 (Peter S. Edelstein, ed., 2000). Of those patients with colorectal cancer who have normal APC genes, over 65% have such mutations in the cancer cells but not in other tissues. Alberts et al., supra at 1288. In the case of HPNCC, patients manifest abnormalities in the tumor suppressor gene HNPCC, but only about 15% of tumors contain the mutated gene. Id. A host of other genes have also been implicated in colorectal cancer, including the K-ras, N-ras, H-ras and c-myc oncogenes, and the tumor suppressor genes DCC (deleted in colon carcinoma) and p53. Hall & Madoff, supra at 8-9; Alberts et al., supra at 1288.

Abnormalities in Wg/Wnt signal transduction pathway are also associated with the development of colorectal carcinoma. Taipale, J. and Beachy, P. A. *Nature* 411: 349-354 (2001). Wnt1 is a secreted protein gene originally identified within mouse mammary cancers by its insertion into the mouse mammary tumor virus (MMTV) gene. The protein is homologous to the wingless (Wg) gene product of *Drosophila*, in which it functions as an important factor for the determination of dorsal-ventral segmentation and regulates the formation of fly imaginal discs. Wg/Wnt pathway controls cell proliferation, death and differentiation. Taipal (2001). There are at least 13 members in the Wnt family. These proteins have been found expressed mainly in the central nervous system (CNS) of vertebrates as well as other tissues such as mammary and intestine. The Wnt proteins are the ligands for a family of seven transmembrane domain receptors related to the Frizzled gene product in *Drosophila*. Binding Wnt to Frizzled stimulates the activity of the downstream target, Disheveled, which in turn inactivates the glycogen synthesase kinase 3β (GSK3β). Taipal (2001). Usually active GSK3β will form a complex with the adenomatous polyposis coli (APC) protein and phosphorylate another complex member, β-catenin. Once phosphorylated, β-catenin is directed to degradation through the ubiquitin pathway. When GSK3β or APC activity is down regulated, β-catenin is accumulated in the cytoplasm and binds to the T-cell factor or lymphocyte excitation factor (Tcf/Lef) family of transcriptional factors. Binding of β-catenin to Tcf releases the transcriptional repression and induces gene transcription. Among the genes regulated by β-catenin are a transcriptional repressor Engrailed, a transforming growth factor-β (TGF-β) family member Decapentaplegic, and the cytokine Hedgehog in *Drosophila*. β-Catenin also involves in regulating cell adhesion by binding to α-catenin and E-cadherin. On the other hand, binding of β-catenin to these proteins controls the cytoplasmic β-catenin level and its complexing with TCF. Taipal (2001). Growth factor stimulation and activation of c-src or v-src also regulate β-catenin level by phosphorylation of α-catenin and its related protein, p120$^{cas}$. When phosphorylated, these proteins decrease their binding to E-cadherin and β-catenin resulting in the accumulation of cytoplasmic β-catenin. Reynolds, A. B. et al. *Mol. Cell Biol.* 14: 8333-8342 (1994). In colon cancer, c-src enzymatic activity has been shown increased to the level of v-src. Alternation of components in the Wg/Wnt pathway promotes colorectal carcinoma development The best-known modifications are to the APC gene. Nicola S et al. *Hum. Mol. Genet* 10:721-733 (2001). This germline mutation causes the appearance of hundreds to thousands of adenomatous polyps in the large bowel. It is the gene defect that accounts for the autosomally dominantly inherited FAP and related syndromes. The molecular alternations that occur in this pathway largely involve deletions of alleles of tumor-suppressor genes, such as APC, p53 and Deleted in Colorectal Cancer (DCC), combined with mutational activation of proto-oncogenes, especially c-Ki-ras. Aoki, T. et al. *Human Mutat.* 3: 342-346 (1994). All of these lead to genomic instability in colorectal cancers.

Another source of genomic instability in colorectal cancer is the defect of DNA mismatch repair (MMR) genes. Human homologues of the bacterial mutHLS complex (hMSH2, hMLH1, hPMS1, hPMS2 and hMSH6), which is involved in the DNA mismatch repair in bacteria, have been shown to cause the HNPCC (about 70-90% HNPCC) when mutated. Modrich, P. and Lahue, R. *Ann Rev. Biochem.* 65: 101-133 (1996); and Peltomäki, P. *Hum. Mol. Genet* 10: 735-740 (2001). The inactivation of these proteins leads to the accumulation of mutations and causes genetic instability that represents errors in the accurate replication of the repetitive mono-, di-, tri- and tetra-nucleotide repeats, which are scattered throughout the genome (microsatellite regions). Jass, J. R. et al. *J. Gastroenterol Hepatol* 17: 17-26 (2002). Like in the classic FAP, mutational activation of c-Ki-ras is also required for the promotion of MSI in the alternative HNPCC. Mutations in other proteins such as the tumor suppressor protein phosphatase PTEN (Zhou, X. P. et al. *Hum. Mol. Genet* 11: 445-450 (2002)), BAX (Buttler, L. M. *Aus. N. Z. J. Surg.* 69: 88-94 (1999)), Caspase-5 (Planck, M. *Cancer Genet Cytogenet.* 134: 46-54 (2002)), TGFβ-RII (Fallik, D. et al. *Gastroenterol Clin Biol.* 24: 917-22 (2000)) and IGFII-R (Giovannucci E. *J. Nutr.* 131: 3109S-20S (2001)) have also been found in some colorectal tumors possibly as the cause of MMR defect.

Some tyrosine kinases have been shown up-regulated in colorectal tumor tissues or cell lines like HT29. Skoudy, A. et al. *Biochem J.* 317 (Pt 1): 279-84 (1996). Focal adhesion kinase (FAK) and its up-stream kinase c-src and c-yes in colonic epithelia cells may play an important role in the promotion of colorectal cancers through the extracellular matrix (ECM) and integrin-mediated signaling pathways. Jessup, J. M. et al., *The molecular biology of colorectal carcinoma*, in: *The Molecular Basis of Human Cancer.* 251-268 (Coleman W. B. and Tsongalis G. J. Eds. 2002). The formation of c-src/FAK complexes may coordinately deregulate VEGF expression and apoptosis inhibition. Recent evidences suggest that a specific signal-transduction pathway for cell survival that implicates integrin engagement leads to FAK activation and thus activates PI-3 kinase and akt. In turn, akt phosphorylates BAD and blocks apoptosis in epithelial cells. The activation of c-src in colon cancer may induce VEGF expression through the hypoxia pathway. Other genes that may be implicated in colorectal cancer include Cox enzymes (Ota, S. et al. *Aliment Pharmacol. Ther.* 16 (Suppl 2): 102-106 (2002)), estrogen (al-Azzawi, F. and Wahab, M. *Climacteric* 5: 3-14 (2002)), peroxisome proliferator-activated receptor-γ (PPAR-γ) (Gelman, L. et al. *Cell Mol. Life Sci.* 55: 932-943 (1999)), IGF-I (Giovannucci (2001)), thymine DNA glycosylase (TDG) (Hardeland, U. et al. *Prog. Nucleic Acid Res. Mol. Biol.* 68: 235-253 (2001)) and EGF (Mendelsohn, J. *Endocrine-Related Cancer* 8: 3-9 (2001)).

Gene deletion and mutation are not the only causes for development of colorectal cancers. Epigenetic silencing by DNA methylation also accounts for the lost of function of colorectal cancer suppressor genes. A strong association between MSI and CpG island methylation has been well characterized in sporadic colorectal cancers with high MSI but not in those of hereditary origin. In one experiment, DNA methylation of MLH1, CDKN2A, MGMT, THBS1, RARB, APC, and p14ARF genes has been shown in 80%, 55%, 23%, 23%, 58%, 35%, and 50% of 40 sporadic colorectal cancers with high MSI respectively. Yamamoto, H. et al. *Genes Chromosomes Cancer* 33: 322-325 (2002); and Kim, K. M. et al.

*Oncogene.* 12; 21(35): 5441-9 (2002). Carcinogen metabolism enzymes such as GST, NAT, CYP and MTHFR are also associated with an increased or decreased colorectal cancer risk. Pistorius, S. et al. *Kongressbd Dtsch Ges Chir Kongr* 118: 820-824 (2001); and Potter, J. D. *J. Natl. Cancer Inst.* 91: 916-932 (1999).

From the foregoing, it is clear that procedures used for detecting, diagnosing, monitoring, staging, prognosticating, and preventing the recurrence of colorectal cancer are of critical importance to the outcome of the patient. Moreover, current procedures, while helpful in each of these analyses, are limited by their specificity, sensitivity, invasiveness, and/or their cost. As such, highly specific and sensitive procedures that would operate by way of detecting novel markers in cells, tissues, or bodily fluids, with minimal invasiveness and at a reasonable cost, would be highly desirable.

Accordingly, there is a great need for more sensitive and accurate methods for predicting whether a person is likely to develop colorectal cancer, for diagnosing colorectal cancer, for monitoring the progression of the disease, for staging the colorectal cancer, for determining whether the colorectal cancer has metastasized, and for imaging the colorectal cancer. Following accurate diagnosis, there is also a need for less invasive and more effective treatment of colorectal cancer.

Angiogenesis in Cancer

Growth and metastasis of solid tumors are also dependent on angiogenesis. Folkman, J., 1986, *Cancer Research,* 46, 467-473; Folkman, J., 1989, *Journal of the National Cancer Institute,* 82, 4-6. It has been shown, for example, that tumors that enlarge to greater than 2 mm must obtain their own blood supply and do so by inducing the growth of new capillary blood vessels. Once these new blood vessels become embedded in the tumor, they provide a means for tumor cells to enter the circulation and metastasize to distant sites such as liver, lung or bone. Weidner, N., et al., 1991, *The New England Journal of Medicine,* 324(1), 1-8.

Angiogenesis, defined as the growth or sprouting of new blood vessels from existing vessels, is a complex process that primarily occurs during embryonic development. The process is distinct from vasculogenesis, in that the new endothelial cells lining the vessel arise from proliferation of existing cells, rather than differentiating from stem cells. The process is invasive and dependent upon proteolysis of the extracellular matrix (ECM), migration of new endothelial cells, and synthesis of new matrix components. Angiogenesis occurs during embryogenic development of the circulatory system; however, in adult humans, angiogenesis only occurs as a response to a pathological condition (except during the reproductive cycle in women).

Under normal physiological conditions in adults, angiogenesis takes place only in very restricted situations such as hair growth and wounding healing. Auerbach, W. and Auerbach, R., 1994, *Pharmacol Ther.* 63(3):265-3 11; Ribatti et al., 1991, *Haematologica* 76(4):3 11-20; Risau, 1997, *Nature* 386(6626):67 1-4. Angiogenesis progresses by a stimulus that results in the formation of a migrating column of endothelial cells. Proteolytic activity is focused at the advancing tip of this "vascular sprout", which breaks down the ECM sufficiently to permit the column of cells to infiltrate and migrate. Behind the advancing front, the endothelial cells differentiate and begin to adhere to each other, thus forming a new basement membrane. The cells then cease proliferation and finally define a lumen for the new arteriole or capillary.

Unregulated angiogenesis has gradually been recognized to be responsible for a wide range of disorders, including, but not limited to, cancer, cardiovascular disease, rheumatoid arthritis, psoriasis and diabetic retinopathy. Folkman, 1995, *Nat Med* 1(1):27-31; Isner, 1999, *Circulation* 99(13): 1653-5; Koch, 1998, *Arthritis Rheum* 41(6):951-62; Walsh, 1999, *Rheumatology* (Oxford) 38(2):103-12; Ware and Simons, 1997, *Nat Med* 3(2): 158-64.

Of particular interest is the observation that angiogenesis is required by solid tumors for their growth and metastases. Folkman, 1986 supra; Folkman 1990, *J Natl. Cancer Inst.,* 82(1) 4-6; Folkman, 1992, *Semin Cancer Biol* 3(2):65-71; Zetter, 1998, *Annu Rev Med* 49:407-24. A tumor usually begins as a single aberrant cell, which can proliferate only to a size of a few cubic millimeters due to the distance from available capillary beds, and it can stay 'dormant' without further growth and dissemination for a long period of time. Some tumor cells then switch to the angiogenic phenotype to activate endothelial cells, which proliferate and mature into new capillary blood vessels. These newly formed blood vessels not only allow for continued growth of the primary tumor, but also for the dissemination and recolonization of metastatic tumor cells. The precise mechanisms that control the angiogenic switch is not well understood, but it is believed that neovascularization of tumor mass results from the net balance of a multitude of angiogenesis stimulators and inhibitors Folkman, 1995, supra.

One of the most potent angiogenesis inhibitors is endostatin identified by O'Reilly and Folkman. O'Reilly et al., 1997, *Cell* 88(2):277-85; O'Reilly et al., 1994, *Cell* 79(2):3 15-28. Its discovery was based on the phenomenon that certain primary tumors can inhibit the growth of distant metastases. O'Reilly and Folkman hypothesized that a primary tumor initiates angiogenesis by generating angiogenic stimulators in excess of inhibitors. However, angiogenic inhibitors, by virtue of their longer half life in the circulation, reach the site of a secondary tumor in excess of the stimulators. The net result is the growth of primary tumor and inhibition of secondary tumor. Endostatin is one of a growing list of such angiogenesis inhibitors produced by primary tumors. It is a proteolytic fragment of a larger protein: endostatin is a 20 kDa fragment of collagen XVIII (amino acid H1132-K1315 in murine collagen XVIII. Endostatin has been shown to specifically inhibit endothelial cell proliferation in vitro and block angiogenesis in vivo. More importantly, administration of endostatin to tumor-bearing mice leads to significant tumor regression, and no toxicity or drug resistance has been observed even after multiple treatment cycles. Boehm et al., 1997, Nature 390(6658):404-407. The fact that endostatin targets genetically stable endothelial cells and inhibits a variety of solid tumors makes it a very attractive candidate for anticancer therapy. Fidler and Ellis, 1994, Cell 79(2):185-8; Gastl et al., 1997, Oncology 54(3):177-84; Hinsbergh et al., 1999, Ann Oncol 10 Suppl 4:60-3. In addition, angiogenesis inhibitors have been shown to be more effective when combined with radiation and chemotherapeutic agents. Klement, 2000, J. Clin Invest, 105(8) R15-24. Browder, 2000, Cancer Res. 6-(7) 1878-86, Arap et al., 1998, Science 279(5349): 377-80; Mauceri et al., 1998, Nature 394(6690):287-91.

The present invention provides alternative methods of treating ovarian, pancreatic and colon cancer that overcome the limitations of conventional therapeutic methods as well as offer additional advantages that will be apparent from the detailed description below.

SUMMARY OF THE INVENTION

This invention is directed to an isolated Ovr115 antibody that binds to Ovr115 on a mammalian cell in vivo. The invention is further directed to an isolated Ovr115 antibody that internalizes upon binding to Ovr115 on a mammalian cell in vivo. The antibody may be a monoclonal antibody. Alternatively, the antibody is an antibody fragment or a chimeric or a humanized antibody. The monoclonal antibody may be produced by a hybridoma selected from the group of hybridomas deposited under American Type Culture Collection accession number PTA-5202, PTA-5916, PTA-5917, PTA-5918, PTA-5919 and PTA-5920. The invention is further directed to an isolated Ovr115 antibody that inhibits Ovr115 activity. Preferably, the Ovr115 activity is a protease activity.

The antibody may compete for binding to the same epitope as the epitope bound by the monoclonal antibody produced by a hybridoma selected from the group of hybridomas deposited under the American Type Culture Collection accession number PTA-5202, PTA-5916, PTA-5917, PTA-5918, PTA-5919 and PTA-5920.

The invention is also directed to conjugated antibodies. They may be conjugated to a growth inhibitory agent or a cytotoxic agent. The cytotoxic agent may be selected from the group consisting of toxins, antibiotics, radioactive isotopes and nucleolytic enzymes and toxins. Examples of toxins include, but are not limited to, maytansin, maytansinoids, saporin, gelonin, ricin or calichearmicin.

The mammalian cell may be a cancer cell. Preferably, the anti-Ovr115 monoclonal antibody that inhibits the growth of Ovr115-expressing cancer cells in vivo.

The antibody may be produced in bacteria. Alternatively, the antibody may be a humanized form of an anti-Ovr115 antibody produced by a hybridoma selected from the group of hybridomas having ATCC accession number PTA-5202, PTA-5916, PTA-5917, PTA-5918, PTA-5919 and PTA-5920.

Preferably, the cancer is selected from the group consisting of ovarian, pancreatic and colon cancer. The invention is also directed to a method of producing the antibodies comprising culturing an appropriate cell and recovering the antibody from the cell culture.

The invention is also directed to compositions comprising the antibodies and a carrier. The antibody may be conjugated to a cytotoxic agent. The cytotoxic agent may be a radioactive isotope or other chemotherapeutic agent.

The invention is also directed to a method of killing an Ovr115-expressing cancer cell, comprising contacting the cancer cell with the antibodies of this invention, thereby killing the cancer cell. The cancer cell may be selected from the group consisting of ovarian, pancreatic and colon cancer cell.

The ovarian, pancreatic or colon cancer may be ovarian epithelial cancer, pancreatic epithelial cancer or colon epithelial cancer including ovarian serous adenocarcinoma and colon adenocarcinoma or metastatic cancer.

The invention is also directed to a method of alleviating an Ovr115-expressing cancer in a mammal, comprising administering a therapeutically effective amount of the antibodies to the mammal.

In addition, the invention is directed to an article of manufacture comprising a container and a composition contained therein, wherein the composition comprises an antibody as described herein. The article of manufacture may also comprise an additional component, e.g., a package insert indicating that the composition can be used to treat ovarian, pancreatic and colon cancer.

BRIEF DESCRIPTION OF THE FIGURES

FIG. 1A shows the results of FACS Analysis of Ovr115 Transfected Mouse LMTK Cells.

FIG. 1B shows the results of FACS analysis Ovr115.F76.2 MAb Binds to A431 (QPCR+) Cell Line.

FIG. 2 shows Ovr115 A51.2 binds to the surface of live ovarian CaOV3 cancer cells.

FIG. 3 shows Ovr115 Cy3-A51.2 binds to live ovarian CaOV3 cancer cells.

FIG. 4 shows Ovr115 Cy3-A51.2 binds to live ovarian cancer cells and is internalized.

FIG. 5 shows Ovr115 Cy3-A51.2 binds to live pancreatic cancer cells.

FIG. 6 shows the localization of Ovr115 in ovarian cancer cells.

FIG. 7 shows the localization of Ovr115 in ovarian cancer cells.

FIG. 10 shows Ovarian Serous Papillary Adenocarcinoma, Unfixed OCT Frozen Sections immunolabeled with Ovr115.D43.1.

FIG. 11 shows Ovr115.F64.2 and Ovr115.D43.1 specifically label frozen and FFPE colon adenocarcinoma cancer cells compared to control Mouse IgG1.

FIG. 12 is an epitope map for monoclonal antibodies binding to Ovr115.

FIG. 13 shows a Sandwich ELISA detection of Ovr115 in tumor cell and transfected cell lysates using Ovr115.D43 & F-Series MAbs.

FIG. 14 shows Anti-Ovr115 Activity Screening with Ovr115 MAbs.

FIG. 15 shows Ovr115 mAbs Recognize Native Ovr115 Protein in Human Cell Lines and Ovarian Tumors by Western Blot (mAb Ovr115.F21.1).

FIG. 16 shows Transformation of Epithelial Cells by Overexpression of Ovr115.

FIG. 17 shows Overexpression of Ovr115 Induces SQ Tumor Growth in SCID Beige Mice.

FIG. 18 shows Expression of Ovr115 Protein from Tumor Xenografts.

FIG. 19 shows Overexpression of Ovr115 Protects RK3E Cells From Apoptosis.

DETAILED DESCRIPTION OF THE INVENTION

Definitions and General Techniques

Figure 8B:
FIG. 8 shows Ovr115 D84 labels epithelial cells in ovarian cancer tumors.

Human "Ovr115" as used herein, refers to a protein of 435 amino acids that is expressed on the cell surface as a glycoprotein, whose nucleotide and/or amino acid sequence sequences are as disclosed in e.g., WO 00/12758-A1, Cancer specific gene (CSG) Ovr115 (clone ID 1283171); WO 99/36550-A2, Human protease HUPM-6; WO 01/04141-A2, Human seripancrin cDNA; and WO 00/12708-A2, Human PRO1570 (UNQ776) cDNA sequence (SEQ ID NO:274 therein). Ovr115 has also been disclosed in the REFSEQ database as: NM_019894.2 (GI: 34304348) *Homo sapiens* transmembrane protease, serine 4 (TMPRSS4), transcript variant 1, mRNA. REFSEQ gives the following summary of TMPRSS4 (Ovr115):

"This gene encodes a member of the serine protease family. Serine proteases are known to be involved in a variety of biological processes, whose malfunction often leads to human diseases and disorders. This gene was identified as a gene overexpressed in pancreatic carcinoma. The encoded protein is membrane bound with a N-terminal anchor sequence and a glycosylated extracellular region containing the serine protease domain."

The amino acids 52-435 of Ovr115 are located on the cell surface. Ovr115 as used herein includes allelic variants and conservative substitution mutants of the protein that have Ovr115 biological activity.

*Homo sapiens* transmembrane protease, serine 4 (TM-PRSS4) was previously identified as novel transmembrane serine protease (TMPRSS3). Wallrapp et al., A novel transmembrane serine protease (TMPRSS3) overexpressed in pancreatic cancer, Cancer Res. 60(10):2602-6 (2000). Our findings that Ovr115 is apparently associated to the more aggressive ovarian, pancreatic and colon cancers make this cell surface antigen an attractive target for immunotherapy of these and possibly other tumor types.

The term "antibody" (Ab) as used herein includes monoclonal antibodies, polyclonal antibodies, multispecific antibodies (e.g. bispecific antibodies), and antibody fragments, so long as they exhibit the desired biological activity. The term "immunoglobulin" (Ig) is used interchangeably with "antibody" herein.

An "isolated antibody" is one that has been identified and separated and/or recovered from a component of its natural environment Contaminant components of its natural environment are materials that would interfere with diagnostic or therapeutic uses for the antibody, and may include enzymes, hormones, and other proteinaceous or nonproteinaceous solutes. Preferably, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α, δ and γ chains and four CH domains for μ and ε isotypes. Each L chain has at the N-terminus, a variable domain (VL) followed by a constant domain (CL) at its other end.

The VL is aligned with the VH and the CL is aligned with the first constant domain of the heavy chain (CHI). Particular amino acid residues are believed to form an interface between the light chain and heavy chain variable domains. The pairing of a VH and VL together forms a single antigen-binding site. For the structure and properties of the different classes of antibodies, see, e.g., Basic and Clinical Immunology, 8th edition, Daniel P. Stites, Abba I. Teff and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated α, δ, ε, γ and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and define specificity of a particular antibody for its particular antigen. However, the variability is not evenly distributed across the 1-10-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a P-sheet configuration, connected by three hypervariable regions, which form loops connecting, and in some cases forming part of, the P-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about residues 24-34 (LI), 5056 (L2) and 89-97 (L3) in the VL, and around about 1-35 (HI), 50-65 (H2) and 95-102 (113) in the VH; Kabat et al., Sequences of Proteins of Immunological Interest, 5th Ed. Public Health Service, National Institutes of Health, Bethesda, Md. (1991)) and/or those residues from a "hypervariable loop" (e.g. residues 26-32 (LI), 50-52 (L2) and 91-96 (U) in the VL, and 26-32 (HI), 53-55 (1-12) and 96-101 (H3) in the VH; Chothia and Lesk J. Mol. Biol. 196: 901-917 (1987)).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations, which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816, 567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences.

An "intact" antibody is one that comprises an antigen-binding site as well as a CL and at least heavy chain constant domains, CHI, CH2 and CH3. The constant domains may be native sequence constant domains (e.g. human native sequence constant domains) or amino acid sequence variant thereof. Preferably, the intact antibody has one or more effector functions.

An "antibody fragment" comprises a portion of an intact antibody, preferably the antigen binding or variable region of the intact antibody. Examples of antibody fragments include Fab, Fab', F(ab')2, and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments. Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CHI). Each Fab fragment is monovalent with respect to antigen binding, i.e., it has a single antigen-binding site. Pepsin treatment of an antibody yields a single large F(ab')2 fragment which roughly corresponds to two disulfide linked Fab fragments having divalent antigen-binding activity and is still capable of cross-linking antigen. Fab' fragments differ from Fab fragments by having additional few residues at the carboxy terminus of the CHI domain including one or more cysteines from the antibody hinge region. Fab'-SH is the designation herein for Fab' in which the cysteine residue(s) of the constant domains bear a free thiol group. F(ab')2 antibody fragments originally were produced as pairs of 8 Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment that contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains that enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

A "native sequence" polypeptide is one that has the same amino acid sequence as a polypeptide (e.g., antibody) derived from nature. Such native sequence polypeptides can be isolated from nature or can be produced by recombinant or synthetic means. Thus, a native sequence polypeptide can have the amino acid sequence of a naturally occurring human polypeptide, murine polypeptide, or polypeptide from any other mammalian species.

The term "amino acid sequence variant" refers to a polypeptide that has amino acid sequences that differ to some extent from a native sequence polypeptide. Ordinarily, amino acid sequence variants of Ovr115 will possess at least about 70% homology with the native sequence Ovr115, preferably, at least about 80%, more preferably at least about 85%, even more preferably at least about 90% homology, and most preferably at least 95%. The amino acid sequence variants can possess substitutions, deletions, and/or insertions at certain positions within the amino acid sequence of the native amino acid sequence.

The phrase "functional fragment or analog" of an antibody is a compound having qualitative biological activity in common with a full-length antibody. For example, a functional fragment or analog of an anti-IgE antibody is one that can bind to an IgE immunoglobulin in such a manner so as to prevent or substantially reduce the ability of such molecule from having the ability to bind to the high affinity receptor, FcϵRI.

"Homology" is defined as the percentage of residues in the amino acid sequence variant that are identical after aligning the sequences and introducing gaps, if necessary, to achieve the maximum percent homology. Methods and computer programs for the alignment are well known in the art. Sequence similarity may be measured by any common sequence analysis algorithm, such as GAP or BESTFIT or other variation Smith-Waterman alignment. See, T. F. Smith and M. S. Waterman, J. Mol. Biol. 147:195-197 (1981) and W. R. Pearson, Genomics 11:635-650 (1991).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332: 323-329 (1988); and Presta, Curr. Op. Struct. Biol. 2:593-596 (1992).

As used herein, an anti-Ovr115 antibody that "internalizes" is one that is taken up by (i.e., enters) the cell upon binding to Ovr115 on a mammalian cell (i.e. cell surface Ovr115). The internalizing antibody will of course include antibody fragments, human or humanized antibody and antibody conjugate. For therapeutic applications, internalization in vivo is contemplated. The number of antibody molecules internalized will be sufficient or adequate to kill an Ovr115-expressing cell, especially an Ovr115-expressing cancer cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugated to the antibody is sufficient to kill the tumor cell.

Whether an anti-Ovr115 antibody internalizes upon binding Ovr115 on a mammalian cell can be determined by various assays including those described in the experimental examples below. For example, to test internalization in vivo, the test antibody is labeled and introduced into an animal known to have Ovr115 expressed on the surface of certain cells. The antibody can be radiolabeled or labeled with fluorescent or gold particles, for instance. Animals suitable for this assay include a mammal such as a NCR nude mouse that contains a human Ovr115-expressing tumor transplant or xenograft, or a mouse into which cells transfected with human Ovr115 have been introduced, or a transgenic mouse expressing the human Ovr115 transgene. Appropriate controls include animals that did not receive the test antibody or that received an unrelated antibody, and animals that received an antibody to another antigen on the cells of interest, which antibody is known to be internalized upon binding to the antigen. The antibody can be administered to the animal, e.g., by intravenous injection. At suitable time intervals, tissue sections of the animal can be prepared using known methods or as described in the experimental examples below, and analyzed by light microscopy or electron microscopy, for internalization as well as the location of the internalized antibody in the cell. For internalization in vitro, the cells can be incubated in tissue culture dishes in the presence or absence of the relevant antibodies added to the culture media and processed for microscopic analysis at desired time points. The presence of an internalized, labeled antibody in the cells can be directly visualized by microscopy or by autoradiography if radiolabeled antibody is used. Alternatively, in a quantitative biochemical assay, a population of cells comprising Ovr115-expressing cells are contacted in vitro or in vivo with a radiolabeled test antibody and the cells (if contacted in vivo, cells are then isolated after a suitable amount of time) are treated with a protease or subjected to an acid wash to remove uninternalized antibody on the cell surface. The cells are ground up and the amount of protease resistant, radioactive counts per minute (cpm) associated with each batch of cells is measured by passing the homogenate through a scintillation counter. Based on the known specific activity of the radiolabeled antibody, the number of antibody molecules internalized per cell can be deduced from the scintillation counts of the ground-up cells. Cells are "contacted" with antibody in vitro preferably in solution form such as by adding the cells to the cell culture media in the culture dish or flask and mixing the antibody well with the media to ensure uniform exposure of the cells to the antibody. Instead of adding to the culture media, the cells can be contacted with the test antibody in an isotonic solution such as PBS in a test tube for the desired time period. In vivo, the cells are contacted with antibody by any suitable method of administering the test antibody such as the methods of administration described below when administered to a patient.

The faster the rate of internalization of the antibody upon binding to the Ovr115-expressing cell in vivo, the faster the desired killing or growth inhibitory effect on the target Ovr115-expressing cell can be achieved, e.g., by a cytotoxic immunoconjugate. Preferably, the kinetics of internalization of the anti-Ovr115 antibodies are such that they favor rapid killing of the Ovr115-expressing target cell. Therefore, it is desirable that the anti-Ovr115 antibody exhibit a rapid rate of internalization preferably, within 24 hours from administration of the antibody in vivo, more preferably within about 12 hours, even more preferably within about 30 minutes to 1 hour, and most preferably, within about 30 minutes. The present invention provides antibodies that internalize as fast as about 15 minutes from the time of introducing the anti-Ovr115 antibody in vivo. The antibody will preferably be internalized into the cell within a few hours upon binding to Ovr115 on the cell surface, preferably within 1 hour, even more preferably within 15-30 minutes.

To determine if a test antibody can compete for binding to the same epitope as the epitope bound by the anti-Ovr115 antibodies of the present invention including the antibodies produced by the hybridomas deposited with the ATCC, a cross-blocking assay e.g., a competitive ELISA assay can be performed. In an exemplary competitive ELISA assay, Ovr115-coated wells of a microtiter plate, or Ovr115-coated sepharose beads, are pre-incubated with or without candidate competing antibody and then a biotin-labeled anti-Ovr115 antibody of the invention is added. The amount of labeled anti-Ovr115 antibody bound to the Ovr115 antigen in the wells or on the beads is measured using avidin-peroxidase conjugate and appropriate substrate.

Alternatively, the anti-Ovr115 antibody can be labeled, e.g., with a radioactive or fluorescent label or some other detectable and measurable label. The amount of labeled anti-Ovr115 antibody that binds to the antigen will have an inverse correlation to the ability of the candidate competing antibody (test antibody) to compete for binding to the same epitope on the antigen, i.e., the greater the affinity of the test antibody for the same epitope, the less labeled anti-Ovr-110 antibody will be bound to the antigen-coated wells. A candidate competing antibody is considered an antibody that binds substantially to the same epitope or that competes for binding to the same epitope as an anti-Ovr115 antibody of the invention if the candidate competing antibody can block binding of the anti-Ovr115 antibody by at least 20%, preferably by at least 20-50%, even more preferably, by at least 50% as compared to a control performed in parallel in the absence of the candidate competing antibody (but may be in the presence of a known noncompeting antibody). It will be understood that variations of this assay can be performed to arrive at the same quantitative value.

An antibody having a "biological characteristic" of a designated antibody, such as any of the monoclonal antibodies Ovr115.A2.1, Ovr115.A11.1, Ovr115.A51.2 (also known as Ovr115 A51.2), Ovr115.A63.2, Ovr115.D3, Ovr115.D15, Ovr115.D20, Ovr115.D26, Ovr115.D31, Ovr115.D32, Ovr115.D34, Ovr115.D37, Ovr115.D43, Ovr115.D51, Ovr115.D69, Ovr115.D71, Ovr115.D81, Ovr115.D84, Ovr115.D94, Ovr115.F2, Ovr115.F3, Ovr115.F4, Ovr115.F5, Ovr115.F6, Ovr115.F7, Ovr115.F8, Ovr115.F9, Ovr115.F10, Ovr115.F11, Ovr115.F13, Ovr115.F14, Ovr115.F15, Ovr115.F19, Ovr115.F20, Ovr115.F21, Ovr115.F22, Ovr115.F23, Ovr115.F24, Ovr115.F25, Ovr115.F26, Ovr115.F28, Ovr115.F29, Ovr115.F30, Ovr115.F31, Ovr115.F32, Ovr115.F33, Ovr115.F34, Ovr115.F35, Ovr115.F36, Ovr115.F37, Ovr115.F38, Ovr115.F39, Ovr115.F40, Ovr115.F41, Ovr115.F42, Ovr115.F43, Ovr115.F46, Ovr115.F47, Ovr115.F49, Ovr115.F50, Ovr115.F51, Ovr115.F53, Ovr115.F54, Ovr115.F55, Ovr115.F56, Ovr115.F57, Ovr115.F58, Ovr115.F59, Ovr115.F60, Ovr115.F61, Ovr115.F62, Ovr115.F63, Ovr115.F64, Ovr115.F65, Ovr115.F66, Ovr115.F67, Ovr115.F69, Ovr115.F70, Ovr115.F71, Ovr115.F72, Ovr115.F73, Ovr115.F74, Ovr115.F75, Ovr115.F76, Ovr115.F77, Ovr115.F78, Ovr115.F79, Ovr115.F80, Ovr115.F81, Ovr115.F82 and Ovr115.F83, is one which possesses one or more of the biological characteristics of that antibody which distinguish it from other antibodies that bind to the same antigen, Ovr115.A2.1, Ovr115.A11.1, Ovr115.A51.2 (also known as Ovr115 A51.2), Ovr115.A63.2, Ovr115.D3, Ovr115.D15, Ovr115.D20, Ovr115.D26, Ovr115.D31, Ovr115.D32, Ovr115.D34, Ovr115.D37, Ovr115.D43, Ovr115.D51, Ovr115.D69, Ovr115.D71, Ovr115.D81, Ovr115.D84, Ovr115.D94, Ovr115.F2, Ovr115.F3, Ovr115.F4, Ovr115.F5, Ovr115.F6, Ovr115.F7, Ovr115.F8, Ovr115.F9, Ovr115.F10, Ovr115.F11, Ovr115.F13, Ovr115.F14, Ovr115.F15, Ovr115.F19, Ovr115.F20, Ovr115.F21, Ovr115.F22, Ovr115.F23, Ovr115.F24, Ovr115.F25, Ovr115.F26, Ovr115.F28, Ovr115.F29, Ovr115.F30, Ovr115.F31, Ovr115.F32, Ovr115.F33, Ovr115.F34, Ovr115.F35, Ovr115.F36, Ovr115.F37, Ovr115.F38, Ovr115.F39, Ovr115.F40, Ovr115.F41, Ovr115.F42, Ovr115.F43, Ovr115.F46, Ovr115.F47, Ovr115.F49, Ovr115.F50, Ovr115.F51, Ovr115.F53, Ovr115.F54, Ovr115.F55, Ovr115.F56, Ovr115.F57, Ovr115.F58, Ovr115.F59, Ovr115.F60, Ovr115.F61, Ovr115.F62, Ovr115.F63, Ovr115.F64, Ovr115.F65, Ovr115.F66, Ovr115.F67, Ovr115.F69, Ovr115.F70, Ovr115.F71, Ovr115.F72, Ovr115.F73, Ovr115.F74, Ovr115.F75, Ovr115.F76, Ovr115.F77, Ovr115.F78, Ovr115.F79, Ovr115.F80, Ovr115.F81, Ovr115.F82 and Ovr115.F83 will bind the same epitope as that bound by Ovr115.A2.1, Ovr115.A11.1, Ovr115.A51.2 (also known as Ovr115 A51.2), Ovr115.A63.2, Ovr115.D3, Ovr115.D15, Ovr115.D20, Ovr115.D26, Ovr115.D31, Ovr115.D32, Ovr115.D34, Ovr115.D37, Ovr115.D43, Ovr115.D51, Ovr115.D69, Ovr115.D71, Ovr115.D81, Ovr115.D84, Ovr115.D94, Ovr115.F2, Ovr115.F3, Ovr115.F4, Ovr115.F5, Ovr115.F6, Ovr115.F7, Ovr115.F8, Ovr115.F9, Ovr115.F10, Ovr115.F11, Ovr115.F13, Ovr115.F14, Ovr115.F15, Ovr115.F19, Ovr115.F20, Ovr115.F21, Ovr115.F22, Ovr115.F23, Ovr115.F24, Ovr115.F25, Ovr115.F26, Ovr115.F28, Ovr115.F29, Ovr115.F30, Ovr115.F31, Ovr115.F32, Ovr115.F33, Ovr115.F34, Ovr115.F35, Ovr115.F36, Ovr115.F37, Ovr115.F38, Ovr115.F39, Ovr115.F40, Ovr115.F41, Ovr115.F42, Ovr115.F43, Ovr115.F46, Ovr115.F47, Ovr115.F49, Ovr115.F50, Ovr115.F51, Ovr115.F53, Ovr115.F54, Ovr115.F55, Ovr115.F56, Ovr115.F57, Ovr115.F58, Ovr115.F59, Ovr115.F60, Ovr115.F61, Ovr115.F62, Ovr115.F63, Ovr115.F64, Ovr115.F65, Ovr115.F66, Ovr115.F67, Ovr115.F69, Ovr115.F70, Ovr115.F71, Ovr115.F72, Ovr115.F73, Ovr115.F74, Ovr115.F75, Ovr115.F76, Ovr115.F77, Ovr115.F78, Ovr115.F79, Ovr115.F80, Ovr115.F81, Ovr115.F82 and Ovr115.F83 (e.g. which competes for binding or blocks binding of monoclonal antibody Ovr115.A2.1, Ovr115.A11.1, Ovr115.A51.2 (also known as Ovr115 A51.2), Ovr115.A63.2, Ovr115.D3, Ovr115.D15, Ovr115.D20, Ovr115.D26, Ovr115.D31, Ovr115.D32, Ovr115.D34, Ovr115.D37, Ovr115.D43, Ovr115.D51, Ovr115.D69, Ovr115.D71, Ovr115.D81, Ovr115.D84, Ovr115.D94, Ovr115.F2, Ovr115.F3, Ovr115.F4, Ovr115.F5, Ovr115.F6, Ovr115.F7, Ovr115.F8, Ovr115.F9, Ovr115.F10, Ovr115.F11, Ovr115.F13, Ovr115.F14, Ovr115.F15, Ovr115.F19, Ovr115.F20, Ovr115.F21, Ovr115.F22, Ovr115.F23, Ovr115.F24, Ovr115.F25, Ovr115.F26, Ovr115.F28, Ovr115.F29, Ovr115.F30, Ovr115.F31, Ovr115.F32, Ovr115.F33, Ovr115.F34, Ovr115.F35, Ovr115.F36, Ovr115.F37, Ovr115.F38, Ovr115.F39, Ovr115.F40, Ovr115.F41, Ovr115.F42, Ovr115.F43, Ovr115.F46, Ovr115.F47, Ovr115.F49, Ovr115.F50, Ovr115.F51, Ovr115.F53, Ovr115.F54, Ovr115.F55, Ovr115.F56, Ovr115.F57, Ovr115.F58, Ovr115.F59, Ovr115.F60, Ovr115.F61, Ovr115.F62, Ovr115.F63, Ovr115.F64, Ovr115.F65, Ovr115.F66, Ovr115.F67, Ovr115.F69, Ovr115.F70, Ovr115.F71, Ovr115.F72, Ovr115.F73, Ovr115.F74, Ovr115.F75, Ovr115.F76, Ovr115.F77, Ovr115.F78, Ovr115.F79, Ovr115.F80, Ovr115.F81, Ovr115.F82 and Ovr115.F83 to Ovr115), be able to target an Ovr115-expressing tumor cell in vivo and will bind to Ovr115 on a mammalian cell in vivo.

Furthermore, an antibody with the biological characteristic of the Ovr115.A2.1, Ovr115.A11.1, Ovr115.A51.2 (also known as Ovr115 A51.2), Ovr115.A63.2, Ovr115.D3, Ovr115.D15, Ovr115.D20, Ovr115.D26, Ovr115.D31, Ovr115.D32, Ovr115.D34, Ovr115.D37, Ovr115.D43, Ovr115.D51, Ovr115.D69, Ovr115.D71, Ovr115.D81, Ovr115.D84, Ovr115.D94, Ovr115.F2, Ovr115.F3, Ovr115.F4, Ovr115.F5, Ovr115.F6, Ovr115.F7, Ovr115.F8, Ovr115.F9, Ovr115.F10, Ovr115.F11, Ovr115.F13, Ovr115.F14, Ovr115.F15, Ovr115.F19, Ovr115.F20, Ovr115.F21, Ovr115.F22, Ovr115.F23, Ovr115.F24, Ovr115.F25, Ovr115.F26, Ovr115.F28, Ovr115.F29, Ovr115.F30, Ovr115.F31, Ovr115.F32, Ovr115.F33, Ovr115.F34, Ovr115.F35, Ovr115.F36, Ovr115.F37, Ovr115.F38, Ovr115.F39, Ovr115.F40, Ovr115.F41, Ovr115.F42, Ovr115.F43, Ovr115.F46, Ovr115.F47, Ovr115.F49, Ovr115.F50, Ovr115.F51, Ovr115.F53, Ovr115.F54, Ovr115.F55, Ovr115.F56, Ovr115.F57, Ovr115.F58, Ovr115.F59, Ovr115.F60, Ovr115.F61, Ovr115.F62, Ovr115.F63, Ovr115.F64, Ovr115.F65, Ovr115.F66, Ovr115.F67, Ovr115.F69, Ovr115.F70, Ovr115.F71, Ovr115.F72, Ovr115.F73, Ovr115.F74, Ovr115.F75, Ovr115.F76, Ovr115.F77, Ovr115.F78, Ovr115.F79, Ovr115.F80, Ovr115.F81, Ovr115.F82 and Ovr115.F83 antibody will internalize upon binding to Ovr115 on a mammalian cell in vivo.

Likewise, an antibody with the biological characteristic of the Ovr115.A2.1, Ovr115.A11.1, Ovr115.A51.2 (also known as Ovr115 A51.2), Ovr115.A63.2, Ovr115.D3, Ovr115.D15, Ovr115.D20, Ovr115.D26, Ovr115.D31, Ovr115.D32, Ovr115.D34, Ovr115.D37, Ovr115.D43, Ovr115.D51, Ovr115.D69, Ovr115.D71, Ovr115.D81, Ovr115.D84, Ovr115.D94, Ovr115.F2, Ovr115.F3, Ovr115.F4, Ovr115.F5, Ovr115.F6, Ovr115.F7, Ovr115.F8, Ovr115.F9, Ovr115.F10, Ovr115.F11, Ovr115.F13, Ovr115.F14, Ovr115.F15, Ovr115.F19, Ovr115.F20, Ovr115.F21, Ovr115.F22, Ovr115.F23, Ovr115.F24, Ovr115.F25, Ovr115.F26, Ovr115.F28, Ovr115.F29, Ovr115.F30, Ovr115.F31, Ovr115.F32, Ovr115.F33, Ovr115.F34, Ovr115.F35, Ovr115.F36, Ovr115.F37, Ovr115.F38, Ovr115.F39, Ovr115.F40, Ovr115.F41, Ovr115.F42, Ovr115.F43, Ovr115.F46, Ovr115.F47, Ovr115.F49, Ovr115.F50, Ovr115.F51, Ovr115.F53, Ovr115.F54, Ovr115.F55, Ovr115.F56, Ovr115.F57, Ovr115.F58, Ovr115.F59, Ovr115.F60, Ovr115.F61, Ovr115.F62, Ovr115.F63, Ovr115.F64, Ovr115.F65, Ovr115.F66, Ovr115.F67, Ovr115.F69, Ovr115.F70, Ovr115.F71, Ovr115.F72, Ovr115.F73, Ovr115.F74, Ovr115.F75, Ovr115.F76, Ovr115.F77, Ovr115.F78, Ovr115.F79, Ovr115.F80, Ovr115.F81, Ovr115.F82 and Ovr115.F83 antibody will have the same epitope binding, targeting, internalizing, tumor growth inhibitory and cytotoxic properties of the antibody.

The term "antagonist" antibody is used in the broadest sense, and includes an antibody that partially or fully blocks, inhibits, or neutralizes a biological activity of a native Ovr115 protein disclosed herein. Methods for identifying antagonists of an Ovr115 polypeptide may comprise contacting an Ovr115 polypeptide or a cell expressing Ovr115 on the cell surface, with a candidate antagonist antibody and measuring a detectable change in one or more biological activities normally associated with the Ovr115 polypeptide.

An "antibody that inhibits the growth of tumor cells expressing Ovr115" or a "growth inhibitory" antibody is one that binds to and results in measurable growth inhibition of cancer cells expressing or overexpressing Ovr115. Preferred growth inhibitory anti-Ovr115 antibodies inhibit growth of Ovr115-expressing tumor cells e.g., ovarian, pancreatic and colon cancer cells) by greater than 20%, preferably from about 20% to about 50%, and even more preferably, by greater than 50% (e.g. from about 50% to about 100%) as compared to the appropriate control, the control typically being tumor cells not treated with the antibody being tested. Growth inhibition can be measured at an antibody concentration of about 0.1 to 30 pg/ml or about 0.5 nM to 200 nM in cell culture, where the growth inhibition is determined 1-10 days after exposure of the tumor cells to the antibody. Growth inhibition of tumor cells in vivo can be determined in various ways such as is described in the Experimental Examples section below. The antibody is growth inhibitory in vivo if administration of the anti-Ovr115 antibody at about 1 pg/kg to about 100 mg/kg body weight results in reduction in tumor size or tumor cell proliferation within about 5 days to 3 months from the first administration of the antibody, preferably within about 5 to 30 days.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one that overexpresses Ovr115. Preferably the cell is a tumor cell, e.g. an ovarian, pancreatic and colon cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody which induces apoptosis is one which results in about 2 to 50 fold, preferably about 5 to 50 fold, and most preferably about 10 to 50 fold, induction of annexin binding relative to untreated cells in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g. B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or U.S. Pat. No. 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. PNAS (USA) 95:652-656 (1998).

"Fc receptor" or "FcR" describes a receptor that binds to the Fc region of an antibody. The preferred FcR is a native sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126.330-41 (1995). Other FcRs, including those to be identified in the future, are encompassed by the term "FcR" herein. The term also includes the neonatal receptor, FcRn, which is responsible for the transfer, of maternal IgGs to the fetus (Guyer et al., J. Immunol. 117:587 (1976) and Kim et al., J. Immunol. 24:249 (1994)).

"Human effector cells" are leukocytes that express one or more FcRs and perform effector functions. Preferably, the cells express at least FcγRIII and perform ADCC effector function. Examples of human leukocytes that mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g. from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, e.g. as described in Gazzano-Santoro et al., J. Immunol. Methods 202:163 (1996) may be performed.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, brain, as well as head and neck cancer, and associated metastases.

An "Ovr115-expressing cell" is a cell that expresses endogenous or transfected Ovr115 on the cell surface. A "Ovr115-expressing cancer" is a cancer comprising cells that have Ovr115 protein present on the cell surface. A "Ovr115-expressing cancer" produces sufficient levels of Ovr115 on the surface of cells thereof, such that an anti-Ovr115 antibody can bind thereto and have a therapeutic effect with respect to the cancer. A cancer that "overexpresses" Ovr115 is one that has significantly higher levels of Ovr115 at the cell surface thereof, compared to a noncancerous cell of the same tissue type. Such overexpression may be caused by gene amplification or by increased transcription or translation. Ovr115 overexpression may be determined in a diagnostic or prognostic assay by evaluating increased levels of the Ovr115 protein present on the surface of a cell (e.g. via an immunohistochemistry assay; FACS analysis). Alternatively, or additionally, one may measure levels of Ovr115-encoding nucleic acid or MRNA in the cell, e.g. via fluorescent in situ hybridization; (FISH; see WO98/45479 published October, 1998), Southern blotting, Northern blotting, or polymerase chain reaction (PCR) techniques, such as real time quantitative PCR (RT-PCR). One may also study Ovr115 overexpression by measuring shed antigen in a biological fluid such as serum, e.g., using antibody-based assays (see also, e.g., U.S. Pat. No. 4,933,294 issued Jun. 12, 1990; W091/05264 published Apr. 18, 1991; U.S. Pat. No. 5,401,638 issued Mar. 28, 1995; and Sias et al. J. Immunol. Methods 132: 73-80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody. An Ovr115-expressing cancer includes ovarian, pancreatic, lung or breast cancer.

A "mammal" for purposes of treating a cancer or alleviating the symptoms of cancer, refers to any mammal, including humans, domestic and farm animals, and zoo, sports, or pet animals, such as dogs, cats, cattle, horses, sheep, pigs, goats, rabbits, etc. Preferably, the mammal is human.

"Treating" or "treatment" or "alleviation" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an Ovr115-expressing cancer if, after receiving a therapeutic amount of an anti-Ovr115 antibody according to the methods of the present invention, the patient shows observable and/or measurable reduction in or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life issues. To the extent the anti-Ovr115 antibody may prevent growth and/or kill existing cancer cells, it may be cytostatic and/or cytotoxic. Reduction of these signs or symptoms may also be felt by the patient.

The above parameters for assessing successful treatment and improvement in the disease are readily measurable by routine procedures familiar to a physician. For cancer therapy, efficacy can be measured, for example, by assessing the time to disease progression (TTP) and/or determining the response rate (RR).

The term "therapeutically effective amount" refers to an amount of an antibody or a drug effective to "treat" a disease or disorder in a subject or mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See preceding definition of "treating". To the extent the drug may prevent growth and/or kill existing cancer cells, it may be cytostatic and/or cytotoxic.

"Chronic" administration refers to administration of the agent(s) in a continuous mode as opposed to an acute mode, so as to maintain the initial therapeutic effect (activity) for an extended period of time.

"Intermittent" administration is treatment that is not consecutively done without interruption, but rather is cyclic in nature.

Administration "in combination with" one or more further therapeutic agents includes simultaneous (concurrent) and consecutive administration in any order.

"Carriers" as used herein include pharmaceutically acceptable carriers, excipients, or stabilizers, which are nontoxic to the cell or mammal being exposed thereto at the dosages and concentrations, employed.

Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, e.g., gelonin, ricin, saporin, and the various antitumor or anticancer agents disclosed below. Other cytotoxic agents are described below. A tumoricidal agent causes destruction of tumor cells.

A "growth inhibitory agent" when used herein refers to a compound or composition which inhibits growth of a cell, especially an Ovr115-expressing cancer cell, either in vitro or in vivo. Thus, the growth inhibitory agent may be one which significantly reduces the percentage of Ovr115-expressing cells in S phase. Examples of growth inhibitory agents include agents that block cell cycle progression (at a place other than S phase), such as agents that induce GI arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest GI also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (W B Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Label" as used herein refers to a detectable compound or composition that is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition that is detectable.

The term "epitope tagged" used herein refers to a chimeric polypeptide comprising an anti-Ovr115 antibody polypeptide fused to a "tag polypeptide". The tag polypeptide has enough residues to provide an epitope against which an antibody can be made, yet is short enough such that it does not interfere with activity of the Ig polypeptide to which it is fused. The tag polypeptide is also preferably fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

A "small molecule" is defined herein to have a molecular weight below about 500 Daltons.

The term "package insert" is used to refer to instructions customarily included in commercial packages of therapeutic products, that contain information about the indications, usage, dosage, administration, contraindications and/or warnings concerning the use of such therapeutic products.

An "isolated nucleic acid molecule" is a nucleic acid molecule, e.g., an RNA, DNA, or a mixed polymer, which is substantially separated from other genome DNA sequences as well as proteins or complexes such as ribosomes and polymerases, which naturally accompany a native sequence. The term embraces a nucleic acid molecule that has been removed from its naturally occurring environment, and includes recombinant or cloned DNA isolates and chemically synthesized analogues or analogues biologically synthesized by heterologous systems. A substantially pure nucleic acid molecule includes isolated forms of the nucleic acid molecule.

"Vector" includes shuttle and expression vectors and includes, e.g., a plasmid, cosmid, or phagemid. Typically, a plasmid construct will also include an origin of replication (e.g., the ColE1 origin of replication) and a selectable marker (e.g., ampicillin or tetracycline resistance), for replication and selection, respectively, of the plasmids in bacteria. An "expression vector" refers to a vector that contains the necessary control sequences or regulatory elements for expression of the antibodies including antibody fragment of the invention, in prokaryotic, e.g., bacterial, or eukaryotic cells. Suitable vectors are disclosed below.

The cell that produces an anti-Ovr115 antibody of the invention will include the parent hybridoma cell e.g., the hybridomas that are deposited with the ATCC, as well as bacterial and eukaryotic host cells into which nucleic acid encoding the antibodies have been introduced. Suitable host cells are disclosed below.

RNA interference refers to the process of sequence-specific post transcriptional gene silencing in animals mediated by short interfering RNAs (siRNA) (Fire et al., 1998, Nature, 391, 806). The corresponding process in plants is commonly referred to as post transcriptional gene silencing or RNA silencing and is also referred to as quelling in fungi. The process of post transcriptional gene silencing is thought to be an evolutionarily conserved cellular defense mechanism used to prevent the expression of foreign genes which is commonly shared by diverse flora and phyla (Fire et al., 1999, Trends Genet., 15, 358). Such protection from foreign gene expression may have evolved in response to the production of double stranded RNAs (dsRNA) derived from viral infection or the random integration of transposon elements into a host genome via a cellular response that specifically destroys homologous single stranded RNA or viral genomic RNA. The presence of dsRNA in cells triggers the RNAi response though a mechanism that has yet to be fully characterized. This mechanism appears to be different from the interferon response that results from dsRNA mediated activation of protein kinase PKR and 2',5'-oligoadenylate synthetase resulting in non-specific cleavage of MRNA by ribonuclease L.

The presence of long dsRNAs in cells stimulates the activity of a ribonuclease III enzyme referred to as dicer. Dicer is involved in the processing of the dsRNA into short pieces of dsRNA known as short interfering RNAs (siRNA) (Berstein et al., 2001, Nature, 409, 363). Short interfering RNAs derived from dicer activity are typically about 21-23 nucleotides in length and comprise about 19 base pair duplexes. Dicer has also been implicated in the excision of 21 and 22 nucleotide small temporal RNAs (stRNA) from precursor RNA of conserved structure that are implicated in translational control (Hutvagner et al., 2001, Science, 293, 834). The RNAi response also features an endonuclease complex containing a siRNA, commonly referred to as an RNA-induced silencing complex (RISC), which mediates cleavage of single stranded RNA having sequence complementary to the antisense strand of the siRNA duplex. Cleavage of the target RNA takes place in the middle of the region complementary to the antisense strand of the siRNA duplex (Elbashir et al., 2001, Genes Dev., 15, 188).

Short interfering RNA mediated RNAi has been studied in a variety of systems. Fire et al., 1998, Nature, 391, 806, were the first to observe RNAi in *C. Elegans*. Wianny and Goetz, 1999, Nature Cell Biol., 2, 70, describe RNAi mediated by dsRNA in mouse embryos. Hammond et al., 2000, Nature, 404, 293, describe RNAi in *Drosophila* cells transfected with dsRNA. Elbashir et al., 2001, Nature, 411, 494, describe RNAi induced by introduction of duplexes of synthetic 21-nucleotide RNAs in cultured mammalian cells including human embryonic kidney and HeLa cells. Recent work in *Drosophila* embryonic lysates (Elbashir et al., 2001, EMBO J., 20, 6877) has revealed certain requirements for siRNA length, structure, chemical composition, and sequence that are essential to mediate efficient RNAi activity. These studies have shown that 21 nucleotide siRNA duplexes are most active when containing two nucleotide 3'-overhangs. Furthermore, complete substitution of one or both siRNA strands with 2'-deoxy (2'-H) or 2'-O-methyl nucleotides abolishes RNAi activity, whereas substitution of the 3'-terminal siRNA overhang nucleotides with deoxy nucleotides (2'-H) was shown to be tolerated. Single mismatch sequences in the center of the siRNA duplex were also shown to abolish RNAi activity. In addition, these studies also indicate that the position of the cleavage site in the target RNA is defined by the 5'-end of the siRNA guide sequence rather than the 3'-end (Elbashir et al., 2001, EMBO J., 20, 6877). Other studies have indicated that a 5'-phosphate on the target-complementary strand of a siRNA duplex is required for siRNA activity and that ATP is utilized to maintain the 5'-phosphate moiety on the siRNA (Nykanen et al., 2001, Cell, 107, 309).

Studies have shown that replacing the 3'-overhanging segments of a 21-mer siRNA duplex having 2 nucleotide 3' overhangs with deoxyribonucleotides does not have an adverse effect on RNAi activity. Replacing up to 4 nucleotides on each end of the siRNA with deoxyribonucleotides has been reported to be well tolerated whereas complete substitution with deoxyribonucleotides results in no RNAi activity (Elbashir et al., 2001, EMBO J., 20, 6877). In addition, Elbashir et al., supra, also report that substitution of siRNA with 2'-O-methyl nucleotides completely abolishes RNAi activity. Li et al., International PCT Publication No. WO 00/44914, and Beach et al., International PCT Publication No. WO 01/68836 both suggest that siRNA "may include modifications to either the phosphate-sugar back bone or the nucleoside to include at least one of a nitrogen or sulfur heteroatom", however neither application teaches to what extent these modifications are tolerated in siRNA molecules nor provide any examples of such modified siRNA. Kreutzer and Limmer, Canadian Patent Application No. 2,359,180, also describe certain chemical modifications for use in dsRNA constructs in order to counteract activation of double stranded-RNA-dependent protein kinase PKR, specifically 2'-amino or 2'-O-methyl nucleotides, and nucleotides containing a 2'-O or 4'-C methylene bridge. However, Kreutzer and Limmer similarly fail to show to what extent these modifications are tolerated in siRNA molecules nor do they provide any examples of such modified siRNA.

Parrish et al., 2000, Molecular Cell, 6, 1977-1087, tested certain chemical modifications targeting the unc-22 gene in *C. elegans* using long (>25 nt) siRNA transcripts. The authors describe the introduction of thiophosphate residues into these siRNA transcripts by incorporating thiophosphate nucleotide analogs with T7 and T3 RNA polymerase and observed that "RNAs with two (phosphorothioate) modified bases also had substantial decreases in effectiveness as RNAi triggers (data not shown); (phosphorothioate) modification of more than two residues greatly destabilized the RNAs in vitro and we were not able to assay interference activities." Id. at 1081. The authors also tested certain modifications at the 2'-position of the nucleotide sugar in the long siRNA transcripts and observed that substituting deoxynucleotides for ribonucleotides "produced a substantial decrease in interference activity", especially in the case of Uridine to Thymidine and/or Cytidine to deoxy-Cytidine substitutions. Id. In addition, the authors tested certain base modifications, including substituting 4-thiouracil, 5-bromouracil, 5-iodouracil, 3-(aminoallyl) uracil for uracil, and inosine for guanosine in sense and antisense strands of the siRNA, and found that whereas 4-thiouracil and 5-bromouracil were all well tolerated, inosine "produced a substantial decrease in interference activity" when incorporated in either strand. Incorporation of 5-iodouracil and 3-(aminoallyl)uracil in the antisense strand resulted in substantial decrease in RNAi activity as well.

Beach et al., International PCT Publication No. WO 01/68836, describes specific methods for attenuating gene expression using endogenously derived dsRNA. Tuschl et al., International PCT Publication No. WO 01/75164, describes a *Drosophila* in vitro RNAi system and the use of specific siRNA molecules for certain functional genomic and certain therapeutic applications; although Tuschl, 2001, Chem. Biochem., 2, 239-245, doubts that RNAi can be used to cure genetic diseases or viral infection due "to the danger of activating interferon response". Li et al., International PCT Publication No. WO 00/44914, describes the use of specific dsRNAs for use in attenuating the expression of certain target genes. Zernicka-Goetz et al., International PCT Publication No. WO 01/36646, describes certain methods for inhibiting the expression of particular genes in mammalian cells using certain dsRNA molecules. Fire et al., International PCT Publication No. WO 99/32619, describes particular methods for introducing certain dsRNA molecules into cells for use in inhibiting gene expression. Plaetinck et al., International PCT Publication No. WO 00/01846, describes certain methods for identifying specific genes responsible for conferring a particular phenotype in a cell using specific dsRNA molecules. Mello et al., International PCT Publication No. WO 01/29058, describes the identification of specific genes involved in dsRNA mediated RNAi. Deschamps Depaillette et al., International PCT Publication No. WO 99/07409, describes specific compositions consisting of particular dsRNA molecules combined with certain anti-viral agents. Driscoll et al., International PCT Publication No. WO 01/49844, describes specific DNA constructs for use in facilitating gene silencing in targeted organisms. Parrish et al., 2000, Molecular Cell, 6, 1977-1087, describes specific chemically modified siRNA constructs targeting the unc-22 gene of C. elegans. Tuschl et al., International PCT Publication No. WO 02/44321, describe certain synthetic siRNA constructs.

Compositions and Methods of the Invention

The invention provides anti-Ovr115 antibodies. Preferably, the anti-Ovr115 antibodies internalize upon binding to cell surface Ovr115 on a mammalian cell. The anti-Ovr115 antibodies may also destroy or lead to the destruction of tumor cells bearing Ovr115.

It was not apparent that Ovr115 was internalization-competent. In addition the ability of an antibody to internalize depends on several factors including the affinity, avidity, and isotype of the antibody, and the epitope that it binds. We have demonstrated herein that the cell surface Ovr115 is internalization competent upon binding by the anti-Ovr115 antibodies of the invention. Additionally, it was demonstrated that the anti-Ovr115 antibodies of the present invention can specifically target Ovr115-expressing tumor cells in vivo and inhibit or kill these cells. These in vivo tumor targeting, internalization and growth inhibitory properties of the anti-Ovr115 antibodies make these antibodies very suitable for therapeutic uses, e.g., in the treatment of various cancers including ovarian, pancreatic and colon cancer. Internalization of the anti-Ovr115 antibody is preferred, e.g., if the antibody or antibody conjugate has an intracellular site of action and if the cytotoxic agent conjugated to the antibody does not readily cross the plasma membrane (e.g., the toxin calicheamicin). Internalization is not necessary if the antibodies or the agent conjugated to the antibodies do not have intracellular sites of action, e.g., if the antibody can kill the tumor cell by ADCC or some other mechanism.

The anti-Ovr115 antibodies of the invention also have various non-therapeutic applications. The anti-Ovr115 antibodies of the present invention can be useful for diagnosis and staging of Ovr115-expressing cancers (e.g., in radioimaging). They may be used alone or in combination with other ovarian cancer markers, including, but not limited to, CA125, HE4 and mesothelin. The antibodies are also useful for purification or immunoprecipitation of Ovr115 from cells, for detection and quantitation of Ovr115 in vitro, e.g. in an ELISA or a Western blot, to kill and eliminate Ovr115-expressing cells from a population of mixed cells as a step in the purification of other cells. The internalizing anti-Ovr115 antibodies of the invention can be in the different forms encompassed by the definition of "antibody" herein. Thus, the antibodies include full length or intact antibody, antibody fragments, native sequence antibody or amino acid variants, humanized, chimeric or fusion antibodies, immunoconjugates, and functional fragments thereof. In fusion antibodies, an antibody sequence is fused to a heterologous polypeptide sequence. The antibodies can be modified in the Fc region to provide desired effector functions. As discussed in more detail in the sections below, with the appropriate Fc regions, the naked antibody bound on the cell surface can induce cytotoxicity, e.g., via antibody-dependent cellular cytotoxicity (ADCC) or by recruiting complement in complement dependent cytotoxicity, or some other mechanism. Alternatively, where it is desirable to eliminate or reduce effector function, so as to minimize side effects or therapeutic complications, certain other Fc regions may be used.

The antibody may compete for binding, or binds substantially to, the same epitope bound by the antibodies of the invention. Antibodies having the biological characteristics of the present anti-Ovr115 antibodies of the invention are also contemplated, e.g., an anti-Ovr115 antibody which has the biological characteristics of a monoclonal antibody produced by the hybridomas accorded ATCC accession numbers PTA-5202, PTA-5916, PTA-5917, PTA-5918, PTA-5919 and PTA-5920, specifically including the in vivo tumor targeting, internalization and any cell proliferation inhibition or cytotoxic characteristics. Specifically provided are anti-Ovr115 antibodies that bind to an epitope present in amino acids 50-60, 60-70, 70-80, 80-90, 90-100, 100-110, 110-120, 120-130, 130-140, 140-150, 150-160, 160-170, 170-180, 180-190, 190-200, 200-210, 210-220, 220-230, 230-240, 240-250, 250-260, 260-270, 270-280, 280-290, 290-300, 300-310, 310-320, 320-330, 330-340, 340-350, 350-360, 360-370, 370-380, 380-390, 390-400, 400-410, 410-420, 420-430, 430-435 of human Ovr115.

Methods of producing the above antibodies are described in detail below.

The present anti-Ovr115 antibodies are useful for treating an Ovr115-expressing cancer or alleviating one or more symptoms of the cancer in a mammal. Such a cancer includes ovarian, pancreatic and colon cancer, cancer of the urinary tract, lung cancer, breast cancer and prostate cancer. Such a cancer includes more specifically, ovarian serous adenocarcinoma, breast infiltrating ductal carcinoma, prostate adenocarcinoma, renal cell carcinomas, colorectal adenocarcinomas, lung adenocarcinomas, lung squamous cell carcinomas, and pleural mesothelioma. The breast cancer may be HER-2 negative or positive breast cancer. The cancers encompass metastatic cancers of any of the preceding, e.g., ovarian, pancreatic and colon cancer metastases. The antibody is able to bind to at least a portion of the cancer cells that express Ovr115 in the mammal and preferably is one that does not induce or that minimizes HAMA response. Preferably, the antibody is effective to destroy or kill Ovr115-expressing tumor cells or inhibit the growth of such tumor cells, in vitro or in vivo, upon binding to Ovr115 on the cell. Such an antibody includes a naked anti-Ovr115 antibody (not conjugated to any agent). Naked anti-Ovr115 antibodies having tumor growth inhibition properties in vivo include the antibodies described in the Experimental Examples below. Naked antibodies that have cytotoxic or cell growth inhibition properties can be further conjugated with a cytotoxic agent to render them even more potent in tumor cell destruction. Cytotoxic properties can be conferred to an anti-Ovr115 antibody by, e.g., conjugating the antibody with a cytotoxic agent, to form an immunoconjugate as described below. The cytotoxic agent or a growth inhibitory agent is preferably a small molecule. Toxins such as maytansin, maytansinoids, saporin, gelonin, ricin or calicheamicin and analogs or derivatives thereof, are preferable.

The invention provides a composition comprising an anti-Ovr115 antibody of the invention, and a carrier. For the purposes of treating cancer, compositions can be administered to the patient in need of such treatment, wherein the composition can comprise one or more anti-Ovr115 antibodies present as an immunoconjugate or as the naked antibody. Further, the compositions can comprise these antibodies in combination with other therapeutic agents such as cytotoxic or growth inhibitory agents, including chemotherapeutic agents. The invention also provides formulations comprising an anti-Ovr115 antibody of the invention, and a carrier. The formulation may be a therapeutic formulation comprising a pharmaceutically acceptable carrier.

Another aspect of the invention is isolated nucleic acids encoding the internalizing anti-Ovr115 antibodies. Nucleic acids encoding both the H and L chains and especially the hypervariable region residues, chains which encode the native sequence antibody as well as variants, modifications and humanized versions of the antibody, are encompassed.

The invention also provides methods useful for treating an Ovr115-expressing cancer or alleviating one or more symptoms of the cancer in a mammal, comprising administering a therapeutically effective amount of an internalizing anti-Ovr115 antibody to the mammal. The antibody therapeutic compositions can be administered short term (acute) or chronic, or intermittent as directed by physician. Also provided are methods of inhibiting the growth of, and killing an Ovr115 expressing cell. Finally, the invention also provides kits and articles of manufacture comprising at least one antibody of this invention, preferably at least one anti-Ovr115 antibody of this invention that binds to Ovr115 on a mammalian cell in vivo or at least one internalizing anti-Ovr115 antibody of this invention. Kits containing anti-Ovr115 antibodies find use in detecting Ovr115 expression, or in therapeutic or diagnostic assays, e.g., for Ovr115 cell killing assays or for purification and/or immunoprecipitation of Ovr115 from cells. For example, for isolation and purification of Ovr115, the kit can contain an anti-Ovr115 antibody coupled to a solid support, e.g., a tissue culture plate or beads (e.g., sepharose beads). Kits can be provided which contain antibodies for detection and quantitation of Ovr115 in vitro, e.g. in an ELISA or a Western blot. Such antibody useful for detection may be provided with a label such as a fluorescent or radiolabel.

Production of Anti-Ovr115 Antibodies

The following describes exemplary techniques for the production of the antibodies useful in the present invention. Some of these techniques are described further in Example 1. The Ovr115 antigen to be used for production of antibodies may be, e.g., the full length polypeptide or a portion thereof, including a soluble form of Ovr115 lacking the membrane spanning sequence, or synthetic peptides to selected portions of the protein.

Alternatively, cells expressing Ovr115 at their cell surface (e.g. CHO or NIH-3T3 cells transformed to overexpress Ovr115; ovarian, pancreatic, lung, breast or other Ovr115-expressing tumor cell line), or membranes prepared from such cells can be used to generate antibodies. The nucleotide and amino acid sequences of human and murine Ovr115 are available as provided above. Ovr115 can be produced recombinantly in and isolated from, prokaryotic cells, e.g., bacterial cells, or eukaryotic cells using standard recombinant DNA methodology. Ovr115 can be expressed as a tagged (e.g., epitope tag) or other fusion protein to facilitate its isolation as well as its identification in various assays.

Antibodies or binding proteins that bind to various tags and fusion sequences are available as elaborated below. Other forms of Ovr115 useful for generating antibodies will be apparent to those skilled in the art.

Tags

Various tag polypeptides and their respective antibodies are well known in the art. Examples include poly-histidine (poly-his) or poly-histidine-glycine (poly-his-gly) tags; the flu HA tag polypeptide and its antibody 12CA5 (Field et al., Mol. Cell. Biol., 8:2159-2165 (1988)); the c-myc tag and the 8F9, 3C7, 6E10, G4, B7 and 9E10 antibodies thereto (Evan et al., Molecular and Cellular Biology, 5:3610-3616 (1985)); and the Herpes Simplex virus glycoprotein D (gD) tag and its antibody (Paborsky et al., Protein Engineering, 3(6):547-553 (1990)). The FLAG-peptide (Hopp et al., BioTechnology, 6:1204-1210 (1988)) is recognized by an anti-FLAG M2 monoclonal antibody (Eastman Kodak Co., New Haven, Conn.). Purification of a protein containing the FLAG peptide can be performed by immunoaffinity chromatography using an affinity matrix comprising the anti-FLAG M2 monoclonal antibody covalently attached to agarose (Eastman Kodak Co., New Haven, Conn.). Other tag polypeptides include the KT3 epitope peptide [Martin et al., Science, 255:192-194 (1992)]; an α-tubulin epitope peptide (Skinner et al., J. Biol. Chenz., 266:15163-15166 (1991)); and the T7 gene protein peptide tag (Lutz-Freyermuth et al., Proc. Natl. Acad. Sci. USA, 87:6393-6397 (1990)).

Polyclonal Antibodies

Polyclonal antibodies are preferably raised in animals, preferably non-human animals, by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N$=C=NR, where R and $R^1$ are different alkyl groups. Conjugates also can be made in recombinant cell culture as protein fusions.

Animals are immunized against the antigen, immunogenic conjugates, or derivatives by combining, e.g., 5-100 pg of the protein or conjugate (for rabbits or mice, respectively) with 3 volumes of Freund's complete adjuvant and injecting the solution intradermally at multiple sites. One month later, the animals are boosted with ⅕ to ¹⁄₁₀ the original amount of peptide or conjugate in Freund's complete adjuvant by subcutaneous injection at multiple sites. Seven to 14 days later, the animals are bled and the serum is assayed for antibody titer. Animals are boosted until the titer plateaus. Also, aggregating agents such as alum are suitably used to enhance the immune response.

Monoclonal Antibodies

Monoclonal antibodies may be made using the hybridoma method first described by Kohler et al., Nature, 256:495 (1975), or may be made by recombinant DNA methods (U.S. Pat. No. 4,816,567). In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a "fusion partner", e.g., a myeloma cell line using a suitable fusing agent, such as polyethylene glycol, to form a hybridoma cell (Goding, Monoclonal Antibodies. Principles and Practice, pp 103 (Academic Press, 1986)).

The hybridoma cells thus prepared are seeded and grown in a suitable culture medium which medium preferably contains one or more substances that inhibit the growth or survival of the unfused, fusion partner, e.g, the parental myeloma cells. For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-II mouse tumors available from the Salk Institute Cell Distribution Center, San Diego, Calif. USA, and SP-2 and derivatives e.g., X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., Anal. Biochem., 107:220 (1980). Once hybridoma cells that produce antibodies of the desired specificity, affinity, and/or activity are identified, the clones may be subcloned by limiting dilution procedures and grown by standard methods (Goding, Monoclonal Antibodies: Principles and Practice, pp 103 (Academic Press, 1986)). Suitable culture media for this purpose include, for example, D-MEM or RPMI-1640 medium. In addition, the hybridoma cells may be grown in vivo as ascites tumors in an animal e.g, by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transformed or transfected into prokaryotic or eukaryotic host cells such as, e.g., E. coli cells, simian COS cells, Chinese Hamster Ovary (CHO) cells, or myeloma cells, that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Phickthun, Immunol. Revs., 130:151-188 (1992).

Further, the monoclonal antibodies or antibody fragments can be isolated from antibody phage libraries generated using the techniques described in McCafferty et al., Nature, 348: 552-554 (1990). Clackson et al., Nature, 352:624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain (CH and CL) sequences for the homologous murine sequences (U.S. Pat. No. 4,816,567; and Morrison, et al., Proc. Natl Acad. Sci. USA, 81:6851 (1984)), or by fusing the immunoglobulin coding sequence with all or part of the coding sequence for a non-immunoglobulin polypeptide (heterologous polypeptide). The nonimmunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Humanized Antibodies

Methods for humanizing non-human antibodies have been described in the art. Preferably, a humanized antibody has one or more amino acid residues introduced into it from a source which is nonhuman. These non-human amino acid residues are often referred to as "import" residues, which are typically taken from an "import" variable domain. Humanization can be essentially performed following the method of Winter and co-workers (Jones et al., Nature, 321:522-525 (1986); Reichmann et al., Nature, 332:323-327 (1988); Verhoeyen et al., Science, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., J. Immunol., 151:2296 (1993); Chothia et al., J. Mol. Biol., 196:901 (1987)). Another method uses a particular framework region derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art.

Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-Ovr115 antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); U.S. Pat. No. 5,545,807; and Alternatively, phage display technology (McCafferty et al., Nature 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See, also, U.S. Pat. Nos. 5,565,332 and 5,573,905. As discussed above, human antibodies may also be generated by in vitro activated B cells (see U.S. Pat. Nos. 5,567,610 and 5,229,275).

Antibody Fragments

In certain circumstances there are advantages of using antibody fragments, rather than whole antibodies. The smaller size of the fragments allows for rapid clearance, and may lead to improved access to solid tumors. Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments. Antibody fragments can be isolated from the antibody phage libraries discussed above. Alternatively, Fab'-SH fragments can be directly recovered from E. coli and chemically coupled to form F(ab)2 fragments (Carter et al., Bio/Technology 10: 163-167 (1992)). According to another approach, F(ab)2 fragments can be isolated directly from recombinant host cell culture. Fab and F(ab)2 fragment with increased in vivo half-life comprising a salvage receptor binding epitope residues are described in U.S. Pat. No. 5,869,046. Other techniques for the production of antibody fragments will be apparent to the skilled practitioner. The antibody of choice may also be a single chain Fv fragment (scFv). See WO 93/16185; U.S. Pat. No. 5,571,894; and U.S. Pat. No. 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific.

Bispecific Antibodies

Bispecific antibodies are antibodies that have binding specificities for at least two different epitopes. Exemplary bispecific antibodies may bind to two different epitopes of the Ovr115 protein. Other such antibodies may combine an Ovr115 binding site with a binding site for another protein. Alternatively, an anti-Ovr115.Arm may be combined with an arm which binds to a triggering molecule on a leukocyte such as a T cell receptor molecule (e.g. C133), or Fc receptors for IgG (FcγR), such as FcγRI (CD64), FcγRII (CD32) and FcγRIII (CD16), so as to focus and localize cellular defense mechanisms to the Ovr115-expressing cell. Bispecific antibodies may also be used to localize cytotoxic agents to cells which express Ovr115. These antibodies possess an Ovr115-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. F(ab)2 bispecific antibodies). WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region (CHI) containing the site necessary for light chain bonding, present in at least one of the fusions. DNAs encoding the immunoglobulin heavy chain fusions and, if desired, the immunoglobulin light chain, are inserted into separate expression vectors, and are co-trasfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

Preferably, the bispecific antibodies in this approach are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')2 fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., J. Exp. Med., 175: 217-225 (1992) describe the production of a fully humanized bispecific antibody F(ab')2 molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers.

The "diabody" technology described by Hollinger et al., Proc. Natl. Acad. Sci. USA, 90:6444-6448 (1993) has provided an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al. J. Immunol. 147: 60 (1991).

Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1(X1n-VD2-(X2)n-Fc, wherein VDI is a first variable domain, VD2 is a second variable domain, Fc is one polypeptide chain of an Fc region, XI and X2 represent an amino acid or polypeptide, and n is 0 or 1. For instance, the polypeptide chain(s) may comprise: VH-CHI-flexible linker-VH-CHI-Fc region chain; or VH-CHI-VH-CHI-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Other Amino Acid Sequence Modifications

Amino acid sequence modification(s) of the anti-Ovr115 antibodies described herein are contemplated. For example, it may be desirable to improve the binding affinity and/or other biological properties of the antibody. Amino acid sequence variants of the anti-Ovr115 antibody are prepared by introducing appropriate nucleotide changes into the anti-Ovr115 antibody nucleic acid, or by peptide synthesis.

Such modifications include, for example, deletions from, and/or insertions into, and/or substitutions of, residues within the amino acid sequences of the anti-Ovr115 antibody. Any combination of deletion, insertion, and substitution is made to arrive at the final construct, provided that the final construct possesses the desired characteristics. The amino acid changes also may alter post-translational processes of the anti-Ovr115 antibody, such as changing the number or position of glycosylation sites.

A useful method for identification of certain residues or regions of the anti-Ovr115 antibody that are preferred locations for mutagenesis is called "alanine scanning mutagenesis" as described by Cunningham and Wells in Science, 244:1081-1085 (1989). Here, a residue or group of target residues within the anti-Ovr115 antibody are identified (e.g., charged residues such as arg, asp, his, lys, and glu) and replaced by a neutral or negatively charged amino acid (most preferably alanine or polyalanine) to affect the interaction of the amino acids with Ovr115 antigen.

Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at a target codon or region and the expressed anti-Ovr115 antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-Ovr115 antibody with an N-terminal methionyl residue or the antibody fused to a cytotoxic polypeptide. Other insertional variants of the anti-Ovr115 antibody molecule include the fusion to the N- or C-terminus of the anti-Ovr115 antibody to an enzyme (e.g. for ADEPT) or a fusion to a polypeptide which increases the serum half-life of the antibody.

Another type of variant is an amino acid substitution variant. These variants have at least one amino acid residue in the anti-Ovr115 antibody molecule replaced by a different residue. The sites of greatest interest for substitutional mutagenesis include the hypervariable regions, but FR alterations are also contemplated. Conservative substitutions are shown in Table I under the heading of "preferred substitutions". If such substitutions result in a change in biological activity, then more substantial changes, denominated "exemplary substitutions" in Table 1, or as further described below in reference to amino acid classes, may be introduced and the products screened for a desired characteristic.

TABLE I

Amino Acid Substitutions

| Original Residue | Exemplary Substitutions | Preferred Substitutions |
| --- | --- | --- |
| Ala (A) | val; leu; ile | Val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gin; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | Phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, met, ala, val, leu, ile; (2) neutral hydrophilic: cys, ser, thr; (3) acidic: asp, glu; (4) basic: asn, gin, his, lys, arg; (5) residues that influence chain orientation: gly, pro; and (6) aromatic: trp, tyr, phe.

Non-conservative substitutions will entail exchanging a member of one of these classes for another class. Any cysteine residue not involved in maintaining the proper conformation of the anti-Ovr115 antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human Ovr115. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-Ovr115 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared nucleic acid molecule encoding a variant or a non-variant version of the anti-Ovr115 antibody.

It may be desirable to modify the antibody of the invention with respect to effector function, e.g. so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-2922 (1992). Homodimeric antibodies with enhanced anti-tumor activity may also be prepared using heterobifunctional cross-linkers as described in Wolff et al. Cancer Research 53:2560-2565 (1993). Alternatively, an antibody can be engineered which has dual Fc regions and may thereby have enhanced complement lysis and ADCC capabilities. See Stevenson et al. Anti-Cancer Drug Design 3:219-230 (1989).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of the antibody.

Screening for Antibodies with the Desired Properties

Techniques for generating antibodies have been described above. One may further select antibodies with certain biological characteristics, as desired. Desired properties of an anti-Ovr115 antibody include cell growth inhibitory effects, tumor growth inhibitory effects, cell proliferation inhibitory effects, tumor proliferation inhibitory effects, cell killing effects, tumor killing effects, cytostatic effects on tumors, protein function inhibitory effects and removal of protein from cell surface. A highly desired property of an anti-Ovr115 antibody is inhibition of Ovr115 protease activity.

The desired properties of an anti-Ovr115 antibody of the invention listed above, including growth inhibitory effects, may be assessed by methods known in the art, e.g., using cells which express Ovr115 either endogenously or following transfection with the Ovr115 gene. For example, the tumor cell lines and Ovr115-transfected cells provided in Example 1 below may be treated with an anti-Ovr115 monoclonal antibody of the invention at various concentrations for a few days (e.g., 2-7) days and stained with crystal violet or MTT or analyzed by some other calorimetric assay. Another method of measuring proliferation would be by comparing $^3$H-thymidine uptake by the cells treated in the presence or absence an anti-Ovr115 antibody of the invention. After antibody treatment, the cells are harvested and the amount of radioactivity incorporated into the DNA quantitated in a scintillation counter. Appropriated positive controls include treatment of a selected cell line with a growth inhibitory antibody known to inhibit growth of that cell line. Growth inhibition of tumor cells in vivo can be determined in various ways such as is described in the Experimental Examples section below. Preferably, the tumor cell is one that over-expresses Ovr115. Preferably, the anti-Ovr115 antibody will inhibit cell proliferation of an Ovr115-expressing tumor cell in vitro or in vivo by about 25-100% compared to the untreated tumor cell, more preferably, by about 30-100%, and even more preferably by about 50-100% or 70-100%, at an antibody concentration of about 0.5 to 30 µg/ml. Growth inhibition can be measured at an antibody concentration of about 0.5 to 30 µg/ml or about 0.5 nM to 200 nM in cell culture, where the growth inhibition is determined 1-10 days after exposure of the tumor cells to the antibody. The antibody is growth inhibitory in vivo if administration of the anti-Ovr115 antibody at about 1 µg/kg to about 100 mg/kg body weight results in reduction in tumor size or tumor cell proliferation within about 5 days to 3 months from the first administration of the antibody, preferably within about 5 to 30 days.

To select for antibodies which induce cell death, loss of membrane integrity as indicated by, e.g., propidium iodide (PI), trypan blue or 7AAD uptake may be assessed relative to a control. A PI uptake assay can be performed in the absence of complement and immune effector cells. Ovr115-expressing tumor cells are incubated with medium alone or medium containing of the appropriate monoclonal antibody at e.g., about 10 µg/ml. The cells are incubated for a 3 day time period. Following each treatment, cells are washed and aliquoted into 35 mm strainer-capped 12×75 tubes (1 ml per tube, 3 tubes per treatment group) for removal of cell clumps. Tubes then receive PI (10 µg/ml). Samples may be analyzed using a FACSCAN™ flow cytometer and FACSCONVERT™ CellQuest software (Becton Dickinson). Those antibodies which induce statistically significant levels of cell death as determined by PI uptake may be selected as cell death-inducing antibodies.

To screen for antibodies which bind to an epitope on Ovr115 bound by an antibody of interest, e.g., the Ovr115 antibodies of this invention, a routine cross-blocking assay such as that describe in *Antibodies, A Laboratory Manual*, Cold Spring Harbor Laboratory, Ed Harlow and David Lane (1988), can be performed. This assay can be used to determine if a test antibody binds the same site or epitope as an anti-Ovr115 antibody of the invention. Alternatively, or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of Ovr115 can be used in competition assays with the test antibodies or with a test antibody and an antibody with a characterized or known epitope.

For example, a method to screen for antibodies that bind to an epitope which is bound by an antibody this invention may comprise combining an Ovr115-containing sample with a test antibody and an antibody of this invention to form a mixture, the level of Ovr115 antibody bound to Ovr115 in the mixture is then determined and compared to the level of Ovr115 antibody bound in the mixture to a control mixture, wherein the level of Ovr115 antibody binding to Ovr115 in the mixture as compared to the control is indicative of the test antibody's binding to an epitope that is bound by the anti-Ovr115 antibody of this invention. The level of Ovr115 antibody bound to Ovr115 is determined by ELISA. The control may be a positive or negative control or both. For example, the control may be a mixture of Ovr115, Ovr115 antibody of this invention and an antibody known to bind the epitope bound by the Ovr115 antibody of this invention. The anti-Ovr115 antibody labeled with a label such as those disclosed herein. The Ovr115 may be bound to a solid support, e.g., a tissue culture plate or to beads, e.g., sepharose beads.

Immunoconjugates

The invention also pertains to therapy with immunoconjugates comprising an antibody conjugated to an anti-cancer agent such as a cytotoxic agent or a growth inhibitory agent.

Chemotherapeutic agents useful in the generation of such immunoconjugates have been described above. Conjugates of an antibody and one or more small molecule toxins, such as a calicheamicin, maytansinoids, a trichothene, and CC1065, and the derivatives of these toxins that have toxin activity, are also contemplated herein.

Maytansine and Maytansinoids

Preferably, an anti-Ovr115 antibody (full length or fragments) of the invention is conjugated to one or more maytansinoid molecules.

Maytansinoids are mitototic inhibitors which act by inhibiting tubulin polymerization. Maytansine was first isolated from the cast African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

Maytansinoid-Antibody Conjugates

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DMI linked to the monoclonal antibody C242 directed against human colorectal cancer. The conjugate was found to be highly cytotoxic towards cultured colon cancer cells, and showed antitumor activity in an in vivo tumor growth assay. Chari et al. Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansonid drug, which could be increased by increasing the number of maytansinoid molecules per antibody molecule. The A7-maytansinoid conjugate showed low systemic cytotoxicity in mice.

Anti-Ovr115 Antibody-Maytansinoid Conjugates (Immunoconjugates)

Anti-Ovr115 antibody-maytansinoid conjugates are prepared by chemically linking an anti-Ovr115 antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B 1, and Chari et al. Cancer Research 52: 127-131 (1992). The linking groups include disulfide groups, thioether groups, acid labile groups, photolabile groups, peptidase labile groups, or esterase labile groups, as disclosed in the above-identified patents, disulfide and thioether groups being preferred. Conjugates of the antibody and maytansinoid may be made using a variety of bifunctional protein coupling agents such as N-succinimidyl(2-pyridyidithio)propionate (SPDP), succinimidyl-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as his (p-azidobenzoyl)hexanediamine), bis-diazonium derivatives (such as bis-(p-diazoniumbenzoyl)-ethylenediamine), diisocyanates (such as toluene 2,6diisocyanate), and bis-active fluorine compounds (such as 1,5-difluoro-2,4-dinitrobenzene). Particularly preferred coupling agents include N-succinimidyl (2-pyridyldithio)propionate (SPDP) (Carlsson et al., Biochem. J. 173:723-737 [1978]) and N-succinimidyl(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. Preferably, the linkage is formed at the C-3 position of maytansinol or a maytansinol analogue.

Calicheamicin

Another immunoconjugate of interest comprises an anti-Ovr115 antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$, (Hinman et al. Cancer Research 53: 3336 (1993), Lode et al. Cancer Research 5 8: 2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the anti-Ovr115 antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296). Enzymatically active toxins and fragments thereof which can be used include diphtheria A chain, 1 5 nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232 published Oct. 28, 1993. The present invention further contemplates an immunoconjugate formed between an antibody and a compound with nucleolytic activity (e.g. a ribonuclease or a DNA endonuclease such as a deoxyribonuclease; DNase).

For selective destruction of the tumor, the antibody may comprise a highly radioactive atom. A variety of radioactive isotopes are available for the production of radioconjugated anti-Ovr115 antibodies. Examples include $At^{211}$, $I^{131}$, $I^{125}$, $In^{111}$, $Y^{90}$, $Re^{186}$, $Re^{188}$, $Sm^{153}$, $Bi^{212}$, $P^{32}$, and radioactive isotopes of Lu. When the conjugate is used for diagnosis, it may comprise a radioactive atom for scintigraphic studies, for example $Tc^{99M}$ or $I^{123}$, or a spin label for nuclear magnetic resonance (NMR) imaging (also known as magnetic resonance imaging, mri), such as iodine-123, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $Tc^{99M}$, $I^{123}$, $In^{111}$, $Re^{186}$, $Re^{188}$, can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine "Monoclonal Antibodies in Immunoscintigraphy" (Chatal, CRC Press 1989) describes other methods in detail.

Conjugates of the anti-body and cytotoxic agent may be made using a variety of bifunctional protein coupling agents such as N-succinimidyl (2-pyridyldithio) propionate (SPDP), succinimidyl (N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6diisocyanate), and bis-active fluorine compounds (such as 1,5-difluoro-2,4-dinitrobenzene). For example, a ricin immunotoxin can be prepared as described in Vitetta et al. Science 238: 1098 (1987). Carbon labeled 1-isothiocyanatobenzyl methyldiethylene triaminepentaacetic acid (MX-DTPA) is an exemplary chelating agent for conjugation of radionucleotide to the antibody. See WO 94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al. Cancer Research 52: 127-131 (1992); U.S. Pat. No. 5,208, 020) may be used.

Alternatively, a fusion protein comprising the anti-Ovr115 antibody and cytotoxic agent may be made, e.g. by recombinant techniques or peptide synthesis. The length of DNA may comprise respective regions encoding the two portions of the conjugate either adjacent one another or separated by a region encoding a linker peptide which does not destroy the desired properties of the conjugate.

In addition, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

Antibody Dependent Enzyme Mediated Prodrug Therapy (ADEPT)

The antibodies of the present invention may also be used in ADEPT by conjugating the antibody to a prodrug-activating enzyme which converts a prodrug (e.g. a peptidyl chemotherapeutic agent, see W081/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form. Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as O-galactosidase and neuraminidase useful for converting glycosylated prodrugs into free drugs; P-lactamase useful for converting drugs derivatized with P-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, Nature 328: 457-458 (1987)). Antibody-abzyme conjugates can be prepared as described herein for delivery of the abzyme to a tumor cell population. The enzymes of this invention can be covalently bound to the anti-Ovr115 antibodies by techniques well known in the art such as the use of the heterobifunctional crosslinking reagents discussed above.

Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., Nature, 312: 604-608 (1984).

Other Antibody Modifications

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

The anti-Ovr115 antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA, 82:3688 (1985); Hwang et al., Proc. Natl Acad. Sci. USA, 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. J. Biol. Chem. 257: 286-288 (1982) via a disulfide interchange reaction. A chemotherapeutic agent is optionally contained within the liposome. See Gabizon et al. J. National Cancer Inst. 81(19)1484 (1989).

Vectors, Host Cells, and Recombinant Methods

The invention also provides isolated nucleic acid molecule encoding the humanized anti-Ovr115 antibody, vectors and host cells comprising the nucleic acid, and recombinant techniques for the production of the antibody. For recombinant production of the antibody, the nucleic acid molecule encoding it is isolated and inserted into a replicable vector for further cloning (amplification of the DNA) or inserted into a vector in operable linkage with a promoter for expression. DNA encoding the monoclonal antibody is readily isolated and sequenced using conventional procedures (e.g., by using oligonucleotide probes that are capable of binding specifically to nucleic acid molecules encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

Signal Sequence Component

The anti-Ovr115 antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process the native anti-Ovr115 antibody signal sequence, the signal sequence is substituted by a prokaryotic signal sequence selected, for example, from the group of the alkaline phosphatase, penicillinase, 1pp, or heat-stable enterotoxin II leaders. For yeast secretion the native signal sequence may be substituted by, e.g., the yeast invertase leader, oc factor leader (including *Saccharomyces* and *Kluyveromyces* cc-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available. The DNA for such precursor region is ligated in reading frame to DNA encoding the anti-Ovr115 antibody.

Origin of Replication

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the anti-Ovr115 antibody nucleic acid, such as DHFR, thymidine kinase, metallothionein-I and -11, preferably primate metallothionein genes, adenosine deaminase, ornithine decarboxylase, etc. For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding anti-Ovr115 antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow in tryptophan, for example, ATCC No. 44076 or PEP4 Jones, Genetics, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 pm circular plasmid pKDI can be used for transformation of *Kluyveromyces* yeasts. Alternatively, an expression system for large-scale production of recombinant calf chymosin was reported for *K. lactis*. Van den Berg, Bio/Technology, 8:135 (1990). Stable multi-copy expression vectors for secretion of mature recombinant human serum albumin by industrial strains of *Kluyveromyces* have also been disclosed. Fleer et al., Bio/Technology, 9:968-975 (1991).

Promoter Component

Expression and cloning vectors usually contain a promoter that is recognized by the host organism and is operably linked to the anti-Ovr115 antibody nucleic acid. Promoters suitable for use with prokaryotic hosts include the phoA promoter, β-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the anti-Ovr115 antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors. Examples of suitable promoter sequences for use with yeast hosts include the promoters for 3-phosphoglycerate kinase or other glycolytic enzymes, such as enolase, glyceraldehyde phosphate dehydrogenase, hexokinase, pyruvate decarboxylase, phosphofructokinase, glucose phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde phosphate dehydrogenase, and enzymes responsible for maltose and galactose utilization. Suitable vectors and promoters for use in yeast expression are further described in EP 73,657. Yeast enhancers also are advantageously used with yeast promoters.

Anti-Ovr115 antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIll E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human P-interferon cDNA in mouse cells under the control of a thymidine kinase promoter from herpes simplex virus. Alternatively, the Rous Sarcoma Virus long terminal repeat can be used as the promoter.

Enhancer Element Component

Transcription of a DNA encoding the anti-Ovr115 antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the anti-Ovr115 antibody-encoding sequence, but is preferably located at a site 5' from the promoter.

Transcription Termination Component Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding anti-Ovr115 antibody. One useful transcription termination component is the bovine growth hormone polyadenylation region. See WO 94/11026 and the expression vector disclosed therein.

Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W31 10 (ATCC 27,325) are suitable. These examples are illustrative rather than limiting.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789, 199 (Joly et al.), and U.S. Pat. No. 5,840,523 (Simmons et al.) which describes translation initiation region (TIR) and signal sequences for optimizing expression and secretion, these patents incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed e.g, in CHO cells.

In addition to prokaryotes, eukaryotic microbes such as filamentous fungi or yeast are suitable cloning or expression hosts for anti-Ovr115 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183, 070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated anti-Ovr115 antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, *Arabidopsis* and tobacco can also be utilized as hosts. Cloning and expression vectors useful in the production of proteins in plant cell culture are known to those of skill in the art. See e.g. Hiatt et al., Nature (1989) 342: 76-78, Owen et al. (1992) Bio/Technology 10: 790-794, Artsaenko et al. (1995) The Plant J 8: 745-750, and Fecker et al. (1996) Plant Mol Biol 32: 979-986.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CVI ATCC CCL 70); African green monkey kidney cells (VERO-76, ATCC CRL1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, 1413 8065); mouse mammary tumor (MMT 060562, ATCC CCL5 1); TRI cells (Mather et al., Annals N. Y Acad. Sci. 383:44-68 (1982)); MRC 5 cells; FS4 cells; and a human hepatoma line (Hep G2).

Host cells are transformed with the above-described expression or cloning vectors for anti-Ovr115 antibody production and cultured in conventional nutrient media modified as appropriate for inducing promoters, selecting transformants, or amplifying the genes encoding the desired sequences.

Culturing Host Cells

The host cells used to produce the anti-Ovr115 antibody of this invention may be cultured in a variety of media. Commercially available media such as Ham's FIO (Sigma), Minimal Essential Medium (MEM)(Sigma), RPMI-1640 (Sigma), and Dulbecco's Modified Eagle's Medium (DMEM)(Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Purification of Anti-Ovr115 Antibody

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., Bio/Technology 10: 163-167 (1992) describe a procedure for isolating antibodies which are secreted to the periplasmic space of E. coli. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SIDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Pharmaceutical Formulations

Pharmaceutical formulations of the antibodies used in accordance with the present invention are prepared for storage by mixing an antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol, and mcresol); low molecular weight (less than about 10 residues) polypeptides; proteins, such as serum albumin, gelatin, or immunoglobulins; hydrophilic polymers such as polyvinylpyllolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g. Zn-protein complexes); and/or non-ionic surfactants such as TWEEN™, PLURONICS™ or polyethylene glycol (PEG). The antibody preferably comprises the antibody at a concentration of between 5-200 mg/ml, preferably between 10-100 mg/ml.

The formulation herein may also contain more than one active compound as necessary for the particular indication being treated, preferably those with complementary activities that do not adversely affect each other. For example, in addition to the anti-Ovr115 antibody which internalizes, it may be desirable to include in the one formulation, an additional antibody, e.g. a second anti-Ovr115 antibody which binds a different epitope on Ovr115, or an antibody to some other target such as a growth factor that affects the growth of the particular cancer. Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semi-permeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−) hydroxybutyric acid.

The formulations to be used for in vivo administration must be sterile. This is readily accomplished by filtration through sterile filtration membranes.

Methods and Treatment Using Anti-Ovr115 Antibodies

According to the present invention, the anti-Ovr115 antibody that internalizes upon binding Ovr115 on a cell surface is used to treat a subject in need thereof having a cancer characterized by Ovr115-expressing cancer cells, in particular, ovarian, pancreatic, lung or breast cancer, such as ovarian serous adenocarcinoma or breast infiltrating ductal carcinoma cancer, and associated metastases.

The cancer will generally comprise Ovr115-expressing cells, such that the anti-Ovr115 antibody is able to bind thereto. While the cancer may be characterized by overexpression of the Ovr115 molecule, the present application further provides a method for treating cancer which is not considered to be an Ovr115-overexpressing cancer.

This invention also relates to methods for detecting cells which overexpress Ovr115 and to diagnostic kits useful in detecting cells expressing Ovr115 or in detecting Ovr115 in serum from a patient. The methods may comprise combining a cell-containing test sample with an antibody of this invention, assaying the test sample for antibody binding to cells in the test sample and comparing the level of antibody binding in the test sample to the level of antibody binding in a control sample of cells. A suitable control is, e.g., a sample of normal cells of the same type as the test sample or a cell sample known to be free of Ovr115 overexpressing cells. A level of Ovr115 binding higher than that of such a control sample would be indicative of the test sample containing cells that overexpress Ovr115. Alternatively the control may be a sample of cells known to contain cells that overexpress Ovr115. In such a case, a level of Ovr115 antibody binding in the test sample that is similar to, or in excess of, that of the control sample would be indicative of the test sample containing cells that overexpress Ovr115.

Ovr115 overexpression may be detected with a various diagnostic assays. For example, over expression of Ovr115 may be assayed by immunohistochemistry (IHC). Parrafin embedded tissue sections from a tumor biopsy may be subjected to the IHC assay and accorded an Ovr115 protein staining intensity criteria as follows.

Score 0 no staining is observed or membrane staining is observed in less than 10% of tumor cells.

Score 1+ a faint/barely perceptible membrane staining is detected in more than 10% of the tumor cells. The cells are only stained in part of their membrane.

Score 2+ a weak to moderate complete membrane staining is observed in more than 10% of the tumor cells.

Score 3+ a moderate to strong complete membrane staining is observed in more than 10% of the tumor cells.

Those tumors with 0 or 1+ scores for Ovr115 expression may be characterized as not overexpressing Ovr115, whereas those tumors with 2+ or 3+ scores may be characterized as overexpressing Ovr115.

Alternatively, or additionally, FISH assays such as the INFORM™ (sold by Ventana, Arizona) or PATHVISION™ (VySiS, Illinois) may be carried out on formalin-fixed, paraffin-embedded tumor tissue to determine the extent (if any) of Ovr115 overexpression in the tumor. Ovr115 overexpression or amplification may be evaluated using an in vivo diagnostic assay, e.g. by administering a molecule (such as an antibody of this invention) which binds Ovr115 and which is labeled with a detectable label (e.g. a radioactive isotope or a fluorescent label) and externally scanning the patient for localization of the label.

A sample suspected of containing cells expressing or overexpressing Ovr115 is combined with the antibodies of this invention under conditions suitable for the specific binding of the antibodies to Ovr115. Binding and/or internalizing the Ovr115 antibodies of this invention is indicative of the cells expressing Ovr115. The level of binding may be determined and compared to a suitable control, wherein an elevated level of bound Ovr115 as compared to the control is indicative of Ovr115 overexpression. The sample suspected of containing cells overexpressing Ovr115 may be a cancer cell sample, particularly a sample of an ovarian cancer, e.g. ovarian serous adenocarcinoma, or a breast cancer, e.g., a breast infiltrating ductal carcinoma. A serum sample from a subject may also be assayed for levels of Ovr115 by combining a serum sample from a subject with an Ovr115 antibody of this invention, determining the level of Ovr115 bound to the antibody and comparing the level to a control, wherein an elevated level of Ovr115 in the serum of the patient as compared to a control is indicative of overexpression of Ovr115 by cells in the patient. The subject may have a cancer such as e.g., an ovarian cancer, e.g. ovarian serous adenocarcinoma, or a breast cancer, e.g., a breast infiltrating ductal carcinoma.

Currently, depending on the stage of the cancer, ovarian, pancreatic, lung or breast cancer treatment involves one or a combination of the following therapies: surgery to remove the cancerous tissue, radiation therapy, androgen deprivation (e.g., hormonal therapy), and chemotherapy. Anti-Ovr115 antibody therapy may be especially desirable in elderly patients who do not tolerate the toxicity and side effects of chemotherapy well, in metastatic disease where radiation therapy has limited usefulness, and for the management of prostatic carcinoma that is resistant to androgen deprivation treatment. The tumor targeting and internalizing anti-Ovr115 antibodies of the invention are useful to alleviate Ovr115-expressing cancers, e.g., ovarian, pancreatic, lung or breast cancers upon initial diagnosis of the disease or during relapse. For therapeutic applications, the anti-Ovr115 antibody can be used alone, or in combination therapy with, e.g., hormones, antiangiogens, or radiolabelled compounds, or with surgery, cryotherapy, and/or radiotherapy, notably for ovarian, pancreatic, lung or breast cancers, also particularly where shed cells cannot be reached. Anti-Ovr115 antibody treatment can be administered in conjunction with other forms of conventional therapy, either consecutively with, pre- or post-conventional therapy, Chemotherapeutic drugs such as Taxotere® (docetaxel), Taxol® (palictaxel), estramustine and mitoxantrone are used in treating metastatic and hormone refractory ovarian, pancreatic, lung or breast cancer, in particular, in good risk patients. In the present method of the invention for treating or alleviating cancer, in particular, androgen independent and/or metastatic ovarian, pancreatic, lung or breast cancer, the cancer patient can be administered anti-Ovr115 antibody in conjunction with treatment with the one or more of the preceding chemotherapeutic agents. In particular, combination therapy with palictaxel and modified derivatives (see, e.g., EP0600517) is contemplated. The anti-Ovr115 antibody will be administered with a therapeutically effective dose of the chemotherapeutic agent. The anti-Ovr115 antibody may also be administered in conjunction with chemotherapy to enhance the activity and efficacy of the chemotherapeutic agent, e.g., paclitaxel. The Physicians' Desk Reference (PDR) discloses dosages of these agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician.

Particularly, an immunoconjugate comprising the anti-Ovr115 antibody conjugated with a cytotoxic agent may be administered to the patient. Preferably, the immunoconjugate bound to the Ovr115 protein is internalized by the cell, resulting in increased therapeutic efficacy of the immunoconjugate in killing the cancer cell to which it binds. Preferably, the cytotoxic agent targets or interferes with the nucleic acid in the cancer cell. Examples of such cytotoxic agents are described above and include maytansin, maytansinoids, saporin, gelonin, ricin, calicheamicin, ribonucleases and DNA endonucleases.

The anti-Ovr115 antibodies or immunoconjugates are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. The antibodies or immunoconjugates may be injected directly into the tumor mass. Intravenous or subcutaneous administration of the antibody is preferred. Other therapeutic regimens may be combined with the administration of the anti-Ovr115 antibody.

The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

It may also be desirable to combine administration of the anti-Ovr115 antibody or antibodies, with administration of an antibody directed against another tumor antigen associated with the particular cancer. As such, this invention is also directed to an antibody "cocktail" comprising one or more antibodies of this invention and at least one other antibody which binds another tumor antigen associated with the Ovr115-expressing tumor cells. The cocktail may also comprise antibodies that are directed to other epitopes of Ovr115. Preferably the other antibodies do not interfere with the binding and or internalization of the antibodies of this invention.

The antibody therapeutic treatment method of the present invention may involve the combined administration of an anti-Ovr115 antibody (or antibodies) and one or more chemotherapeutic agents or growth inhibitory agents, including co-administration of cocktails of different chemotherapeutic agents. Chemotherapeutic agents include, e.g., estramustine phosphate, prednimustine, cisplatin, 5-fluorouracil, melphalan, cyclophosphamide, hydroxyurea and hydroxyureataxanes (such as paclitaxel and doxetaxel) and/or anthracycline antibiotics. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

The antibody may be combined with an anti-hormonal compound; e.g., an anti-estrogen compound such as tamoxifen; an anti-progesterone such as onapristone (see, EP 616 812); or an anti-androgen such as flutamide, in dosages known for such molecules. Where the cancer to be treated is androgen independent cancer, the patient may previously have been subjected to anti-androgen therapy and, after the cancer becomes androgen independent, the anti-Ovr115 antibody (and optionally other agents as described herein) may be administered to the patient.

Sometimes, it may be beneficial to also co-administer a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy, before, simultaneously with, or post antibody therapy. Suitable dosages for any of the above co-administered agents are those presently used and may be lowered due to the combined action (synergy) of the agent and anti-Ovr115 antibody.

For the prevention or treatment of disease, the dosage and mode of administration will be chosen by the physician according to known criteria. The appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Preferably, the antibody is administered by intravenous infusion or by subcutaneous injections. Depending on the type and severity of the disease, about 1 pg/kg to about 50 mg/kg body weight (e.g. about 0.1-15 mg/kg/dose) of antibody can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of the anti-Ovr115 antibody. However, other dosage regimens may be useful. A typical daily dosage might range from about 1 pg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to the physician or other persons of skill in the art.

Aside from administration of the antibody protein to the patient, the present application contemplates administration of the antibody by gene therapy. Such administration of a nucleic acid molecule encoding the antibody is encompassed by the expression "administering a therapeutically effective amount of an antibody". See, for example, WO 96/07321 published Mar. 14, 1996 concerning the use of gene therapy to generate intracellular antibodies.

There are two major approaches to introducing the nucleic acid molecule (optionally contained in a vector) into the patient's cells; in vivo and ex vivo. For in vivo delivery the nucleic acid molecule is injected directly into the patient, usually at the site where the antibody is required. For ex vivo treatment, the patient's cells are removed, the nucleic acid molecule is introduced into these isolated cells and the modified cells are administered to the patient either directly or, for example, encapsulated within porous membranes which are implanted into the patient (see, e.g. U.S. Pat. Nos. 4,892,538 and 5,283,187). There are a variety of techniques available for introducing nucleic acid molecules into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retroviral vector.

The currently preferred in vivo nucleic acid molecule transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of the currently known gene marking and gene therapy protocols see Anderson et at., Science 256:808-813 (1992). See also WO 93/25673 and the references cited therein.

Articles of Manufacture and Kits

The invention also relates to an article of manufacture containing materials useful for the detection for Ovr115 over-expressing cells and/or the treatment of Ovr115 expressing cancer, in particular ovarian, pancreatic and colon cancer. The article of manufacture comprises a container and a composition contained therein comprising an antibody of this invention. The composition may further comprise a carrier. The article of manufacture may also comprise a label or package insert on or associated with the container. Suitable containers include, for example, bottles, vials, syringes, etc. The containers may be formed from a variety of materials such as glass or plastic. The container holds a composition which is effective for detecting Ovr115 expressing cells and/or treating a cancer condition and may have a sterile access port (for example the container may be an intravenous solution bag or a vial having a stopper pierceable by a hypodermic injection needle). At least one active agent in the composition is an anti-Ovr115 antibody of the invention. The label or package insert indicates that the composition is used for detecting Ovr115 expressing cells and/or for treating ovarian, pancreatic and colon cancer, or more specifically ovarian serous adenocarcinoma, breast infiltrating ductal carcinoma, prostate adenocarcinoma, renal cell carcinomas, colorectal adenocarcinomas, lung adenocarcinomas, lung squamous cell carcinomas, and pleural mesothelioma, in a patient in need thereof. The breast cancer may be HER-2 negative or positive breast cancer. The cancers encompass metastatic cancers of any of the preceding, e.g., ovarian, pancreatic and colon cancer metastases. The label or package insert may further comprise instructions for administering the antibody composition to a cancer patient. Additionally, the article of manufacture may further comprise a second container comprising a substance which detects the antibody of this invention, e.g., a second antibody which binds to the antibodies of this invention. The substance may be labeled with a detectable label such as those disclosed herein. The second container may contain e.g., a pharmaceutically-acceptable buffer, such as bacteriostatic water for injection (BWFI), phosphate-buffered saline, Ringer's solution and dextrose solution. The article of manufacture may further include other materials desirable from a commercial and user standpoint, including other buffers, diluents, filters, needles, and syringes.

Kits are also provided that are useful for various purposes, e.g., for Ovr115 cell killing assays, for purification or immunoprecipitation of Ovr115 from cells or for detecting the presence of Ovr115 in a serum sample or detecting the presence of Ovr115-expressing cells in a cell sample. For isolation and purification of Ovr115, the kit can contain an anti-Ovr115 antibody coupled to a solid support, e.g., a tissue culture plate or beads (e.g., sepharose beads). Kits can be provided which contain the antibodies for detection and quantitation of Ovr115 in vitro, e.g. in an ELISA or a Western blot. As with the article of manufacture, the kit comprises a container and a composition contained therein comprising an antibody of this invention. The kit may further comprise a label or package insert on or associated with the container. The kits may comprise additional components, e.g., diluents and buffers, substances which bind to the antibodies of this invention, e.g., a second antibody which may comprise a label such as those disclosed herein, e.g., a radiolabel, fluorescent label, or enzyme, or the kit may also comprise control antibodies. The additional components may be within separate containers within the kit. The label or package insert may provide a description of the composition as well as instructions for the intended in vitro or diagnostic use.

EXAMPLES

Example 1

Production and Isolation of Monoclonal Antibody Producing Hybridomas

The following MAb/hybridomas of the present invention are described below:

Ovr115.A2.1, Ovr115.A11.1, Ovr115.A51.2 (also known as Ovr115 A51.2), Ovr115.A63.2, Ovr115.D3, Ovr115.D15, Ovr115.D20, Ovr115.D26, Ovr115.D31, Ovr115.D32, Ovr115.D34, Ovr115.D37, Ovr115.D43, Ovr115.D51, Ovr115.D69, Ovr115.D71, Ovr115.D81, Ovr115.D84, Ovr115.D94, Ovr115.F2, Ovr115.F3, Ovr115.F4, Ovr115.F5, Ovr115.F6, Ovr115.F7, Ovr115.F8, Ovr115.F9, Ovr115.F10, Ovr115.F11, Ovr115.F13, Ovr115.F14, Ovr115.F15, Ovr115.F19, Ovr115.F20, Ovr115.F21, Ovr115.F22, Ovr115.F23, Ovr115.F24, Ovr115.F25, Ovr115.F26, Ovr115.F28, Ovr115.F29, Ovr115.F30, Ovr115.F31, Ovr115.F32, Ovr115.F33, Ovr115.F34, Ovr115.F35, Ovr115.F36, Ovr115.F37, Ovr115.F38, Ovr115.F39, Ovr115.F40, Ovr115.F41, Ovr115.F42, Ovr115.F43, Ovr115.F46, Ovr115.F47, Ovr115.F49, Ovr115.F50, Ovr115.F51, Ovr115.F53, Ovr115.F54, Ovr115.F55, Ovr115.F56, Ovr115.F57, Ovr115.F58, Ovr115.F59, Ovr115.F60, Ovr115.F61, Ovr115.F62, Ovr115.F63, Ovr115.F64, Ovr115.F65, Ovr115.F66, Ovr115.F67, Ovr115.F69, Ovr115.F70, Ovr115.F71, Ovr115.F72, Ovr115.F73, Ovr115.F74, Ovr115.F75, Ovr115.F76, Ovr115.F77, Ovr115.F78, Ovr115.F79, Ovr115.F80, Ovr115.F81, Ovr115.F82 and Ovr115.F83. If the MAb has been cloned, it will get the nomenclature "X.1," e.g., the first clone of A7 will be referred to as A7.1, the second clone of A7 will be referred to as A7.2, etc. For the purposes of this invention, a reference to A7 will include all clones, e.g., A7.1, A7.2, etc.

Immunogens and Antigens (Recombinant Proteins, HA & His Tags & Transfected Cells)

Ovr115 Serine Protease Domain Sequence & Protein Production

An Ovr115 (TMPRSS4) construct encoding a tobacco etch virus protease (TEV) recognition site, the serine protease domain of Ovr115 from Val203 to Leu435 was cloned in-frame to the C-terminus of glutathione S-transferase (GST) so that the Ovr115 construct was expressed as a GST-fusion protein of 486 amino acids using standard techniques. Purification of Ovr115 was completed via glutathione sepharose column.

Ovr115 serine protease domain construct amino acid sequence (GST sequence is underlined, TEV sequence is double underlined and tag sequence is in bold type) (SEQ ID NO. 1)

MAPILGYWKIKGLVQPTRLLLEYLEEKYEEHLYERDEGDKWRNKKFELGL

EFPNLPYYIDGDVKLTQSMAIIRYIADKHNMLGGCPKERAEISMLEGAVL

DIRYGVSRIAYSKDFETLKVDFLSKLPEMLKMFEDRLCHKTYLNGDHVTH

PDFMLYDALDVVLYMDPMCLDAFPKLVCFKKRIEAIPQIDKYLKSSKYIA

-continued
WPLQGWQATFGGGDHPPKSDLVPRHNQTSLYKKAGF<u>ENLYFQG</u>VVGGEEA

SVDSWPWQVSIQYDKQHVCGGSILDPHWVLTAAHCFRKHTDVFNWKVRAG

SDKLGSFPSLAVAKIIIIEFNPMYPKDNDIALMKLQFPLTFSGTVRPICL

PFFDEELTPATPLWIIGWGFTKQNGGKMSDILLQASVQVIDSTRCNADDA

YQGEVTEKMMCAGIPEGGVDTCQGDSGGPLMYQSDQWHVVGIVSWGYGCG

GPSTPGVYTKVSAYLNWIYNVWKAELSNWSGPQFEK

Ovr115 Extracellular Fragment Sequence & Protein Production

For immunization of mice and production of MAbs, a recombinant protein fragment of Ovr115 was generated, which constituted only the predicted extracellular portion of the molecule (Lys52-Leu435), in order to select for monoclonal antibodies (MAb), which would bind to the exterior cell surface. An Ovr115 (TMPRSS4) construct encoding a region of Ovr115 from Lys52 to Leu435 was cloned with a six-histidine tag immediately downstream of codon Leu435 and expressed in insect cells using standard baculovirus techniques for production of the D-series MAbs. For production of the F-series of MAbs this protein was cloned into a standard expression vector and expressed in mammalian cells using standard technology. Ovr115 was purified using Ni-NTA resin.

Ovr115 Extracellular Construct (Ovr115 Lys52-Leu435) Amino Acid Sequence (6 His Tag Sequence is in Bold Type) (SEQ ID NO. 2)

MKVILDKYYFLCGQPLHFIPRKQLCDGELDCPLGEDEEHCVKSFPEGPAV

AVRLSKDRSTLQVLDSATGNWFSACFDNFTEALAETACRQMGYSSKPTFR

AVEIGPDQDLDVVEITENSQELRMRNSSGPCLSGSLVSLHCLACGKSLKT

PRVVGGEEASVDSWPWQVSIQYDKQHVCGGSILDPHWVLTAAHCFRKHTD

VFNWKVRAGSKKLGSFPSLAVAKIIIIEFNPMYPKDNDIALMKLQFPLTF

SGTVRPICLPFFDEELTPATPLWIIGWGFTKQNGGKMSDILLQASVQVID

STRCNADDAYQGEVTEKMMCAGIPEGGVDTCQGDSGGPLMYQSDQWHVVG

IVSWGYGCGGPSTPGVYTKVSAYLNWIYNVWKAELHHHHHH

Generation of Stable Ovr115 LMTK Mouse Cell Lines

Full length HA-tagged Ovr115 (Met1-Leu435) was transfected into mouse LMTK cells after cloning into a mammalian vector with an HA tag. Individual clones were checked for expression of Ovr115 by western blot using anti-HA antibody (Covance, Richmond, Calif.), after 1 week in culture.

Ovr115 Transfected LMTK and 293F Amino Acid Sequence (SEQ ID NO. 3)

MDPDSDQPLNSLDVKPLRKPRIPMETFRKVGIPIIIALLSLASSIIIVVV

LIKVILDKYYFLCGQPLHFIPRKQLCDGELDCPLGEDEEHCVKSFPEGPA

VAVRLSKDRSTLQVLDSATGNWFSACFDNFTEALAETACRQMGYSSKPTF

RAVEIGPDQDLDVVEITENSQELRMRNSSGPCLSGSLVSLHCLACGKSLK

TPRVVGGEEASVDSWPWQVSIQYDKQHVDGGSILDPHWVLTAAHCFRKHT

DVFNKWVRAGSDKLGSFPSLAVAKIIIIEFNPMYPKDNDIALMKLQFPLT

-continued
FSGTVRPICLPFFDEELTPATPLWIIGWGFTKQNGGKMSDILLQASVQVI

DSTRCNADDAYSAYLNWIYNVWKAELDPAFLYKVVRSRMASYPYDVPDYA

SL

Generation of Transient 293F Transfected Cells

Ovr115 (SEQ ID NO: 3), was transfected into human 293F cells (Invitrogen) after cloning into the mammalian expression vector PCDNA3.1 vector. Fifty ml of 293F cells cultured in freestyle medium (GIBCO) at 1 million cells/ml were transfected using 293fectin transfection reagent (Invitrogen), according to the manufacturer's guidelines. DNA, 293fectin were mixed in OPTI-MEM medium (GIBCO). Cells were used for analysis 48 h after transfection.

Pro104 (Testisinl Expression Sequences & Protein Production)

Pro104 was used to screen out cross reactive hybridoma clones, since this antigen was also upregulated in ovarian and pancreatic cancers and since it also contained a potentially cross-reactive serine protease domain.

A Pro 104 construct encoding a honey bee melletin secretion signal, a region of Pro104 from Ile42 to Trp297 and a six histidine tag was cloned and expressed using standard techniques. Pro104 was purified using Ni-NTA resin.

Pro104 (Ile42-Trp297) Expressed Amino Acid Sequence (Underlined Portion Represents the Honey Bee Melletin Secretion Signal and the Bold Type Represents the Hexa Histidine Tag) (SEQ ID NO. 4)

<u>MKFLVNVALVFMVVYISYIYADPMA</u>IVGGEDAELGRWPWQGSLRLWDSHV

CGVSLLSHRWALTAAHCFETYSDLSDPSQWMVQFGQLTSMPSFWSLQAYY

TRYFVSNIYLSPRYLGNSPYDIALVKLSAPVTYTKHIQPICLQASTFEFE

NRTDCWVTGWGYIKEDEALPSPHTLQEVQVAIINNSMCNHLFLKYSFRKD

IFGDMVCAGNAQGGKDACFGDSGGPLACNKNGLWYQIGVVSWGVGCGRPN

RPGVYTNISHHFEWIQKLMAQSGMSQPDPSWHHHHHH

Pro104 (Testisin) LMTK Cell Expressed Sequences & Protein Production

A full length construct encoding Pro104 (Met1-Val314) with an HA tag codons located at the C-terminus, downstream from the recombination site was expressed using standard mammalian expression techniques.

Pro104 transfected LMTK amino acid sequence (SEQ ID NO. 5)

MGARGALLLALLLARAGLRKPESQEAAPLSGPCGRRVITSRIVGGEDAEL

GRWPWQGSLRLWDSHVCGVSLLSHRWALTAAHCFETYSDLSDPSGWNVQF

GQLTSMPSFWSLQAYYTRYFVSNIYLSPRYLGNSPYDIALVKLSAPVTYT

KHIQPICLQASTFEFENRTDCWVTGWGYIKEDEASPSPHTLQEVQVAIIN

NSMCNHLFLKYSFRKDIFGDMVCAGNAQGGKDACFGDSGGPLACNKNGLW

YQIGVVSWGVGCGRPNRPGVYTNISHHFEWIQKLMAWSGMSQPDPSWPLL

FFPLLWALPLLGPVDPAFLYKVVRSRMASYPYDVPDYASL

Immunizations

For generation of the A series MAbs mice were immunized with expressed soluble Ovr115 recombinant protein, which corresponded to the serine protease domain (Val203 to Leu435) of the native protein. Groups of 8 BALB/c mice were immunized intradermally in both rear footpads. All injections were 25 uL per foot. The first injection (day 1) of 10 ug of antigen per mouse was in Dulbecco's phosphate buffered saline (DPBS) mixed in equal volume to volume ratio with Titermax gold adjuvant (Sigma, Saint Louis, Mo.). Subsequent injections of 10 ug of antigen per mouse occurred on days 5, 9, 12, 16, 19, 23, 26, 29, 30 and consisted of antigen in 20 uL of DPBS plus 5 uL of Adju-phos adjuvant (Accurate Chemical & Scientific Corp., Westbury, N.Y.) per mouse. The final boost injection on day 33 consisted of antigen diluted in DPBS alone. Fusion occurred on Day 37.

For generation of the D-series and F-series MAbs mice were immunized as above with soluble insect expressed or mammalian expressed Ovr115 recombinant protein (respectively). Both of these proteins corresponded to the entire extracellular domain (Lys52-Leu435) of the native Ovr115 protein, in order to generate MAbs of both in-vivo therapeutic and diagnostic utility.

Hybridoma Fusions

Mice were sacrificed at the completion of the immunization protocol and draining lymph node (popliteal) tissue was collected by sterile dissection. Lymph node cells were dispersed by pressing through a sterile sieve into DMEM and removing T-cells via anti-CD90 (Thy1.2) coated magnetic beads (Miltenyl Biotech, Baraisch-Gladbach, Germany).

These primary B-cell enriched lymph node cells were then immortalized by electro-cell fusion (BTX, San Diego, Calif.) with the continuous myeloma cell line P3x63Ag8.653 (Kearney, J. F. et al., J. Immunology 123: 1548-1550, 1979). Successfully fused cells were selected by culturing in standard Hypoxanthine, Azaserine (HA) (Sigma) containing selection medium (DMEM/10% FBS). These fusion cultures were immediately distributed, 10 million cells per plate, into wells of 96 well culture plates. Distributing the culture in 96 well culture plates, immediately following fusion, facilitated selection of a larger diversity of hybridoma clones producing single, specific antibodies. Supernatants from wells were screened by ELISA, for reactivity against Ovr115 serine protease domain-GST fusion protein, Ovr115 extracellular domain and for no cross-reactivity with the serine protease Pro104 expressed protein.

Monoclonal cultures, consisting of the genetically uniform progeny from single cells, were established after the screening procedure above, by sorting of single viable cells into wells of two 96 well plates, using flow cytometry (Coulter Elite). The resulting murine B-cell hybridoma cultures were expanded using standard tissue culture techniques. Selected hybridomas were cryopreserved in fetal bovine serum (FBS) with 10% DMSO and stored in Liquid Nitrogen at −196° C. to assure maintenance of viable clone cultures.

Screening & Selection of Antibody Producing Hybridomas

Hybridoma cell lines were selected for production of Ovr115 specific antibody by enzyme linked solid phase immunoassay (ELISA). Ovr115 or Pro104 proteins were nonspecifically adsorbed to wells of 96 well polystyrene EIA plates (VWR). Fifty uL of Ovr115 or Pro104 protein at 0.91 mg/mL in (DPBS) was incubated overnight at 4° C. in wells of 96 well polystyrene EIA plates. Plates were washed twice with Tris buffered saline with 0.05% Tween 20, pH 7.4 (TBST). The plate wells were then emptied and nonspecific binding capacity was blocked by completely filling the assay wells with TBST/0.5% bovine serum albumin (TBST/BSA) and incubating for 30 minutes at room temperature (RT). The plate wells were then emptied, 50 μL of hybridoma culture medium samples was added to the wells and incubated for 1 hour at RT. The wells were then washed 3 times with (TBST). One hundred uL of alkaline phosphatase conjugated goat anti-mouse IgG (Fc) (Pierce Chemical Co., Rockford, Ill.), diluted 1:5000 in TBST/BSA, was then added to each well and incubated for 1 hour at RT. The wells were then washed 3 times with TBST. One hundred uL of alkaline phosphatase substrate para-nitrophenylphosphate (pNPP) (Sigma) at 1 mg/mL in 1 M Diethanolamine buffer pH 8.9 (Sigma) was then added to each well and incubated for 20 min. at RT. Bound alkaline phosphatase activity was indicated by the development of a visible yellow color. The enzymatic reaction was quantitated by measuring the solution's absorbance at 405 nm wavelength. Cultures producing the highest absorbance values are chosen for expansion and further evaluation.

ELISA Screening of Ovr115 MAbs

After 2 weeks culture, hybridomas with supernatants producing ELISA absorbance values greater than 1.0 with Ovr115 serine protease domain and less than 0.2 with Pro104 were re-arrayed from twenty-five 96 well culture plates, into new 96 well culture plates and cultured for a further week.

After a further week of culture, 12 hybridomas with supernatants producing ELISA absorbance values greater than 1.0 with Ovr115 serine protease domain (Table 1) and less than 0.2 with Pro104, were selected for single cell cloning into 96 well culture plates, by cell sorting (Coulter Elite).

Results from ELISA Screening of Cloned Ovr115 MAbs

After 2 weeks of culture, supernatants from 2 hybridoma clones from each parent hybridoma were tested for production of ELISA absorbance values greater than 1.5 with Ovr115 and less than 0.2 with Pro104. Clones Ovr115.A2.1, Ovr115 A11.1, Ovr115.A51.2 and Ovr115.A63.2 from the first immunization with Ovr115 serine protease domain and Ovr115.D3, Ovr115.D15, Ovr115.D20, Ovr115.D26, Ovr115.D, 31, Ovr115.D32, Ovr115.D37, Ovr115.D43, Ovr115.D51, Ovr115.D69, Ovr115.D71, Ovr115.D81, Ovr115.D84 Ovr115.F2, Ovr115.F3, Ovr115.F4, Ovr115.F5, Ovr115.F6, Ovr115.F7, Ovr115.F8, Ovr115.F9, Ovr115.F10, Ovr115.F11, Ovr115.F13, Ovr115.F14, Ovr115.F15, Ovr115.F19, Ovr115.F20, Ovr115.F21, Ovr115.F22, Ovr115.F23, Ovr115.F24, Ovr115.F25, Ovr115.F26, Ovr115.F28, Ovr115.F29, Ovr115.F30, Ovr115.F31, Ovr115.F32, Ovr115.F33, Ovr115.F34, Ovr115.F35, Ovr115.F36, Ovr115.F37, Ovr115.F38, Ovr115.F39, Ovr115.F40, Ovr115.F41, Ovr115.F42, Ovr115.F43, Ovr115.F46, Ovr115.F47, Ovr115.F49, Ovr115.F50, Ovr115.F51, Ovr115.F53, Ovr115.F54, Ovr115.F55, Ovr115.F56, Ovr115.F57, Ovr115.F58, Ovr115.F59, Ovr115.F60, Ovr115.F61, Ovr115.F62, Ovr115.F63, Ovr115.F64, Ovr115.F65, Ovr115.F66, Ovr115.F67, Ovr115.F69, Ovr115.F70, Ovr115.F71, Ovr115.F72, Ovr115.F73, Ovr115.F74, Ovr115.F75, Ovr115.F76, Ovr115.F77, Ovr115.F78, Ovr115.F79, Ovr115.F80, Ovr115.F81, Ovr115.F82 and Ovr115.F83, from immunization with either the insect or mammalian expressed entire extracellular domain of Ovr115 were selected for scale up for immunohistochemical, immunofluorescence and functional testing. MAbs were further screened for reactivity with the human serine proteases testisin, pancreatic trypsin, lung tryptase and kallikrein (Cal Biochem, San Diego, Calif.) and plasmin and urokinase (American Diagnostica, Greenwich, Conn.), and mouse testisin, and if reactive with any of these serine protease were excluded from further characterization.

FACS Screening for Cell Surface Binding of Ovr115 MAbs

LMTK-Ovr115-HA stable transfectants stable transfectants were grown in DMEM/10% FBS+P/S. One day prior to staining, the cells were stimulated by adding sodium butyrate to a 5 mM final concentration. LMTK-Ovr115-HA cells were washed once with 10 ml $Ca^{+2}/Mg^{+2}$ free DPBS and then 7 ml of warm (37° C.) Cellstripper (Mediatech, Herndon, Va.) was added per 150 cm² flask. The cells were then incubated for 5 minutes at 37° C. with tapping of the flask to remove tightly attached cells. The cells were removed and pipetted several times to break aggregates, then immediately placed in DMEM/10% FBS/5 mM sodium butyrate. The cells were then centrifuged down for 5 minutes at 1300 rpm and resuspended in DMEM/10% FBS/5 mM sodium butyrate. Human 293F cells were transiently transfected as described above. The cells were incubated at 37° C. for a 30 min. recovery period. Prior to staining, viability of the cells was measured using Guava Viacount (Guava Cytometers, City, Calif.) and if >90% viable they were distributed into 96-well v-bottom plates (VWR) for staining with MAbs.

Cells were aliquoted at 0.5-1.0×10⁶ cells/well in 96-well v-bottom plates and centrifuged for 2 minutes at 1500 rpm. Supernatants were aspirated and plates briefly shaken on a vortex mixer to resuspend the cells, then 200 ul of DPBS/3% FBS/0.01% Na Azide (FACS buffer) was added to each well. Centrifugation and aspiration was repeated, then 25 uL of sequential dilutions of hybridoma supernatant or purified MAb was added to the cells. Plates were stored on ice for 15 min., then washed and centrifuged as above, in 200 uL of FACS buffer. This washing procedure was repeated a twice and then 25 uL of phycoerythrin (PE) conjugated donkey anti-mouse IgG Fc antibody (Jackson ImmunoResearch Laboratories Inc., West Grove, Pa.) was added to cells. After 15 minutes on ice the cells were washed twice, as above and then resuspended in 250 uL of FACS buffer for analysis on the cell sorter or flow cytometer. In certain cases, for storage overnight at 4° C. prior to analysis, 133 ul of FACS buffer and 67 uL of 1% paraformaldehyde/DPBS was added to each well, for fixation, then the volume was increased to 250 uL with DPBS. Stained cells were analyzed on an Elite fluorescent activated cell sorter (FACS) (Beckman-Coulter, Miami, Fla.).

Results demonstrating cell surface binding of several of the D-series and F-series MAbs by FACS analysis, are listed in Tables 1A, B, C and D below. Results of representative experiments demonstrating cell surface expression by FACS analysis are depicted in FIGS. 1A and 1B. Binding of the MAb Ovr115.D3, followed by binding of the donkey anti-mouse Ig-PE conjugate (DAMPE) resulted in 94% of Ovr115 transfected mouse LMTK cells being positive, with a fluorescence intensity (mean fluorescence) 49-fold higher than cells stained with DAMPE alone.

While only Ovr115.D3 and Ovr115.D43 bound significantly to Ovr115 transfected mouse LMTK cells (Table 1A), several more cloned D-series MAbs (Ovr115.D15.3, Ovr115.D32.2, Ovr115.D37.1, Ovr115.D43.1 and Ovr115.D84.2) bound strongly (MFI was from 4 to 76-fold higher than the isotype control) to greater than 50% of Ovr115 transfected 293F cells, but not significantly to the non-transfected 293F cells (Table 1B).

For the F-series MAbs screened against Ovr115 transfected 293F and non-transfected 293F cells (Table 1C), Ovr115.F4, Ovr115.F9, Ovr115.F14, Ovr115.F21, Ovr115.F22, Ovr115.F23, Ovr115.F24, Ovr115.F30, Ovr115.F31, Ovr115.F32, Ovr115.F35, Ovr115.F37, Ovr115.F38, Ovr115.F43, Ovr115.F46, Ovr115.F47, Ovr115.F55, Ovr115.F57, Ovr115.F61, Ovr115.F62, Ovr115.F63, Ovr115.F64, Ovr115.F66, Ovr115.F71, Ovr115.F72, Ovr115.F74, Ovr115.F75, Ovr115.F76, Ovr115.F79 and Ovr115.F83, bound strongly (MFI was from 4 to 131-fold higher than the isotype control) to greater than 50% of Ovr115 transfected 293F cells, but not significantly to the non-transfected 293F cells (Table 1C).

A selected number of the Ovr115 specific D-series and F-series clones, were also tested by FACS for binding to the cell surface of the Ovr115 mRNA positive (QPCR+) tumor cell line A431 (Table 1D).

TABLE 1A

RESULTS OF FACS TESTING Ovr115 D SERIES MAbs on TRANSFECTED LMTK CELLS

| MAb | % Cells Positive | Mean Fluorescence Intensity (MFI) |
| --- | --- | --- |
| DAMPE conjugate | 0.6 | 2.15 |
| Positive control Anti-HA MAb | 61 | 19.0 |
| Ovr115.D3 | 94 | 28.2 |
| Ovr115.D15 | 11 | 4.58 |
| Ovr115.D20 | 80 | 6.35 |
| Ovr115.D34 | 4.3 | 2.53 |
| Ovr115.D43 | 60 | 3.13 |
| Ovr115.D71 | 8.9 | 3.23 |
| Ovr115.D84 | 9.8 | 4.06 |
| Ovr115.D94 | 8.2 | 2.68 |

Table 1A demonstrates that monoclonal antibodies Ovr115.D3 and Ovr115.D20 bound to greater than 50% of the Ovr115-transfected LMTK cells. Additionally, Ovr115.D3 and Ovr115.D20 bound with more than 4-fold higher intensity to Ovr115-transfected 293F cells than non-transfected 293F cells.

Furthermore, Ovr115.D3 bound with about 1.5-fold higher intensity than the positive control anti-HA MAb.

Table 1A results indicate that these MAbs, in particular Ovr115.D3, are suitable for immunotherapy of Ovr115 expressing cells with or without conjugated drugs, toxins, enzymes, prodrug activating molecules or isotopes.

TABLE 1B

RESULTS OF FACS TESTING Ovr115 D SERIES MAb CLONES ON TRANSFECTED 293 CELLS

| | Ovr115-Transfected 293F | | Non-Transfected 293F | |
| --- | --- | --- | --- | --- |
| MAb | % Cells Positive | MFI | % Cells Positive | MFI |
| DAMPE | 1.7 | 0.567 | 1.6 | 0.524 |
| Isotype Control Pro104.D116 | 11.6 | 1.04 | 5.1 | 0.832 |
| Ovr115.D3.3 | 30.3 | 2.02 | 66.1 | 2.43 |
| Ovr115.D15.3 | 89.7 | 14.6 | 12.9 | 0.921 |
| Ovr115.D20.1 | 39.1 | 2.17 | 40.2 | 1.71 |
| Ovr115.D26.1 | 28.9 | 1.68 | 6.1 | 0.786 |
| Ovr115.D31.1 | 39.5 | 2.45 | 4.7 | 0.779 |
| Ovr115.D32.2 | 67.7 | 4.26 | 10.7 | 1.06 |
| Ovr115.D37.1 | 91.1 | 9.27 | 17.7 | 1.28 |
| Ovr115.D43.1 | 92.9 | 12.6 | 14.2 | 1.16 |
| Ovr115.D69.1 | 72.5 | 5 | 54.8 | 2.36 |
| Ovr115.D71.1 | 47.1 | 2.88 | 6.1 | 0.773 |
| Ovr115.D81.3 | 34.8 | 2.33 | 5.3 | 0.786 |
| Ovr115.D84.2 | 97.4 | 76.3 | 5.5 | 0.827 |

Table 1B demonstrates that monoclonal antibodies Ovr115.D15.3, Ovr115.D32.2, Ovr115.D37.1, Ovr115.D43.1 and Ovr115.D84.2 all bound to greater than 50% of the Ovr115-transfected 293F cells. Additionally, Ovr115.D15.3, Ovr115.D32.2, Ovr115.D37.1, Ovr115.D43.1 and Ovr115.D84.2 all bound with more than 4-fold higher intensity to Ovr115-transfected 293F cells than non-transfected 293F cells.

Furthermore, Ovr115.D15.3, Ovr115.D32.2, Ovr115.D37.1, Ovr115.D43.1 and Ovr115.D84.2, all bound with more than 4-fold higher intensity to Ovr115-transfected 293F cells than the negative isotype control.

Table 1B results indicate that these MAbs, in particular Ovr115.D15.3, Ovr115.D32.2, Ovr115.D37.1, Ovr115.D43.1 and Ovr115.D84.2, are suitable for immunotherapy of Ovr115 expressing cells with or without conjugated drugs, toxins, enzymes, prodrug activating molecules or isotopes.

TABLE 1C

RESULTS OF FACS TESTING Ovr115 F SERIES MAbs ON TRANSFECTED 293F CELLS

| MAb | Ovr115-Transfected 293F | | Non-Transfected 293F | |
|---|---|---|---|---|
| | % Cells Positive | MFI | % Cells Positive | MFI |
| Isotype control Pro104.D9.1 | 5.7 | 1.22 | 1.5 | 0.954 |
| Positive control 5E9C11 | 99.4 | 71.1 | 99.8 | 54.3 |
| Ovr115.F2 | 10.4 | 1.53 | 5 | 1.45 |
| Ovr115.F3 | 25.7 | 2.22 | 5.8 | 1.56 |
| Ovr115.F4 | 74.8 | 5.17 | 5.7 | 1.65 |
| Ovr115.F5 | 23.4 | 2.05 | 3 | 1.34 |
| Ovr115.F6 | 41.8 | 2.85 | 4.1 | 1.54 |
| Ovr115.F7 | 11.3 | 1.57 | 5.7 | 1.62 |
| Ovr115.F8 | 38.2 | 2.6 | 8.8 | 1.88 |
| Ovr115.F9 | 69.3 | 8.49 | 4.4 | 1.48 |
| Ovr115.F10 | 9.1 | 1.32 | 6.1 | 1.64 |
| Ovr115.F11 | 7.7 | 1.17 | 6.1 | 1.6 |
| Ovr115.F13 | 32.1 | 2.65 | 6.6 | 1.65 |
| Ovr115.F14 | 95.3 | 117.1 | 4.4 | 1.36 |
| Ovr115.F15 | 35 | 2.51 | 5.4 | 1.45 |
| Ovr115.F19 | 38 | 2.71 | 13.2 | 2.14 |
| Ovr115.F20 | 35.7 | 2.49 | 4.5 | 1.37 |
| Ovr115.F21 | 60.2 | 4.14 | 6.8 | 1.67 |
| Ovr115.F22 | 54.4 | 5.66 | 4.7 | 1.39 |
| Ovr115.F23 | 63.5 | 7.63 | 3 | 1.33 |
| Ovr115.F24 | 56.1 | 4.2 | 4.4 | 1.37 |
| Ovr115.F25 | 7.2 | 1.22 | 3.1 | 1.26 |
| Ovr115.F26 | 8.9 | 1.39 | 5.6 | 1.55 |
| Ovr115.F28 | 72.4 | 7.92 | 23.8 | 2.6 |
| Ovr115.F29 | 40 | 2.62 | 7.7 | 1.68 |
| Ovr115.F30 | 57 | 7.18 | 4 | 1.36 |
| Ovr115.F31 | 59.1 | 5.8 | 12.9 | 2.09 |
| Ovr115.F32 | 61.5 | 4.87 | 9.6 | 1.89 |
| Ovr115.F33 | 57.2 | 3.92 | 17.1 | 2.27 |
| Ovr115.F34 | 27 | 2.31 | 4 | 1.35 |
| Ovr115.F35 | 54.6 | 3.79 | 11.2 | 1.94 |
| Ovr115.F36 | 26.3 | 2.04 | 6.9 | 1.72 |
| Ovr115.F37 | 73.1 | 6.09 | 5.4 | 1.5 |
| Ovr115.F38 | 58 | 8.37 | 7.3 | 1.7 |
| Ovr115.F39 | 38 | 2.71 | 4.2 | 1.37 |
| Ovr115.F40 | 43.8 | 3.2 | 5.8 | 1.55 |
| Ovr115.F41 | 18.2 | 2.01 | 8.5 | 1.72 |
| Ovr115.F42 | 11.3 | 1.63 | 7.2 | 1.67 |
| Ovr115.F43 | 57.4 | 3.8 | 5.2 | 1.47 |
| Ovr115.F46 | 84.5 | 12.6 | 7.7 | 1.72 |
| Ovr115.F47 | 78.9 | 6.52 | 4.8 | 1.5 |
| Ovr115.F49 | 25.1 | 2.31 | 11.4 | 1.92 |
| Ovr115.F50 | 35.2 | 2.85 | 9.3 | 1.822 |
| Ovr115.F51 | 48.2 | 3.1 | 27.9 | 2.81 |
| Ovr115.F53 | 93.8 | 145.1 | 22.5 | 2.52 |
| Ovr115.F54 | 85.8 | 9.37 | 17.4 | 2.13 |
| Ovr115.F55 | 80.4 | 25.1 | 5.2 | 1.48 |
| Ovr115.F56 | 49.5 | 3.78 | 6.1 | 1.56 |
| Ovr115.F57 | 48.3 | 3.76 | 28.6 | 2.79 |
| Ovr115.F58 | 76.8 | 5.28 | 86.8 | 7.07 |
| Ovr115.F59 | 32.9 | 2.66 | 15.8 | 2.3 |
| Ovr115.F60 | 47.9 | 3.74 | 24.3 | 2.71 |
| Ovr115.F61 | 83.8 | 11.5 | 6.7 | 1.58 |
| Ovr115.F62 | 62.7 | 4.44 | 5.7 | 1.54 |
| Ovr115.F63 | 69.8 | 5.47 | 9 | 1.82 |
| Ovr115.F64 | 95.8 | 160.3 | 6.6 | 1.7 |
| Ovr115.F65 | 41.5 | 2.76 | 14.5 | 2 |
| Ovr115.F66 | 50.7 | 3.36 | 9.4 | 1.88 |
| Ovr115.F67 | 66.3 | 7.04 | 14.4 | 2.14 |
| Ovr115.F69 | 76.8 | 22.2 | 32.4 | 2.91 |
| Ovr115.F70 | 36.2 | 2.55 | 5.8 | 1.51 |
| Ovr115.F71 | 92.4 | 104.7 | 6.5 | 1.62 |
| Ovr115.F72 | 73.2 | 9.89 | 7.7 | 1.69 |
| Ovr115.F73 | 22.5 | 2.09 | 7.2 | 1.62 |
| Ovr115.F74 | 95.5 | 117.2 | 8.1 | 1.68 |
| Ovr115.F75 | 93 | 81.3 | 7.1 | 1.64 |
| Ovr115.F76 | 80.4 | 9.19 | 12.2 | 2.02 |
| Ovr115.F77 | 28.2 | 2.3 | 8.4 | 1.79 |
| Ovr115.F78 | 34.2 | 2.68 | 7.3 | 1.6 |
| Ovr115.F79 | 75.5 | 8.44 | 8.4 | 1.73 |
| Ovr115.F80 | 27.2 | 2.24 | 7.5 | 1.72 |
| Ovr115.F81 | 45.3 | 3.48 | 16.5 | 2.17 |
| Ovr115.F82 | 55 | 5.42 | 12.6 | 1.94 |
| Ovr115.F83 | 59.9 | 19.3 | 11 | 4.84 |

Table 1C demonstrates that monoclonal antibodies Ovr115.F4, Ovr115.F9, Ovr115.F14, Ovr115.F21, Ovr115.F22, Ovr115.F23, Ovr115.F24, Ovr115.F28, Ovr115.F30, Ovr115.F31, Ovr115.F32, Ovr115.F33, Ovr115.F35, Ovr115.F37, Ovr115.F43, Ovr115.F46, Ovr115.F47, Ovr115.F53, Ovr115.F54, Ovr115.F55, Ovr115.F61, Ovr115.F62, Ovr115.F63, Ovr115.F64, Ovr115.F69, Ovr115.F71, Ovr115.F72, Ovr115.F74, Ovr115.F75, Ovr115.F76, Ovr115.F79, Ovr115.F82 and Ovr115.F83 all bound to greater than 50% of the Ovr115-transfected 293F cells.

Additionally, Ovr115.F9, Ovr115.F14, Ovr115.F22, Ovr115.F23, Ovr115.F30, Ovr115.F37, Ovr115.F46, Ovr115.F47, Ovr115.F53, Ovr115.F54, Ovr115.F55, Ovr115.F61, Ovr115.F64, Ovr115.F69, Ovr115.F71, Ovr115.F72, Ovr115.F74, Ovr115.F75, Ovr115.F76 and Ovr115.F79 all bound with more than 4-fold higher intensity to Ovr115-transfected 293F cells than non-transfected 293F cells. Moreover, Ovr115.F14, Ovr115.F53, Ovr115.F55, Ovr115.F64, Ovr115.F71, Ovr115.F74 and Ovr115.F75 all bound with more than 15-fold higher intensity to Ovr115-transfected 293F cells than non-transfected 293F cells.

Furthermore, Ovr115.F9, Ovr115.F14, Ovr115.F22, Ovr115.F23, Ovr115.F30, Ovr115.F37, Ovr115.F46, Ovr115.F47, Ovr115.F53, Ovr115.F54, Ovr115.F55, Ovr115.F61, Ovr115.F64, Ovr115.F69, Ovr115.F71, Ovr115.F72, Ovr115.F74, Ovr115.F75, Ovr115.F76 and Ovr115.F79 all bound with more than 4-fold higher intensity to Ovr115-transfected 293F cells than the negative isotype control. Moreover, Ovr115.F14, Ovr115.F53, Ovr115.F55, Ovr115.F64, Ovr115.F71, Ovr115.F74 and Ovr115.F75 all bound with more than 15-fold higher intensity to Ovr115-transfected 293F cells than the negative isotype control.

Table 1C results indicate that these MAbs, in particular Ovr115.F14, Ovr115.F53, Ovr115.F55, Ovr115.F64, Ovr115.F71, Ovr115.F74 and Ovr115.F75 are suitable for immunotherapy of Ovr115 expressing cells with or without conjugated drugs, toxins, enzymes, prodrug activating molecules or isotopes.

TABLE 1D

RESULTS OF FACS TESTING Ovr115 D AND F SERIES
MAbs 0N A431 QPCR(+) TUMOR CELL LINE

| MAb | A431 cells % Cells Positive | MFI |
|---|---|---|
| No MAb | 0.5 | 0.401 |
| DAMPE | 1.3 | 0.442 |
| Isotype control Pro104.D9.1 | 4.5 | 0.589 |
| Ovr115.D15.3 | 6.4 | 0.625 |
| Ovr115.D20.1 | 58.4 | 1.91 |
| Ovr115.D31.1 | 8.3 | 0.637 |
| Ovr115.D32.2 | 7 | 0.633 |
| Ovr115.D43.1 | 4 | 0.531 |
| Ovr115.D84.2 | 34.1 | 1.26 |
| Ovr115.F9.2 | 3.9 | 0.557 |
| Ovr115.F21.1 | 6 | 0.649 |
| Ovr115.F30.1 | 86.3 | 3.78 |
| Ovr115.F32.2 | 12 | 0.762 |
| Ovr115.F55.2 | 14.4 | 0.848 |
| Ovr115.F64.2 | 3.8 | 0.544 |
| Ovr115.F75.1 | 87.4 | 4.07 |
| Ovr115.F76.2 | 95.4 | 7.66 |
| Ovr115.F79.2 | 4.2 | 0.57 |

Table 1D demonstrates that monoclonal antibodies Ovr115.D20.1, Ovr115.F30.1, Ovr115.F75.1 and Ovr115.F76.2 all bound to greater than 50% of the A431 tumor cells. Additionally, Ovr115.D84.2 bound to greater than 30% of the A431 tumor cells.

Furthermore, Ovr115.F30.1, Ovr115.F75.1 and Ovr115.F76.2, all bound with more than 6-fold higher intensity than the negative isotype control.

Table 1D results indicate that these MAbs, in particular Ovr115.F30.1, Ovr115.F75.1 and Ovr115.F76.2, are suitable for immunotherapy of tumors with or without conjugated drugs, toxins, enzymes, prodrug activating molecules or isotopes.

Ovr115 MAb Isotypes

The isotypes of the MAbs were determined using commercially available mouse monoclonal antibody isotyping immunoassay test kits (IsoStrip, Roche Diagnostic Corp., Indianapolis, Ind.). Results of the isotyping are listed in Table 2.

TABLE 2

Ovr115 MAb ISOTYPES

| Clone | Antibody Isotype |
|---|---|
| Ovr115.A2.1 | IgG2b - Kappa |
| Ovr115.A11.1 | IgG2b - Kappa |
| Ovr115.A51.2 | IgG1 - Kappa |
| Ovr115.A52.1 | IgG2a - Kappa |
| Ovr115.A63.2 | IgG2b - Kappa |
| Ovr115.D3.3 | IgG1 - Kappa |
| Ovr115.D15.3 | IgG1 - Kappa |
| Ovr115.D20.1 | IgG1 - Kappa |
| Ovr115.D26.1 | IgG1 - Kappa |
| Ovr115.D31.2 | IgG1 - Kappa |
| Ovr115.D37.1 | IgG3 - Kappa |
| Ovr115.D43.1 | IgG1 - Kappa |
| Ovr115.D71.1 | IgG1 - Kappa |
| Ovr115.D84.2 | IgG1 - Kappa |
| Ovr115.F21.1 | IgG1 - Kappa |
| Ovr115.F30.1 | IgG1 - Kappa |
| Ovr115.F76.2 | IgG1 - Kappa |

Ovr115 MAb Affinity Analysis

Binding kinetics and affinity constants were calculated from surface plasmon resonance measurements using a BIA-CORE 3000 instrument (Biacore, Piscataway, N.J.). Experiments were designed to simultaneously generate on rate, off rate, and affinity values for the Ovr115 MAbs.

Rabbit anti-mouse IgG Fc antibody (Biacore) was immobilized on flow cells 2, 3, and 4 of a CM5 sensor chip (Biacore) by standard amine coupling (Biacore). Flow cell one was used as a blank surface for reference subtractions, and was activated and then inactivated with ethanolamine. Ovr115 MAbs were captured on the rabbit anti-mouse-IgG Fc coated chip, followed by binding of the antigen. Therefore these measurements should represent real 1:1 affinities and not avidity effects that are observed with direct antigen immobilizations, due to the divalent nature of IgG antibodies. MAbs were diluted in HBS EP buffer (Biacore) to 15 ug/mL and were divided into multiple tubes to minimize evaporation between cycles. The MAbs were passed through the flow cells for 2 minutes at 20 uL/minute. The MAb capture level ranged between 200 and 300 response units (RU) per flow cell. Following MAb capture the surface was allowed to stabilize for 3 minutes. Ovr115B (1.56 mg/mL) antigen was then flowed over the captured MAbs at 20 uL/minute in flow cells and through the blank flow cell, for 4 minutes, at successive concentrations of 144, 72, 36, 18, 9, 4.5 ug/mL. Since the Ovr115 molecular weight is 35 kD these antigen concentrations correspond to 4.11, 2.06, 1.03, 0.514, 0.257, 0.129 uM. Two replicates cycles were performed for each antigen concentration or buffer. A dissociation time of 420 seconds was allowed between cycles and regeneration of the chip surfaces to anti-mouse IgG Fc antibody or blank surface, were performed by flowing 100 mM Glycine pH 1.75 through the flow cells for 30 seconds at 100 uL/minute.

The resulting data were analyzed by BiaEvaluation software (Biacore) using a global fit simultaneous ka/kd assuming Langmuir binding. The Rmax parameter of the software was set to local to allow compensation for minor variations in the anti-mouse IgG Fc capture step. The calculated affinities presented in Table 3, which are in the $10^{-8}$ to $10^{-9}$ M range, are sufficiently high to achieve a therapeutic dose in-vivo at less than or equal to 10 mg/kg.

TABLE 3

Ovr115 MAb AFFINITIES

| MAb Clone | Dissociation Constant (Avidity) KD (M) | off rate kd (1/s) | Association constant KA (1/M) | Association rate ka (1/Ms) |
|---|---|---|---|---|
| Ovr115.A2.1 | 7.43E − 09 | 4.04E − 04 | 2.22E + 08 | 8.99E + 04 |
| Ovr115.A11.1 | 1.23E − 08 | 9.53E − 04 | 1.08E + 08 | 1.03E + 05 |
| Ovr115.A63.2 | 8.11E − 09 | 5.20E − 04 | 1.54E + 08 | 8.00E + 04 |

Western Blots

Protein extracts for western blot analysis were prepared in cell lysis buffer (1% NP-40, 10 mM Sodium Phosphate pH 7.2, 150 mM Sodium Chloride) from Ovr115-293T transient transfectants and mammalian adenocarcinoma cell lines. Proteins were separated by electrophoresis on NuPAGE 4-12% Bis-Tris gels (Invitrogen Life Technologies, Carlsbad, Calif.) under denaturing conditions in Novex-XCell II Minicell gel apparatus (Invitrogen, Life Tech) and subsequently transferred to PVDF membranes using an XCell II Blot Module (Invitrogen Life Technologies). Following the transfer of proteins, the membranes were blocked in 1% blocking reagent (Cat#1 096 176, Roche Diagnostic Corp., Indianapolis, Ind.) and incubated overnight at 4° C. with purified primary antibodies (Ovr115 monoclonal antibodies: A2.1, A11.1, A51.2, A52.1 and A63.2) and then with horseradish-peroxidase conjugated goat anti-mouse IgG (Cat.#115-036-062, Jackson ImmunoResearch Laboratories, Inc.) and finally visualized by chemiluminescence using an ECL advance western blotting detection kit (Cat. #RPN2135, Amersham Biosciences, Piscataway, N.J.).

Deglycosylation experiments were performed on protein extracts from Ovr115-293T transfectants using Peptide N-Glycosidase F (PNGaseF, Cat#P0704S, New England Biolabs, Inc, Beverly, Mass.) as per the directions provided by the manufacturer. The deglycosylated samples were then analyzed by western blotting as described above. Briefly, 100 ug of protein extract was denatured in glycoprotein denaturing buffer/0.5% SDS/1% beta-mercaptoethanol, at 100° C. for 10 mins. This was followed by the addition of kit reaction buffers (New England Biolabs) at a final concentration of 1% NP-40 and 50 mM sodium phosphate before the addition of 100 units of PNGase F and incubated at 37° C. for 4 hours.

Results of the western blot experiments are summarized in Table 4. As described, the Ovr115 MAbs A2.1, A11.1, A51.2 and A63.2 specifically detect two major bands of approximately 50 kDa and 28 kDa from total cell lysates of Ovr115-293T transfectants. In a denaturing SDS-PAGE gel, these two bands represent the predicted full length form and the cleaved activated serine protease subunit of the Ovr115 protein respectively. Ovr115 Mab A52.1 did not detect any specific protein bands and was therefore eliminated from further studies. Since the full length form of Ovr115 observed in the SDS-PAGE was larger than the predicted molecular weight of ~48 kDa, we deglycosylated whole cell lysates of Ovr115 transfected 293T cells with PNGase F. This treatment shifted the migration of full length Ovr115 protein from ~50 kDa to ~48 kDa as detected by Ovr115 Mabs A51.2 and A63.2. Deglycosylation did not affect the molecular weight of the 28 kDa protein. This is consistent with the observation that no predicted N-glycosylation sites are present in the serine-protease catalytic subunit of Ovr115.

Expression of Ovr115 was analyzed in pancreatic adenocarcinoma cell lines MiaPaca2, Panc1, PLA5 as well as in colon adenocarcinoma cell line HCT116. A band of ~28 kDa was observed in MiaPaca2 which was absent in the rest of the cell lines analyzed. This directly correlates with data obtained from immunofluorescence studies (Example 2) wherein the highest degree of internalization of Mab A51.2 was observed in MiaPaca2 cell lines with little or none observed in the rest of the cell lines analyzed in this study.

TABLE 4

| | MAb | | | | |
|---|---|---|---|---|---|
| | Ovr115.A2.1 | Ovr115.A11.1 | Ovr115.A51.2 | Ovr115.A52.2 | Ovr115.A63.2 |
| Ovr115-293T | +<br>2 bands at ~50kDa and ~28kDa. Minor band at ~26kDa | +<br>2 bands at ~50kDa and ~28kDa | ++<br>2 bands at ~50kDa and ~28kDa | −<br>non-specific eliminated from further analysis | +<br>2 bands at ~50kDa and ~28kDa. Minor band at ~26kDa |
| Deglycosylated Ovr115-293T | | | 50kDa band shifted to ~48kDa. 28kDa band unchanged | | 50kDa band shifted to ~48kDa. 28kDa band unchanged |
| MiaPaca2 Panc1, PL45 HCT116 | | | 28kDa<br>— | | |

Example 2

Cell Surface Binding of Ovr115 MAbs in Live Cancer Cells Demonstrated by Immunofluorescence The following cancer cell lines were used in this study: ovarian OvCar-3, ovarian CaOV-3, TOV-112D, TOV-21G, SKOV-3; pancreatic MIA Paca-2, AsPC-1, PANC-1, PL-45, CaPan2; colon HCT116, HT29 and breast SKBr-3. Ovarian OvCar-3, ovarian CaOV-3, TOV-112D, TOV-21G, SKOV-3 cells, pancreatic CaPan2 cells, and colon cells HT29 express Ovr115. Control colon HCT116 cells do not express Ovr115.

Cells were seeded on 18 mm glass coverslips and cultured at 37° C. in DMEM containing 10% fetal bovine serum and penicillin and streptomycin for 48 hr prior to treatment with the Ovr115 MAbs.

Ovr115 MAbs of the A-series (Ovr115.A2.1; Ovr115.A11.1; Ovr115.A51.2; Ovr115.A52.1; Ovr115.A63.2), D-series and F-series (Ovr115.F9.2; Ovr115.F21.1; Ovr115.F30.1; Ovr115.F32.2; Ovr115.F55.2; Ovr115.F62.2; Ovr115.F64.2; Ovr115.F74.2; Ovr115.F75.1; Ovr115.F76.2; Ovr115.F79.2) were tested to demonstrate binding of the antibodies to the cell surface of Ovr115 expressing cancer cells by fluorescence microscopy. Primary MAbs were added to the medium at a final concentration of 10 µg/ml and incubated for one hour at 37° C. Following fixation with 3% formaldehyde in Phosphate Buffered Saline (PBS), the cells were incubated with a secondary Cy3-labeled donkey anti-mouse (Jackson ImmunoResearch Laboratories, West Grove, Pa.) at a concentration of 10 µg/ml for 30 min. Following washing, the cells were mounted in Vectastain, a medium containing DAPI (Vector, Burlingame, Calif.) to visualize the cell nuclei and provide a counterstain, and observed in a Zeiss Fluorescence Microscope Axiophot equipped with the appropriate fluorescent filters. Micrographs were obtained with a CCD camera.

Of the five A-series MAbs tested (Ovr115 A2.1; Ovr115 A11.1; Ovr115 A51.2; Ovr115 A52.1; Ovr115 A63.2), four antibodies (Ovr115 A2.1; Ovr115 A11.1; Ovr115 A51.2;

Ovr115 A63.2) demonstrated binding to Ovr115 expressing cells. FIG. 2 shows the binding of Ovr115 A51.2 to the surface of ovarian CaOV-3 cancer cells. Most cells in the field showed specific labeling for Ovr115 could clearly be seen decorating the cell membrane of the cells (arrows).

The D-series MAbs were tested for binding to viable, non-permeabilized Ovr115 transfected 293T cells by fluorescence microscopy. All of the MAbs listed in Table 3A bound to ≧10% of the transfected cells, except Ovr115.D20.1 and Ovr115.D26.1. Furthermore, Ovr115.D15.3, Ovr115.D37.1, Ovr115.D69.1 and Ovr115.D81.3 all bound to greater than 50% of the transfected cells and did not significantly bind to the non-transfected 293T cells. These results are in agreement with the FACS results in Example 1.

Ovr115.D15.3, Ovr115.D20.1, Ovr115.D31.1, Ovr115.D71.1 and Ovr115.D81.3 all bound to between 10 and 50% of cells of the QPCR positive tumor cell line HT29. These results in Table 3B indicate some differences in MAb specificity for recombinantly expressed and tumor expressed Ovr115, which was also in agreement with the FACS results in Example 1.

TABLE 3B

BINDING OF Ovr115 D-SERIES MAbs TO TRANSFECTED 293T CELLS AND mRNA POSITIVE TUMOR CELL LINES BY FLOURESCENCE MICROSCOPY

| | Viable Non-Permeabilized Cells | | | | |
| --- | --- | --- | --- | --- | --- |
| MAb | Ovr115-Transfected 293T | 293T | SKBR3 (QPCR +) | HCT116 (QPCR −) | HT29 (QPCR +) |
| Conjugate | − | − | − | − | − |
| Ovr115.D3.3 | +/++ 1-3% | − | − | − | +/− <1% |
| Ovr115.D15.3 | +/+++ ~40% | − | − | −/+ <5% | +/− >50% |
| Ovr115.D20.1 | + ~1% | − | ±/+ 20-30% | +/− | +/− 10-15% |
| Ovr115.D31.1 | +/+++ 15-20% | +/− | − | − | +/− ~30% |
| Ovr115.D32.2 | +/++ <5% | − | − | − | − |
| Ovr115.D37.1 | +/+ ~40% | − | − | − | − |
| Ovr115.D43.1 | +/++++ < = 5% | − | − | − | − |
| Ovr115.D69.1 | +/+ ~40% | −/+ | − | − | − |
| Ovr115.D71.1 | +/++ < = 5% | −/+ | − | − | +/− ~20% |
| Ovr115.D81.3 | +/+ ~40% | −/+ | − | −/+ | +/− ~30% |
| Ovr115.D84.2 | +/+++ <5% | −/+ | − | − | − |

TABLE 3A

BINDING OF Ovr115 D-SERIES MAbs TO TRANSFECTED 293T CELLS

| | Viable Non-Permeabilized Cells | |
| --- | --- | --- |
| MAb | Ovr115-Transfected 293T | Non-Transfected 293T |
| Ovr110.D3.3 | +/+++, 10-15% | − |
| Ovr110.D15.3 | +/++++, >50% | − |
| Ovr110.D20.1 | +/++, ~5% | − |
| Ovr110.D26.1 | +, <5% | − |
| Ovr110.D31.1 | +/++, ~20% | +/− |
| Ovr110.D32.2 | +/++, ~10% | − |
| Ovr110.D37.1 | +/++, >50% | − |
| Ovr110.D43.1 | +/++++, ~20% | − |
| Ovr110.D69.1 | +/++++, >50% | − |
| Ovr110.D71.1 | +/++++, ~10% | − |
| Ovr110.D81.3 | +/++, >50% | − |
| Ovr110.D84.2 | +/++++, ~20% | − |

The D-series MAbs were further tested by fluorescence microscopy for binding to viable, non-permeabilized Ovr115 transfected 293T cells and to tumor cell lines that are either QPCR positive (+) or negative (−) for Ovr115 mRNA. Table 3B shows that Ovr115.D15.3, Ovr115.D37.1, Ovr115.D69.1 and Ovr115.D81.3 all bound to a significant proportion of the transfected cells and did not significantly bind to the non-transfected 293T cells.

Despite not demonstrating significant binding to Ovr115-transfected 293T cells, Ovr115.D20.1 bound to 20-30% of the QPCR positive tumor cell line SKBR3. Additionally, The F-series MAbs were tested by fluorescence microscopy for binding to tumor cell lines that are either QPCR positive (+) or negative (−) for Ovr115 mRNA. Table 3C shows Ovr115.F64.2, Ovr115.F74.2, Ovr115.F75.1 and Ovr115.F76.2 all bound to between 20 and 100% of the two QPCR positive tumor cells (HT29 and CaPan2), but not to the QPCR negative cell line HCT116. Additionally, the immunofluorescence data in Table 3C complements the FACS data in Example 1. Specifically that Ovr115.F75.1 and Ovr115.76.2 demonstrated strongly positive results for binding to the QPCR positive tumor cell line A431.

TABLE 3C

BINDING OF Ovr115 F-SERIES MAbs TO mRNA POSITIVE TUMOR CELL LINES BY FLOURESCENCE MICROSCOPY

| | Viable Non-Permeabilized Cells | | |
| --- | --- | --- | --- |
| MAb | HCT116 (QPCR −) | HT29 (QPCR +) | CaPAN2 (QPCR +) |
| Conjugate | − | − | − |
| Ovr115.F9.2 | − | − | − |
| Ovr115.F21.1 | − | − | − |
| Ovr115.F30.1 | − | − | − |
| Ovr115.F32.2 | − | − | − |
| Ovr115.F55.2 | − | − | − |
| Ovr115.F62.2 | − | − | − |
| Ovr115.F64.2 | − | +/− 40% | +/+, 100% |
| Ovr115.F74.2 | − | +/+ ~40% | +/+, 70-80% |
| Ovr115.F75.1 | − | +/− 20-30% | +/+, 70-80% |
| Ovr115.F76.2 | − | +/+ 100% | +, >50% |
| Ovr115.F79.2 | − | − | − |

Cell Surface Binding of Ovr115 MAbs in Live Cancer Cells Demonstrated by Immunofluorescence Several of the Ovr115 D-series and F-series MAbs demonstrated cell surface binding to significant numbers of tumor cells expressing Ovr115 mRNA by fluorescence microscopy. The immunofluorescence intensity was sufficient to clearly observe the cell surface binding. This immunofluorescence data demonstrates these MAbs are suitable for immunotherapy of Ovr115 expressing cells with or without conjugated drugs, toxins, enzymes, prodrug activating molecules or isotopes.

Binding and Internalization in Live Cancer Cells

This study was performed using fluorescent antibodies. By labeling antibodies with the fluorescent dye Cy3, antibody binding and internalization can be visualized by fluorescence microscopy. The technology is well established. HCT116 cells that do not express Ovr115 were used as negative controls.

Cy3 Conjugation

Ovr115 A2.1; Ovr115 A11.1; Ovr115 A51.2; Ovr115 A63.2 MAbs were labeled with Cy3. Cy3 conjugation was carried out according to standard procedures and the manufacturer's guidelines. Briefly, 1 mg of antibody was dialyzed against 0.1M bicarbonate buffer (pH 9.3) for 60 min, mixed with Cy3 dye and incubated at RT for 2 hr, and then transferred in a Pierce Slide-A Lyzer Dialysis cassette for dialysis in 2 liters of PBS for 6 hr at 4° C. The operation was repeated 6 times. The Cy3 conjugated antibodies were recovered and concentration was measured in a spectrometer at 280 nm.

Ovr115 A2.1; Ovr115 A11.1; Ovr115 A51.2; Ovr115 A63.2 MAbs were then incubated at a concentration of 10 ug/ml with the cells at 37° C. in a water chamber for 60 min, washed in PBS and fix with 3% formaldehyde in PBS for 10 min. Following fixation, the coverslips with the cells were mounted in a medium containing DAPI (Vectastain) to visualize cell nuclei, and observed in a Zeiss fluorescence Microscope Axiophot equipped with the appropriate fluorescent filters. Micrographs were obtained with a color CCD camera.

Results

Immunofluorescence microscopy of cancer cells treated with Cy3-Ovr115 A2.1; Ovr115 A11.1; Ovr115 A51.2; Ovr115 A63.2 indicated that ovarian and pancreatic cancer cells expressing Ovr115 were able to bind and internalized the fluorescent antibodies to varying extent. FIG. 3A shows the binding of Cy3-A51.2 to the cell surface of ovarian CaOV3 cells, a cell line that expresses Ovr115 (arrows). Numerous internalization vesicles were detected in the cytoplasm of the cells. Cy3-A51.2 did not bind to the non-expressor control cells HCT116 (FIG. 3B). Following binding Cy-Ovr115 A51.2 was internalized by ovarian cancer cells. FIG. 4 shows Cy3-Ovr115A51.2 internalization in ovarian TOV-112D (FIG. 4A) and TOV-21G (FIG. 4B) cancer cells. Numerous internalization vesicles could be seen in the cytoplasm. In addition, a perinuclear labeling corresponding to the presence of endosomes in the vicinity of the Golgi apparatus could be seen (arrows).

FIG. 5 shows the binding (FIG. 5A and FIG. 5C) and internalization of Cy3-A51.2 (FIG. 5B, arrows) in three out of four pancreatic cell lines. The binding pattern corresponded to discrete cell surface domains (FIG. 5A and FIG. 5C, arrows). The internalization pattern staining was characterized by the presence of perinuclear vesicles likely to correspond to endosomes located in the proximity of the Golgi apparatus (FIG. 5B, arrows). Cy3-A51.2 did not bind the pancreatic cell line PL-45, probably because this cell line does not express Ovr115 (FIG. 5D).

Ovr115 MAbs are internalized in vitro upon binding to Ovr115 on the cell surface of Ovr115 expressing cancer cells.

Ovr115 Distribution in Tumors and Normal Tissues Assessed by Immnunohistochemistry:

Tissues: Formalin fixed paraffin embedded blocks of breast, ovarian cancer and normal adjacent tissues were obtained from National Disease Research Interchange (Philadelphia, Pa.). OCT embedded blocks of normal organs were obtained from Zoion (Hawthorne, N.Y.).

Immunohistochemical Staining for Formalin Fixed Paraffin Embedded Sections

Six-μm-thick sections cut from formalin fixed paraffin embedded blocks were baked at 45° C., deparaffinized in Histoclear and rehydrated through a series of ethanol until PBS. Antigen retrieval was performed by boiling the section slides in 10 mM sodium citrate buffer (pH 6.0) at 120° C., 15~17 PSI in decloaking chamber (Biocare, Walnut Creek, Calif.) for 10 min. Endogenous peroxidase activity was quenched by treating with 3% hydrogen peroxide solution for 15 min. Slides were incubated with 1% BSA to block non-specific antibody binding and then reacted with four different primary Ovr115 MAbs used at a concentration of 10 ug/ml for 1 hour in room temperature in a DAKO autostainer (Dako Co., Carpinteria, Calif.). After washing in Tris-Buffered Saline (TBS) with 0.5% Tween-20, slides were incubated with anti-mouse IgG as the secondary antibody conjugated to horse radish peroxidase (HRP). After washing in TBS with 0.5% Tween-20, sections were visualized by 3,3'-diaminobenzidine chromagen for 2~5 minutes (Immunovision Technologies, Co. Daly City, Calif.) and counterstained with hematoxylin before mounting in Permount medium after dehydration. Normal mouse IgG at the same concentration as the primary antibody served as negative controls.

Immunohistochemical Staining for OCT Embedded Frozen Unfixed Sections

Slides were cut in the cryochamber at 5-8 um at an appropriate temperature, air dried for a minimum of thirty minutes at room temperature. Briefly, slides were rinsed in TBS to remove off OCT and incubated at room temperature. IHC was performed using the Immunovision Powervision Kit (Immunovision Technologies, Co. Daly City, Calif.). Briefly, slides were rinsed in TBS-T to remove off OCT and incubated with a series of different primary antibodies to Ovr115 for 1 hour at room temperature. They were then post-fixed in 4% paraformaldehyde fixative for 10 minutes at room temperature and treated as described above.

In some experiments, the sections were treated with a secondary Cy3-labeled donkey anti-mouse (Jackson ImmunoResearch Laboratories, West Grove, Pa.) at a concentration of 10 ug/ml for 30 min. Following washing, the clinical sample slides were mounted in Vectastain, a medium containing DAPI (Vector, Burlingame, Calif.) to visualize the cell nuclei and observed in a Zeiss Fluorescence Microscope Axiophot equipped with the appropriate fluorescent filters. Micrographs were obtained with a CCD camera.

Results

Ovr115.A2.1; Ovr115.A11.1; Ovr115.A51.2; Ovr115.A63.2, Ovr115.D15 and Ovr115.D84 were used to immunolabel sections of ovarian and pancreatic cancer. FIGS. 6 and 7 show the distribution of Ovr115 in ovarian tumors as evaluated by immunofluorescence using Ovr115.A51.2, Ovr115.D15 and Ovr115.D84. The position of the nuclei of the ovarian cancer cells that are stained in FIGS. 6A and 6B are shown in FIGS. 6C and 6D, respectively. In both FIG. 6 and FIG. 7, a strong immunofluorescent signal could be seen on the cell surface of the epithelial cells, indicating that Ovr115 is expressed on the cell surface.

Figure 8A:

FIG. 8A shows the IHC results obtained with Ovr115.D84 in ovarian cancer clinical samples. Three out of five ovarian clinical samples (60%) showed strong labeling on the cell surface of the epithelial cells of the tumor (arrows). No specific labeling was observed when normal mouse IgG was used instead of Ovr115.D84 (FIG. 8B).

Figure 9B:
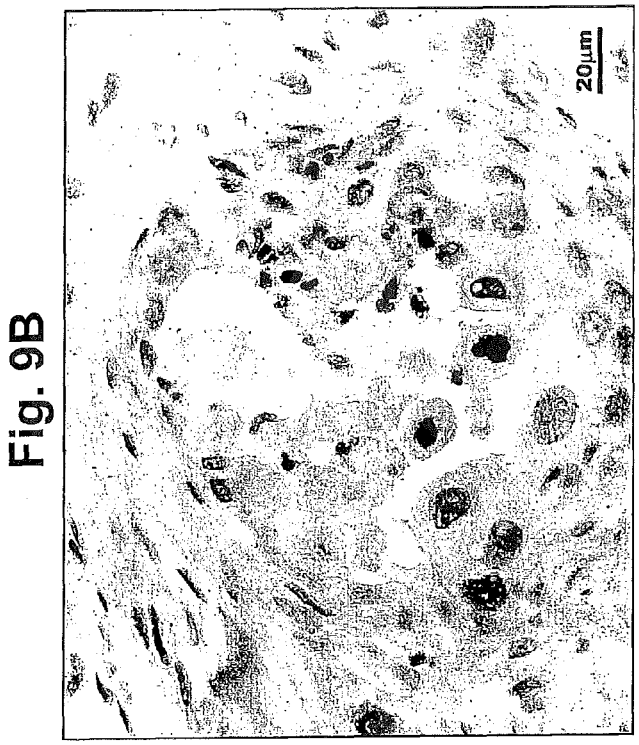
FIG. 9 shows Ovr115 D84 labels epithelial cells in pancreatic cancer tumors.
Figure 9A:

In addition to ovarian cancer, 3 out of 4 pancreatic cancer clinical samples (75%) showed expression of Ovr115. FIG. 9A shows the immunolabeling pattern obtained using Ovr115.D84 in clinical samples of pancreas adenocarcinoma. The labeling was restricted to the cell surface of epithelial cells (arrows). No specific labeling was observed when normal mouse IgG was used instead of Ovr115.D84 (FIG. 9B). FIGS. 10A and 10B demonstrates the labeling of a frozen section from a serous ovarian papillary adenocarcinoma, by Ovr115.D43.1 and the lack of labeling in frozen sections of normal human heart, liver and kidney. The cell membrane of both ovarian and pancreatic epithelial cells was clearly labeled by Ovr115.D84, indicating that, following its synthesis, Ovr115 is transported to the cell surface. Ovr115 expression was also analyzed in normal tissues from a number of vital organs and found to not exceed background.

Further data from examination of frozen sections and sections of fixed, paraffin embedded tissues for labeling with D-series and F-series MAbs are summarized in Tables 4A, 4B, 4C and 4D below.

Ovr115.F75.1, Ovr115.F76.2 and Ovr115.F 79.2 were tested on a more extensive panel of frozen normal tissues (Table 4B, below), at 10 µg/ml, Ovr115.F64.2, Ovr115.F74.2, Ovr115.F75.1, Ovr115.F79.2 again did not exceed background labeling in frozen sections of tissues from normal heart, liver, kidney, stomach, bladder, testis, colon, ovary, prostate, pancreas, lung or breast. Ovr115.F76.2 similarly, had no reactivity in these normal tissues, excepting for a weak labeling of the cytoplasm, but not the cell surface membranes, with a low percentage of cells, in one normal pancreas. Many of these tissues are known to contain related serine proteases, such as corin, hepsin and testisin, which further indicated the high specificity of the Ovr115 F-series MAbs for the Ovr115 protein.

TABLE 4B

RESULTS OF IMMUNOHISTOCHEMICAL SCREENING OF F-SERIES MAbS ON FROZEN SECTIONS FROM NORMAL TISSUES

| | Hrt | Liv | Kid | Sto | Bld | Tes | Col | Ova | Pro | Pan | Lng | Brt |
|---|---|---|---|---|---|---|---|---|---|---|---|---|
| IgG | — | — | — | — | — | — | — | — | — | — | — | — |
| F64.2 | — | — | — | — | — | — | — | — | — | — | — | — |
| F74.2 | — | — | — | — | — | — | — | — | — | — | — | — |
| F75.1 | — | — | — | — | — | — | — | — | — | — | — | — |
| F76.2 | — | — | — | — | — | — | — | — | — | 1 + C 20% | — | — |
| F79.2 | — | — | — | — | — | — | — | — | — | — | — | — |

Ovr115.F64.2, Ovr115.F74.2, Ovr115.F75.1, Ovr115.F76.2 and Ovr115.F 79.2 were then tested in sections from formalin fixed, paraffin embedded (FFPE) tissues and the results are summarized in Table 4C below. Ovr115.F74.2 and Ovr115.F79.2 both reacted with FFPE sections from 2/4 patients with ovarian cancer, but not with FFPE sections from normal organs, excepting for some weak reactivity of Ovr115.F79.2 in cardiac muscle, which may be an artifact of fixation, since labeling was not evident in frozen sections of cardiac muscle. Ovr115.F74.2 and Ovr 115.F76.2 reacted with FFPE sections from 1/4 patients with ovarian cancer, but not with FFPE sections from normal organs.

TABLE 4A

RESULTS OF IMMUNOHISTOCHEMICAL TESTING OF F-SERIES MAbs ON FROZEN SECTIONS FROM NORMAL AND OVARIAN CANCER TISSUES

| | | Normal Tissues | | | | Ovarian Cancers (No. Positive/Total Tested) |
|---|---|---|---|---|---|---|
| | Conc. | Heart | Liver | Kidney | Ovary | |
| IgG | 10 ug/ml | — | — | — | — | |
| F21.1 | 10 ug/ml | — | — | — | — | 2/5 |
| F29.2 | 10 ug/ml | — | — | — | — | 0/5 |
| F30.1 | 10 ug/ml | — | — | — | — | 5/5 |
| F32.2 | 10 ug/ml | — | — | — | — | 5/5 |
| F55.2 | 10 ug/ml | — | — | — | — | 0/5 |
| F62.2 | 10 ug/ml | — | — | — | — | 0/5 |
| F64.2 | 10 ug/ml | — | — | — | — | 2/5 |
| F74.2 | 10 ug/ml | — | — | — | — | 3/5 |
| F75.1 | 10 ug/ml | — | — | — | — | 3/5 |
| F76.2 | 10 ug/ml | — | — | — | — | 1/5 |
| F79.2 | 10 ug/ml | — | — | — | — | 2/5 |

Table 4A shows that Ovr115.F21.1, Ovr15.F30.1, Ovr115.F64.2, Ovr115.F74.2, Ovr115.F75.1, Ovr115.F76.2 and Ovr115.F 79.2 all reacted with frozen sections from ovarian cancer tissues, but not with frozen sections from normal heart, liver, kidney or ovary. In particular, Ovr115.F30.1, Ovr115.F32.2, Ovr115.F74.2 and Ovr115.F75.1 reacted in more than 50% of the ovarian cancer specimens. When Ovr115.F64.2, Ovr115.F74.2,

TABLE 4C

RESULTS OF IMMUNOHISTOCHEMICAL TESTING OF F-SERIES MAbs ON FFPE SECTIONS FROM NORMAL AND OVARIAN CANCER TISSUES

| | | Normal Organs | | | Ovarian Cancer Specimens | | | |
|---|---|---|---|---|---|---|---|---|
| MAb | Conc. | Heart | Liver | Kidney | 9803 | 6918 | 8395 | 9313 |
| IgG | 10 ug/ml | — | — | — | — | — | — | — |
| F64.2 | 10 ug/ml | car m +/− | — | — | — | — | — | — |
| F74.2 | 10 ug/ml | — | — | — | — | — | — | +/− |
| F75.1 | 10 ug/ml | — | — | — | + | — | — | +/− |
| F76.2 | 10 ug/ml | — | — | — | — | — | — | + |
| F79.2 | 10 ug/ml | car m +/− | — | — | + | — | + | — |

Ovr115 is expressed in a high percentage of ovarian and pancreatic cancer cases. The fact that Ovr115 is expressed on the cell surface of cancer cells makes it an ideal target for antibody based therapy. Several Ovr115 MAbs presented above are specific for Ovr115 and do not react with fresh frozen tissues from normal vital organs.

TABLE 4D

RESULTS OF IMMUNOHISTOCHEMICAL TESTING OF D and F-SERIES MAbs ON UNFIXED AND FFPE COLON CANCER TISSUES

| MAb | | Frozen tissue | | | FFPE |
|---|---|---|---|---|---|
| Ovr115 | conc. | Cancer | NAT | Normal | cancer |
| D15.3 | 10 ug/ml | Ca +++ 7/7 | Epi +++ 1/1 | Epi +++ 2/2 | Ca +++ 1/1 |
| D20.1 | 10 ug/ml | Ca +++ 7/7 | Epi +++ 1/1 | Epi +++ 2/2 | Ca +++ 1/1 |
| D43.1 | 5 ug/ml | Ca +++ 6/6 | Epi +++ 1/1 | Epi +++ 2/2 | Ca +++ 1/1 |
| F30.1 | 10 ug/ml | Ca +++ 6/6 | Epi − 1/1 | Epi − 2/2 | |
| F64.2 | 10 ug/ml | Ca + 3/3 | Epi + 1/1 | Epi ++ 2/2 | |
| F75.1 | 10 ug/ml | Ca + 1/3 | Epi + 1/1 | Epi + 2/2 | |
| F76.2 | 0.5 ug/ml | Ca + 4/6 | Epi + 1/1 | Epi + 2/2 | |
| E-Cadherin | 0.25 ug/ml | + | + | + | + |
| IgG1 | 10 ug/ml | − | − | − | − |

In Table 4D above staining is characterized by cell type, staining score (+, ++, or +++), and positives/samples. The following abbreviations are used to indicate cell type; Epi: epithelium, Ca: cancer cell.

Although table 4D indicates that normal adjacent and normal colon tissue staining is of similar intensity to colon cancer tissue, the pattern of normal adjacent and normal colon tissue staining is more apical and focal or restricted compared to the ubiquitous staining in colon cancer tissues.

FIGS. 11A and 11C demonstrate positive membrane staining specifically in colon cancer cells with Ovr115.F64.2 in frozen colon adenocarcinoma and Ovr115.D43.1 in FFPE colon adenocarcinoma, respectively. Furthermore, FIGS. 11B and 11D display no positive staining in colon cancer when Mouse IgG1 replaced Ovr115.F64.2 in frozen colon adenocarcinoma and Mouse IgG1 replaced Ovr115.D43.1 in FFPE colon adenocarcinoma tissue. These results indicate Anti-Ovr115 antibodies specifically bind to colon cancer cells expressing Ovr115.

Therefore, Ovr115 MAbs provide adequate specificity to target tumors for immunotherapy with or without attached drugs, toxins, enzymes, prodrug activating molecules or isotopes.

Example 3

Mouse Monoclonal ELISA Detection of Ovr115

Competition ELISA

High binding polystyrene plates (Corning Life Sciences (MA)) were coated overnight at 4° C. with 1 μg/well of anti-Ovr115 MAb. The coating solution was aspirated off and free binding sites were blocked with 300 μl/well Superblock-TBS (Pierce Biotechnology, Illinois) for 1 hour at room temperature (RT). After washing 4 times with TBS/0.1% Tween20, 100 μl of Assay Buffer (TBS buffer pH 7.4; 1% BSA, 1% Calf Serum, 1% Mouse Serum, 0.1% Tween20) was added as a negative control (=noise) and 100 μl of recombinant Ovr115 (100 ng/ml) as positive control (=signal). Fifty μl of unlabeled "coating" MAb (20 μg/ml) was added and incubated with shaking at RT. After 10 minutes, 50 μl of biotinylated "detecting" MAb (2 μg/ml) was added to each well and incubated for 1 hour at RT with shaking. After washing, 100 μl of alkaline phosphatase conjugated streptavidin (Jackson ImmunoResearch Laboratories, PA) was added to each well and incubated for 30 minutes at RT while shaking. After washing, the plate was then developed using pNPP substrate in 1×DEA buffer (Pierce Biotechnology, Illinois) for 30 minutes at RT. The reaction was stopped using 100 μl/well 1N NaOH, and the plates were read at 405 nm using a Spectramax 190 plate reader (Molecular Devices, CA).

An unrelated antibody (anti-LpLPA2 antibody 4B4) was used as a control as coating and as detecting antibody. All samples were run in duplicate and for the analysis the signal/noise ratio for each antibody pair was calculated. The results of the competition ELISA using the Ovr115 MAbs are shown in Table 5.

TABLE 5

Identification of Antibody Pairs by Competition ELISA (signal to noise ratio)

| | | Detecting Mab | | | | | | | | | | | | |
|---|---|---|---|---|---|---|---|---|---|---|---|---|---|---|
| | | A2.1 | A11.1 | A51.2 | A52.1 | A63.2 | F21.1 | F32.2 | F62.2 | F64.2 | F74.2 | F75.1 | F76.2 | F9.2 | control |
| Capture Mab | A52.1 | 1.6 | 1.2 | 1.5 | 1.0 | 2.2 | 2.7 | 1.5 | 1.1 | 2.2 | 3.9 | 3.5 | 4.7 | 2.7 | 1.0 |
| | A63.2 | 1.0 | 1.3 | 2.2 | 1.1 | 1.3 | _7.7_ | 2.1 | 1.1 | _6.9_ | _12.5_ | _11.5_ | _14.8_ | _7.6_ | 1.1 |
| | D43.1 | 1.7 | 1.2 | 1.2 | 1.0 | 3.6 | 4.6 | 2.1 | 1.1 | 4.4 | _9.0_ | _7.5_ | _10.7_ | 4.9 | 1.1 |
| | D71.1 | 1.3 | 1.2 | 1.1 | _6.7_ | _9.2_ | 1.2 | 1.9 | 1.2 | 4.1 | _8.2_ | _6.7_ | _8.5_ | 4.4 | 1.0 |
| | F21.1 | 1.2 | 1.0 | 1.0 | 1.0 | 1.1 | 1.0 | 1.1 | 1.0 | 1.2 | 1.5 | 1.4 | 1.7 | 1.2 | 1.0 |
| | F30.1 | 1.9 | 1.6 | 2.6 | 1.1 | 4.6 | _9.4_ | 2.7 | 1.1 | 2.6 | _7.7_ | _5.7_ | _11.4_ | _6.7_ | 1.0 |
| | F55.2 | 1.8 | 1.4 | 2.3 | 1.1 | 3.8 | _7.2_ | 2.4 | 1.1 | 3.4 | _6.4_ | _5.4_ | _9.7_ | _5.8_ | 1.0 |
| | F62.2 | 1.5 | 1.1 | 1.8 | 1.1 | 2.5 | _6.0_ | 1.9 | 1.0 | 3.6 | _11.4_ | _9.2_ | _12.8_ | _6.2_ | 1.0 |
| | F64.2 | 2.3 | 1.4 | 2.4 | 1.1 | 3.5 | _6.0_ | 2.5 | 1.1 | 1.1 | 3.1 | 1.4 | _10.4_ | _5.2_ | 1.0 |
| | F74.2 | 2.1 | 1.4 | 1.9 | 1.1 | 3.3 | _6.3_ | 2.0 | 1.1 | 1.0 | 1.1 | 1.0 | _9.6_ | 3.9 | 0.9 |
| | F75.1 | 1.9 | 1.4 | 1.9 | 1.1 | 3.1 | _5.3_ | 1.9 | 1.1 | 1.0 | 1.5 | 1.1 | _8.7_ | 3.8 | 1.0 |
| | F76.2 | 1.6 | 1.4 | 1.5 | 1.0 | 2.5 | 4.3 | 1.6 | 1.2 | 2.4 | _6.5_ | 5.0 | 1.3 | 3.2 | 1.0 |
| | F79.2 | 2.4 | 1.7 | 3.2 | 1.2 | _6.2_ | _13.3_ | 3.3 | 1.1 | _5.5_ | _12.6_ | _9.7_ | _16.0_ | _8.3_ | 1.0 |
| | F9.2 | 2.2 | 1.5 | 1.8 | 1.1 | 3.6 | _5.4_ | 2.3 | 1.1 | 3.7 | _8.5_ | _6.9_ | 1.1 | 1.1 | 0.9 |
| | control | 1.1 | 1.1 | 1.3 | 1.0 | 1.4 | 1.0 | 1.2 | 1.0 | 1.5 | 1.0 | 1.0 | 1.1 | 1.6 | 1.0 |

Underlined values indicate a favorable signal to noise ratio for that MAb pair

The results of the checkerboard ELISA testing 5 MAbs from the A-series, 2 MAbs from the D-series and 13 MAbs from the F-series are shown in the table above. The antibodies were tested as coating as well as detecting antibody in all possible combinations. The results are shown as specific signal/noise ratio. Underlined values in Table 5 above indicate a favorable signal to noise ratio for that MAb pair. During the incubation with detecting antibody, a 10-fold higher concentration of coating antibody was added to the well to prevent self-pairing. Self-pairing can be observed when antigens are partly multimerized and can confound epitope mapping results. Testing by competitive/blocking ELISA assay assures that antibodies cannot bind to the same epitope when the antigen is in multimeric form.

The data suggest that one very antigenic epitope is recognized by antibodies from the A-series, D-series and F-series (A52.1, D43.1, F30.1, F55.1, F62.1, and F79.1). Another epitope is recognized by F74.1, F75.1 and F64.1. Distinct from the first two epitopes is a third epitope that is recognized by F76.1 and F9.1. The MAbs Ovr115.D71 and Ovr115.F21 may react with epitopes which are proximal to that of Ovr115.A63.2, since these MAbs in combination result in a lower signal, whereas the other epitopes are apparently all unique from each other and from the Ovr115.D71/Ovr115.F21 and Ovr115 63.2 epitopes. The epitope map of the Ovr115 MAbs derived from the results in Table 5 is shown in FIG. 12. In summary, we can observe that the Ovr115 MAbs detected at least four distinct epitopes from this pairing analysis.

In addition, all antibodies were tested in a direct ELISA using recombinant insect and recombinant mammalian protein for coating. The results indicate that the A-series antibodies have a higher affinity for insect-derived Ovr115 than for the recombinant Ovr115 from 293 cells while the F-series bind to both proteins with high affinity. Therefore, we used antibodies from the F-series for subsequent experiments in cancer cell lines and serum.

Sandwich ELISA

High binding polystyrene plates (Corning Life Sciences (MA)) were coated overnight at 4° C. with 1 μg/well of anti-Ovr115 MAb. Free binding sites were blocked with 300 μl/well Superblock-TBS (Pierce Biotechnology, Illinois) for 1 hour at room temperature (RT). After washing 4-times with TBS/0.1% Tween20, 100 ul of Assay buffer and 20 ul of standard (250, 125, 62.5, 31.3, 15.6, 7.8, 3.9 and 0 ng/ml Ovr115) or sample were added for 1 hour incubation. After washing, 100 ul of biotinylated antibody (1 ug/ml) was added for 1 hour incubation. After washing, 100 μl of alkaline phosphatase conjugated streptavidin (Jackson ImmunoResearch Laboratories, PA) was added to each well and incubated for 30 minutes at RT while shaking. The plate was washed and then developed using pNPP substrate in 1×DEA buffer (Pierce Biotechnology, Illinois) for 30 minutes at RT. The reaction was stopped using 100 μl/well 1N NaOH, and the plates were read at 405 nm using a Spectramax 190 plate reader (Molecular Devices, CA).

Several different combinations of antibodies were tested to establish a sandwich ELISA assay with high sensitivity and specificity for the detection of native Ovr115 in tissue extracts and serum samples. FIG. 13 demonstrates the detection of the Ovr115 protein by sandwich ELISA using various MAb pairs in medium (supernatant) and cell extracts from Ovr115 transfected 293T cells and in extracts from the Ovr115 mRNA positive tumor cell lines CaOv3, LNCAP and LoVo. These data indicate the usefulness of using Ovr115 MAbs for the detection of Ovr115 in blood, serum, or other bodily fluids from patients.

Example 4

Anti-Ovr115 Activity Screening Assay

Substrate Screening

Fluorescent protein substrates (TR-X or FL labeled BSA, casein and ovary albumin) and rhodamine B labeled peptides were purchased from Molecular Probes (Eugene, Oreg.) to screen Ovr115 specificity. Assay buffers were used following the manufacturer's protocols and varied depending on the substrate. Generally, assays were carried out in 10-20 mM Tris/HCl pH 7.5. The final concentration for protein substrates was 10 μg/ml and 100 μM for peptide substrates. The final concentration for Ovr115 was 34 μg/ml (0.73 μM). All assays were carried out in 96 well-plates. Reactions were monitored by following fluorescence reading (Ex 590 nm/Em 650 nm for TR-X label and Ex 485 nm/Em 530 nm for FL and rhodamine B labels). Substrate screening indicated rhodamine 110, bis-(CBZ-L-phenylalanyl-L-arginine amide), dihydrochloride; also known as (CBZ-Phe-Arg)$_2$-R110 or FR, to be readily hydrolyzed by Ovr115.

Assay Format and Screening Results

Subsequent to substrate screening, kinetic analysis and assay optimization the following Anti-Ovr115 activity assay format was developed. 25 μl of Ovr115 (17.2 μg/ml) was added to 50 μl of antibody solution (0.5 or 6.2 times mol. excess) and incubated at room temperature for 15-30 minutes. After incubation, the reaction was started by the addition of 25 μl of substrate (5 μM FR peptide). TBS at pH 7.5 was used to buffer solutions. For negative controls either no Ovr115 was added or 120 mM Benzamidine was added as an inhibitor to Ovr115. It was determined that the inhibitory concentration (IC50) for Benzamidine against Ovr115 is 0.316 mM. For positive controls either no anti-Ovr115 antibody was added, or an unrelated antibody was added.

FIG. 14 shows the results of screening Ovr115 antibodies for inhibition of Ovr115 activity. The figure demonstrates that the MAbs Ovr115.F9.2, Ovr115.F21.1, Ovr115.F30.1, Ovr115.F32.2, Ovr115.F55.2, Ovr115.F62.2 and Ovr115.F76.2 at a concentration of 0.19 μM (0.5 times mol. excess) significantly reduce Ovr115 activity compared to Ovr110 antibodies (positive control). Higher concentrations over anti-Ovr115 antibodies resulted in further reduction of Ovr115 activity. This reduction of Ovr115 activity may be due to blocking of the protease active site, steric hindering of Ovr115, or conformational change of the Ovr115 protein.

Therefore, the binding of MAbs Ovr115.F9.2, Ovr115.F21.1, Ovr115.F30.1, Ovr115.F32.2, Ovr115.F55.2, Ovr115.F62.2 and Ovr115.F76.2 significantly reduces the activity of Ovr115. The anti-Ovr115 activity screening data demonstrates Ovr115 MAbs are suitable for immunotherapy of Ovr115 expressing cells with or without conjugated drugs, toxins, enzymes, prodrug activating molecules or isotopes.

Example 5

Functional Validation of Ovr115

Cells and Cell Culture

RK3E, HT-29, CAPAN-2 and HCT-116 cell lines were purchased from American Type Culture Collection (Manassas, Va.). Cells were grown in DMEM (Invitrogen) with L-glutamine plus 4.5 g/L glucose and supplemented with 10% FBS and 100 U/mL Penicillin/Streptomycin (Cellgro). All cells were maintained in a humidified 37° C. incubator with 5% CO$_2$.

SDS-PAGE and Western Immunoblot Analysis

Extracts from tumor cell or virus-infected cell monolayers were prepared on ice using solubilization buffer (1% NP40, 10 mM Na$_2$PO$_4$, 0.15M NaCl) plus a protease inhibitor cocktail (Roche Inc.). Protein extracts from human tumors or harvested tumors from xenograft experiments were prepared by homogenization of snap-frozen, minced tumor tissue in extraction buffer (50 mM Tris-HCl, pH 7.2, 150 mM NaCl, 5 mM EDTA, 0.5% IG-Pal plus protease inhibitors) followed by sonication and then centrifugation in a microfuge to clarify the extracts. Between 20 and 50 ug of protein extract were used for each gel lane; protein equivalent concentrations were evaluated for protein level comparisons on the same gel. Clarified extracts were mixed with an equal volume of 2× concentrated Laemmli sample buffer (Invitrogen), heated to 70° C. for 10 minutes and then analyzed using pre-cast 4-12% SDS-polyacrylamide minigels (Nupage, Invitrogen) with MES running buffer (Nupage; Invitrogen). Gels were transferred to Immobilon-P 0.45 µm membranes (Invitrogen) using 1× Nupage transfer buffer plus 10% Methanol. The membranes were rinsed and blocked for 1 hour at room temperature using 5% nonfat dry milk in PBS with 0.05% Tween-20. Membranes were incubated with primary antibody overnight in 5% nonfat dry milk in PBS with 0.05% Tween-20. A mouse monoclonal antibody directed against Ovr115 (F21.1) was produced in house and was used at a final concentration of 1 ug/ml. Following primary antibody incubation, membranes were washed four times 10 min. at room temperature in 1×PBS with 0.05% Tween-20. Horseradish peroxidase linked goat anti-mouse immunoglobulin (Jackson Lab Inc.) was used (1:10,000 dilution) in 5% nonfat dry milk in PBS plus 0.05% Tween-20 for 1 hour at room temperature to detect the primary monoclonal antibody. Membranes were washed four times 10 min. in 1×PBS including 0.05% Tween-20 followed by detection using enhanced chemiluminescence (ECL) reagent per manufacturer's directions (Amersham) and exposure to X-ray film (Kodak).

FIG. 15 demonstrates the Ovr115 MAbs, specifically Ovr115.F21.1, recognizes native Ovr115 protein in human cell lines and ovarian tumors.

Retroviral Vector Construction

A cDNA encoding Ovr115 was obtained by PCR from a tumor cDNA preparation. The cDNA was cloned into the Hpa I cloning site of the pLXSN vector (BD Bioscience/Clontech) and sequence verified. A mutant Ovr115 protein lacking protease activity was constructed by using oligonucleotide directed mutagenesis to convert the catalytic triad serine residue 385 to an alanine. The resulting mutant cDNA was sequence verified and cloned into the pLXSN vector. pLAPSN, a retroviral expression vector encoding alkaline phosphatase (AP), was purchased from BD Bioscience/Clontech (pLXSN-AP) and was used as a negative control. A retroviral expression vector encoding activated v-Ras, which was used as a positive control for the apoptosis assay, was constructed by subcloning the RasV12 cDNA from pCMV-RasV12 into pLXSN (BD Bioscience/Clontech).

Virus Production

Ecotropic virus was used to infect RK3E cells. For virus production 293T cells were seeded at a density of $8\times10^5$ cells per well of a 6 well dish onto Biocoat collagen coated plates (BD). Twenty-four hours later cells were transfected with plasmids using Lipofectamine with the addition of PLUS reagent (Invitrogen) according to the manufacturers recommendations. Virus plasmid DNA: pLXSN-Ovr115 wild type, pLXSN-Ovr115 mutant, pLXSN-AP or pLXSN-Ras plus pVpack-Eco and pVpackGP (Stratagene) were transfected for three hours after which the cells were grown overnight in DMEM containing 20% FBS. The medium was then changed to DMEM supplemented with 10% FBS+100 U/mL Pen/Strep and virus-containing media were harvested 24 hours later and filtered through a 0.45 µm polysulfonic filter.

Virus Infection and Selection

Polybrene (Hexadimethrine Bromide; Sigma) was added to fresh virus-containing medium at a final concentration of 4 µg/ml. RK3E cells, plated the day before at a density of $3\times10^5$ cells per 100 mm$^2$ dish, were washed once with phosphate-buffered saline including Ca2+ and Mg2+ (cellgro). The virus containing medium was applied directly to the cells and then incubated for 3 hours at 37° C. with occasional swirling. The medium was replaced by fresh growth medium and the cells incubated at 37° C. for 60-72 hours at which point a final concentration of 350 ug/mL of G418 sulfate (Cellgro) was added to the growth medium to select for virus-infected cells. Following G418 selection, pools of cells were used for all subsequent experiments. Expression of ectopic proteins in the virus-infected, selected cells was verified by immunoblot and expression of AP was monitored by staining.

Soft Agar Assay

Soft agar assays were conducted using 6-well plates (Corning). The 2 ml bottom agar base layer consisted of 0.8% agar, 10% FBS in Iscove's medium (Invitrogen). Trypsinized cells were suspended in 0.4% agar, 10% FBS in Iscove's medium and applied in a 5 ml final volume on top of the solidified base layer. Three different viable cell numbers, $10^5$, $10^4$ and $5\times10^3$ cells, were seeded in agar per well in duplicate. A final 2 ml layer consisting of 0.8% agar, 10% FBS in Iscove's medium was applied on top of the solidified cell layer. The agar plates were then incubated at 37° C. for approximately 10-14 days until colonies appeared. Colonies were allowed to grow further and were counted between 2 and 4 weeks. The soft agar was maintained by weekly feeding with growth medium.

FIG. 16A is a simple schematic of the step taken to perform the soft agar assay. FIGS. 16B and 16C demonstrate significant colony growth of Ovr115 expressing cells and limited growth of AP expressing cells. Furthermore, cells expressing mutated Ovr115 lacking protease activity only produced limited colonies indicating that Ovr115 protease activity is essential for cellular proliferation. FIG. 16D is a western blot that confirms Ovr115 wild type and the Ovr115 mutant lacking protease activity are produced by the cells in the soft agar colonies.

Tumor Xenografts

Retrovirus-infected, G418-selected pools of RK3E cells expressing either AP or Ovr115 were injected subcutaneously into SCID/Beige mice (Charles River Laboratories). Nine mice were used per group and $5\times10^6$ cells in 100 µl PBS were implanted without using matrigel. Tumor formation was monitored by palpation and caliper measurement and tumor volume was calculated using the formula: (length×width$^2$)/2.

RK3E cells expressing Ovr115 or AP in the soft agar assay above were used for tumor xenografts experiment for continuity. FIG. 17 demonstrates a significant increase in mean tumor volume over time for cells expressing Ovr115 compared to cells expressing AP. This data indicates that Ovr115 expression and Ovr115 activity is results in tumor progression. FIG. 18 is a western blot that confirms Ovr115 was expressed by the tumors developed in the xenograft experiment.

Apoptosis Assay $2\times10^5$ RK3E cells expressing AP (negative control), Ras (positive control) or Ovr115 by retroviral infection and selection were suspended in culture medium without serum and incubated on poly (2-hydroxyethyl-methacrylate) (Sigma) coated plates. After 24 hours at 37° C. cells were harvested by centrifugation and evaluated for apoptosis with a "Guava Nexin V-PE Kit" (Guava Technologies Inc.). After washing approximately 105 cells were resuspended in 40 µl provided buffer and 5 µl each Annexin V (+) and 7-AAD (−) were added. Following 20 minutes incubation on ice, cells were analyzed using the Guava PCA machine according to manufacturer's instructions.

FIG. 19 demonstrates that fewer cells expressing Ovr115 undergo apoptosis than cells expressing AP (negative control). Furthermore, the low percentage of early apoptotic cells expressing Ovr115 is roughly the same as the cells expressing Ras (positive control).

Example 6

Killing of HT29 Colon Tumor Cells by Incubation with Ovr115-MAbs and Anti-Mouse MAb Saporin Conjugate Experiments were performed by incubating HT29 colon tumor cells with Ovr115 MAbs premixed with MAb-zap goat anti-mouse Ig saporin conjugate (Advanced Targeting Systems, San Diego, Calif.) and measuring cell viability at 72 and 96 h, to detect potential killing effects on these Ovr115 expressing cells. On day 1, HT29 cells were placed into 96 well, flat bottom, sterile cell culture plates (Corning), in triplicate wells, at 1,500 cells/75 µL/well, in F12 medium with 10% FBS, P/S. Plates were incubated at 37° C., in 5% CO2, overnight. Duplicate plates were set up to allow readings at 72 h and 96 h. On Day 2 (0 h), 25 µL of 4× final MAb concentrations alone, or 25 µL of 4×MAb premixed with 25 µL of 4×MAb Zap, or 25 µL of 4×Mab Zap alone, or 25 µL of medium alone were added to wells of the 96 well plates, in triplicate, to a final volume of 100 µL. Final MAb concentrations were 2 µg/mL, 0.4 µg/mL, 0.08 µg/mL and 0 µg/mL and the final concentration of MAb Zap was 1 µg/mL. Triplicate wells with medium alone, MAb alone (2 µg/mL only) and MAb Zap alone were used as negative controls. The anti-transferrin receptor MAb 5E9 (ATCC, Manassas, Va.) was used as a positive control MAb for killing. Plates were shaken gently for five minutes to mix the reagents and then incubated at 37° C., in 5% CO2. On day 5 (72 h), 10 µL of a of Alamar Blue stock solution (Biosource International, Camarillo, Calif.) was added to wells of the first set of plates and they were incubated at 37° C., in 5% CO2 for 2-7 h. Plates were then analyzed on a SpectraMAX GeminiEM spectrophotometer (Molecular Devices, Sunnyvale, Calif.) (emission=590 nm, excitation=560 nm and Autocutoff=570 nm) and viability was expressed as a percentage the control wells with medium alone.

TABLE 6

HT29 killing by Ovr115 MAb & MAb Zap Saporin Conjugate

Percent Growth Inhibition Compared to Wells with Medium Alone

| Mab Clone | Percent HT29 Positive with MAb (IF)* | MAb Zap | MAb (2 µg/mL) | MAb + MAb Zap w/ saporin conjugate | | MAb (2 µg/mL) |
|---|---|---|---|---|---|---|
| | | | | MAb (0.08 µg/mL) | MAb (0.4 µg/mL) | |
| 5E9 TFR | — | 0 | 2 | 18 | 58 | 35 |
| Isotype Control | — | 1 | - | −10 | −4 | −6 |
| D20.1 | 10-15 | 0 | 20 | 10 | −15 | 12 |
| D84.2 | — | 0 | −3 | 3 | 6 | 15 |
| F21.1 | — | 2 | 12 | 8 | −2 | −12 |
| F30.1 | — | 1 | 16 | −12 | 0 | −2 |
| F76.2 | 100 | 0 | 10 | 0 | 15 | 18 |

*Immunofluorescence microscopy as detailed in Example 2.

Results of testing Ovr115.D20.1, Ovr115.D84.2, Ovr115.F21.1, Ovr115.F30.1, and Ovr115.F76.1 are presented in Table 6 above. As can be seen, the MAb Zap alone did not inhibit growth of the HT29 cells (0-2% inhibition). Similarly the irrelevant isotype control, MAb did not inhibit growth of the HT29 cells. Incubation of the Ovr115.D20.1, Ovr115.F21.1, Ovr115.F30.1 and Ovr115.F76.1 MAbs, alone with the HT29 cells, produced 20%, 12%, 16% and 10% growth inhibition of HT29 cells (respectively). Whereas, when added with MAb Zap saporin conjugate, Ovr115.D20.1, Ovr115.D84.2, Ovr115.F21.1 and Ovr115.F76.1 MAbs produced between 8 to 18% growth inhibition of HT29 tumor cells.

Ovr115.F76.2 in particular, at concentrations of 0.04 and 2.0 µg/mL together with MAb Zap resulted in 15-18% greater growth inhibition, than MAb Zap alone. Moreover, Ovr115.D20.1, at concentrations of 0.08 and 2.0 µg/ml together with MAb Zap resulted in 10-12% growth inhibition compared to 0% inhibition by MAb Zap alone. Likewise, Ovr115.D84.2, at concentrations of 0.4 and 2.0 µg/mL together with MAb Zap resulted in 6-15% growth inhibition compared to 0% inhibition by MAb Zap alone. Similar results were observed with Capan human pancreatic cancer cells and SKBR3 human breast cancer cells.

In conclusion, growth inhibition of Ovr115 expressing HT29 tumor cells was obtained at concentrations of MAb which are easily achievable in-vivo, for therapeutic purpose. These in-vitro data indicate that the Ovr115 MAbs above are suitable for targeting of tumor cells in-vivo, with or without attached drug, toxin, enzyme, prodrug or isotope.

Example 7

Deposits

Deposit of Cell Lines and DNA

Hybridoma cell lines were deposited with the American Type Culture Collection (ATCC) located at 10801 University Boulevard, Manassas, Va. 20110-2209, U.S.A., and accorded accession numbers.

The following hybridoma cell lines were deposited with ATCC, Ovr115 A51.2, Ovr115.D20.1, Ovr115.D84.2, Ovr115.F21.1, Ovr115.F30.1, Ovr115.F64.2 and Ovr115.F76.2. The names of the deposited hybridoma cell lines above may be shortened for convenience of reference. E.g. A01.1 corresponds to Ovr115.A01.1. These hybridomas correspond to the clones (with their full names) deposited with the ATCC. Table 7 lists the hybridoma clone deposited with the ATCC, the accorded ATCC accession number, and the date of deposit.

TABLE 7

ATCC deposits

| Hybridoma | ATCC Accession No. | Deposit Date |
|---|---|---|
| Ovr115 A51.2 | PTA-5202 | May 16, 2003 |
| Ovr115.D20.1 | PTA-5916 | Apr. 16, 2004 |
| Ovr115.D84.2 | PTA-5917 | Apr. 16, 2004 |
| Ovr115.F21.1 | PTA-5918 | Apr. 16, 2004 |
| Ovr115.F30.1 | PTA-5919 | Apr. 16, 2004 |
| Ovr115.F76.2 | PTA-5920 | Apr. 16, 2004 |
| Ovr115.F64.2 | PTA-6550 | Jan. 28, 2005 |

These deposits were made under the provisions of the Budapest Treaty on the International Recognition of the Deposit of Microorganisms for the Purpose of Patent Procedure and the Regulations there under (Budapest Treaty). This assures maintenance of viable cultures for 30 years from the date of deposit. The organisms will be made available by ATCC under the terms of the Budapest Treaty, and subject to an agreement between diaDexus, Inc. and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S.

Commissioner of Patents and Trademarks to be entitled thereto according to 35 USC §122 and the Commissioner's rules pursuant thereto (including 3 7 CFR §1.14 with particular reference to 886 OG 638).

The assignee of the present application has agreed that if the cultures on deposit should die or be lost or destroyed when cultivated under suitable conditions, they will be promptly replaced on notification with a viable specimen of the same culture. Availability of the deposited strains are not to be construed as a license to practice the invention in contravention of the rights granted under the authority of any government in accordance with its patent laws. The making of these deposits is by no means an admission that deposits are required to enable the invention

We claim:

1. An isolated Ovr115 antibody wherein the antibody is produced by a hybridoma selected from the group consisting of American Type Culture Collection accession number PTA-5202, PTA-5916, PTA-5917, PTA-5918, PTA-5919, PTA-5920 and PTA-6550.

2. The isolated Ovr115 antibody of claim 1, wherein said antibody binds to Ovr115 on a mammalian cell in vivo.

3. The antibody of claim 2 which internalizes upon binding to Ovr115 on a mammalian cell in vivo.

4. The antibody of claim 1 which is a monoclonal, a chimeric, a human or a humanized antibody.

5. The antibody of claim 1 which is conjugated to a growth inhibitory agent or a cytotoxic agent.

6. The antibody of claim 5 wherein the cytotoxic agent is selected from the group consisting of toxins, antibiotics, radioactive isotopes and nucleolytic enzymes.

7. The antibody of claim 6, wherein the toxin is selected from the group consisting of ricin, saponin, maytansinoid and calicheamicin.

8. The antibody of claim 1, wherein said antibody inhibits the growth of Ovr115-expressing cancer cells.

9. The antibody of claim 8 which is a monoclonal, chimeric, humanized or human antibody.

10. The antibody of claim 9 which is produced in bacteria.

11. The antibody of claim 8, wherein the cancer cells are from a cancer selected from the group consisting of ovarian, pancreatic and colon cancer.

12. The antibody of claim 1 which internalizes upon binding to Ovr115 on a mammalian cell in vivo.

13. The antibody of claim 1 which is produced by a hybridoma of American Type Culture Collection accession number PTA-6550.

14. The antibody of claim 1 which is produced by a hybridoma of American Type Culture Collection accession number PTA-5202.

15. The antibody of claim 1 which is produced by a hybridoma of American Type Culture Collection accession number PTA-5916.

16. The antibody of claim 1 which is produced by a hybridoma of American Type Culture Collection accession number PTA-5917.

17. The antibody of claim 1 which is produced by a hybridoma of American Type Culture Collection accession number PTA-5918.

18. The antibody of claim 1 which is produced by a hybridoma of American Type Culture Collection accession number PTA-5919.

19. The antibody of claim 1 which is produced by a hybridoma of American Type Culture Collection accession number PTA-5920.

20. The antibody of claim 1, wherein said antibody is labeled.

21. The antibody of claim 20 wherein the label is selected from the group consisting of radio, fluorescent, gold particle, enzymatic and biotin labels.

22. The antibody of claim 1, wherein said antibody inhibits Ovr115 protease activity.

23. A cell that produces the antibody of claim 1.

24. A composition comprising the antibody of claim 1, and a carrier.

25. The composition of claim 24, wherein the antibody is conjugated to a cytotoxic agent.

26. The composition of claim 24, wherein the antibody is a monoclonal, chimeric, human or humanized antibody and the carrier is a pharmaceutical carrier.

27. An article of manufacture comprising a container and the antibody of claim 1.

28. The article of manufacture of claim 27 which further comprises a carrier.

29. The article of manufacture of claim 27 which further comprises a label or package insert.

30. A kit comprising a container and a composition comprising the antibody of claim 1.

31. The kit of claim 30 wherein the antibody is coupled to a solid support.

32. The kit of claim 30 which further comprises a label or package insert.

33. A method of killing an Ovr115-expressing cancer cell, comprising contacting the cancer cell with the antibody of claim 2, thereby killing the cancer cell.

34. The method of claim 33, wherein the cancer cell is selected from the group consisting of ovarian, pancreatic and colon cancer cell.

35. The method of claim 33, wherein the antibody is conjugated to a cytotoxic agent.

36. The method of claim 35, wherein the cytotoxic agent is a toxin selected from the group consisting of maytansinoid, ricin, saporin and calicheamicin or a radioisotope.

37. The method of claim 33, wherein the antibody is administered in conjunction with at least one chemotherapeutic agent.

38. The method of claim 37 wherein the chemotherapeutic agent is paclitaxel or derivatives thereof.

39. A method for determining if cells in a sample express Ovr115 comprising
   (a) contacting a sample of cells with an Ovr115 antibody of claim 2 under conditions suitable for specific binding of the Ovr115 antibody to Ovr115 and
   (b) determining the level of binding of the antibody to cells in the sample, or the level of Ovr115 antibody internalization by cells in said sample,
   wherein Ovr115 antibody binding to cells in the sample or internalization of the Ovr115 antibody by cells in the sample indicate cells in the sample express Ovr115.

40. A method for detecting Ovr115 overexpression in a subject in need thereof comprising,
   (a) combining a serum sample of a subject with an Ovr115 antibody of claim 2 under conditions suitable for specific binding of the Ovr115 antibody to Ovr115 in said serum sample
   (b) determining the level of Ovr115 in the serum sample,
   (c) comparing the level of Ovr115 determined in step b to the level of Ovr115 in a control,
   wherein an increase in the level of Ovr115 in the serum sample from the subject as compared to the control is indicative of Ovr115 overexpression in the subject.

41. The method of claim 40 wherein the subject has cancer.

42. The method of claim 41 wherein the subject has ovarian, pancreatic or colon cancer.

43. A method for determining if cells in a sample express Ovr115 comprising
   (a) contacting a sample of cells with an Ovr115 antibody of claim 1 under conditions suitable for specific binding of the Ovr115 antibody to Ovr115 and
   (b) determining the level of binding of the antibody to cells in the sample, or the level of Ovr115 antibody internalization by cells in said sample,
   wherein Ovr115 antibody binding to cells in the sample or internalization of the Ovr115 antibody by cells in the sample indicate cells in the sample express Ovr115.

44. A method for detecting Ovr115 overexpression in a subject in need thereof comprising,
   (a) combining a serum sample of a subject with an Ovr115 antibody of claim 1 under conditions suitable for specific binding of the Ovr115 antibody to Ovr115 in said serum sample
   (b) determining the level of Ovr115 in the serum sample,
   (c) comparing the level of Ovr115 determined in step b to the level of Ovr115 in a control,
   wherein an increase in the level of Ovr115 in the serum sample from the subject as compared to the control is indicative of Ovr115 overexpression in the subject.

45. The method of claim 44 wherein the subject has cancer.

46. The method of claim 44 wherein the subject has ovarian, pancreatic or colon cancer.

* * * * *